US008629259B2

(12) United States Patent
Scherz et al.

(10) Patent No.: US 8,629,259 B2
(45) Date of Patent: Jan. 14, 2014

(54) PHOTOSYNTHETIC ORGANISMS AND COMPOSITIONS AND METHODS OF GENERATING SAME

(75) Inventors: Avigdor Scherz, Rehovot (IL); Oksana Shlyk-Kerner, Rehovot (IL); Ilan Samish, Nes Ziona (IL); David Kaftan, Nove Hrady (CZ); Jorge Dinamarca, Victoria (CL)

(73) Assignee: Yeda Research and Development Co. Ltd., Rehovot (IL)

( * ) Notice: Subject to any disclaimer, the term of this patent is extended or adjusted under 35 U.S.C. 154(b) by 879 days.

(21) Appl. No.: 12/309,415

(22) PCT Filed: Jul. 22, 2007

(86) PCT No.: PCT/IL2007/000920
§ 371 (c)(1),
(2), (4) Date: Oct. 5, 2009

(87) PCT Pub. No.: WO2008/010228
PCT Pub. Date: Jan. 24, 2008

(65) Prior Publication Data
US 2010/0031395 A1 Feb. 4, 2010

Related U.S. Application Data

(60) Provisional application No. 60/831,937, filed on Jul. 20, 2006.

(51) Int. Cl.
*C12N 15/31* (2006.01)
*C12N 15/52* (2006.01)
*C12N 15/82* (2006.01)

(52) U.S. Cl.
USPC ............... 536/23.7; 435/257.2; 435/320.1; 435/419; 435/468; 800/281; 800/284; 800/290; 800/296; 800/298

(58) Field of Classification Search
USPC ................................ 800/278–320
See application file for complete search history.

(56) References Cited

U.S. PATENT DOCUMENTS 5,717,129 A * 2/1998 Songstad et al. ............ 800/266

FOREIGN PATENT DOCUMENTS

WO WO 2008/010228 1/2008

OTHER PUBLICATIONS

Ei-Lithy M. et al. in the Journal of Experimental Botany, Jun. 2005; vol. 56, No. 416; pp. 1625-1634.*
Kloos, R. et al. Z. Naturforschung (1993) vol. 48c, pp. 799-802.*
Alfonso, M et al. Planta (2001) vol. 212, pp. 573-582.*

Invitation to Pay Additional Fees Dated Jul. 15, 2008 From the International Searching Authority Re.: Application No. PCT/IL07/00920.
Alfonso et al. "Unusual Tolerance to High Temperatures in a New Herbicide-Resistnat D1 Mutant From Glycine Max (L.) Merr. Cell Cultures Deficient in Fatty Acid Desaturation", Planta, 212: 573-582, 2001. Abstract, Intro, Last §.
Dibrov et al. "Structure of the D1 Subunit of Photosystem II in the Thermophyllic Cyanobacterium *Synechococcus* Vulcanus", GenBank Accession No. X79222, May 17, 1994.
"RecName: Full=Photosystem Q(B) Protein 2; AltName: Full=32 kDa Thylakoid Membrane Protein 2; AltName: Full=Photosystem II Protein D1 2; Flags: Precursor", XP002557090, DATABASE UniProt [Online], Retrieved From EBI, Accession No. UNIPROT:P16033, Database Accession No. P16033. Abstract, 1989.
Supplementary European Search Report and the European Search Opinion Dated Dec. 8, 2009 From the European Patent Office Re.: Application No. 07789975.5.
Alfonso et al. "Induced New Mutation of D1 Serine-268 in Soybean Photosynthetic Cell Cultures Produced Atrazine Resistance, Increased Stability of S2QB- and S3QB- States, and Increased Sensitivity to Light Stress", Plant Physiology, XP002557157, 112(4): 1499-1508, 1996. Abstract, p. 1500, l-h Col., § 3, p. 1501, r-h Col., §3-p. 1502, Col., K, § 2, p. 1502, r-h Col., § 4-p. 1503, r-h Col., Line 5.
Kloos et al. "Complete Sequence of the PsbA Gene From the Thermophilic Cyanobacterium *Synechococcus* Elongatus", Zeitschrift für Naturforschung, Section C Biosciences, XP009126278, 48(9-10): 799-802, 1993. p. 801, l-h Col., § 2-r-h Col., § 1.
Motoki et al. "The Two PsbA Genes From the Thermophilic Cyanobacterium *Synechococcus* Elongatus", Plant Physiology, XP002557089, 108(3): 1305-1306, 1995. p. 1305, l-h Col., § 4-r-h Col., Line 7.
Shimizu et al. "Nucleotide Sequences of the PsaA and PsaB Genes Encoding the Photosystem I Core Proteins From the Thermophilic Cyanobacterium *Synechococcus* Vulcanus", Plant Molecular Biology, XP009126281, 18(4): 785-791, 1992. p. 788, l-h Col., Line 11-r-h Col., Line 3.
Shlyk-Kerner et al. "Protein Flexibility Acclimatizes Photosynthetic Energy Conversion to the Ambient Temperature", Nature, XP002557088, 442(7104): 827-830, Aug. 2006. p. 827, r-h Col., § 2-p. 829, r-h Col., Line 5, Supplementary Material.
Office Action Dated Feb. 10, 2011 From the Israel Patent Office Re. Application No. 196588 and Its Translation Into English.
Response Dated Sep. 29, 2010 to Communication Pursuant to Article 94(3) EPC of Mar. 29, 2010 From the European Patent Office Re.: Application No. 07789975.5.
Dinamarca et al. "Mesophilic Cyanobacterium Becomes Thermotolerant by Double Mutation in D1 Protein of Photosystem II", Department of Plant Sciences, The Weizman Institute of Science, Israel, 24 P.
International Search Report and the Written Opinion Dated Sep. 23, 2008 From the International Searching Authority Re.: Application No. PCT/IL07/00920.

(Continued)

Primary Examiner — Russell Kallis

(57) ABSTRACT

An isolated polynucleotide is provided. The isolated polynucleotide comprising a nucleic acid sequence encoding a polypeptide of a Type II reaction center of a photosynthetic organism, the nucleic acid sequence being capable of imparting the type II reaction center with an activity under a temperature range different than that of the type II reaction center endogenous to the photosynthetic organism. Also provided are methods of using the sequences for generating photosynthetic organisms or tailor-made thermotolerance.

16 Claims, 19 Drawing Sheets
(15 of 19 Drawing Sheet(s) Filed in Color)

(56) References Cited

OTHER PUBLICATIONS

Shimizu et al. "Nucleotide Sequences of the PsaA and PsaB Genes Encoding the Photosystem I Core Proteins From the Thermophilic Cyanobacterium *Synechococcus* Vulcanus", Plant Molecular Biology, XP009126281, 18(4): 785-791, 1992. p. 788, l-h col. Line 11-r-h Col., Line 3.

Behrenfeld et al. "Climate-Driven Trends in Contemporary Ocean Productivity", Nature, 444: 752-755, Dec. 7, 2006.

Murata et al. "Photoinhibition of Photosystem II Under Envrionmental Stress", Biochimica et Biophysica Acta, 1767: 414-421, 2007.

Ragauskas et al. "The Path Forward for Biofuels and Biomaterials", Science, 311: 484-489, Jan. 27, 2006.

Takahashi et al. "Repair Machinery of Symbiotic Photosynthesis as the Primary Target of Heat Stress for Reef-Building Corals", Plant Cell Physiology, 45(2): 251-255, 2004.

Wraight "Proton and Electron Transfer in the Acceptor Quinone Complex of Photosynthetic Reaction Centers From *Rhodobacter* Sphaeroides", Frontiers in Bioscience, 9: 309-337, Jan. 1, 2004.

Yamasaki et al. "Temperature Acclimation of Photosynthesis and Related Changes in Photosystem II Electron Transport in Winter Wheat", Plant Physiology, 128: 1087-1097, Mar. 2002.

Communication Pursuant to Article 94(3) EPC Dated Nov. 25, 2011 From the European Patent Office Re.: Application No. 07789975.5.

Communication Pursuant to Article 94(3) EPC Dated Mar. 29, 2010 From the European Patent Office Re.: Application No. 07789975.5.

Communication Pursuant to Article 94(3) EPC Dated Aug. 12, 2013 From the European Patent Office Re.: Application No. 07789975.5.

Motoki et al. "RecName: Full=Photosystem Q(8) Protein 1; EC=1.10.3.9; AltName: Full=32 kDa Thylakoid Membrane Protein 1; AltName: Full=Photosystcm II Protein D1 1", UNIPROT Database [Online], UniProt/Swiss-Prot Accession No. P0A445, Mar. 14, 2005.

* cited by examiner

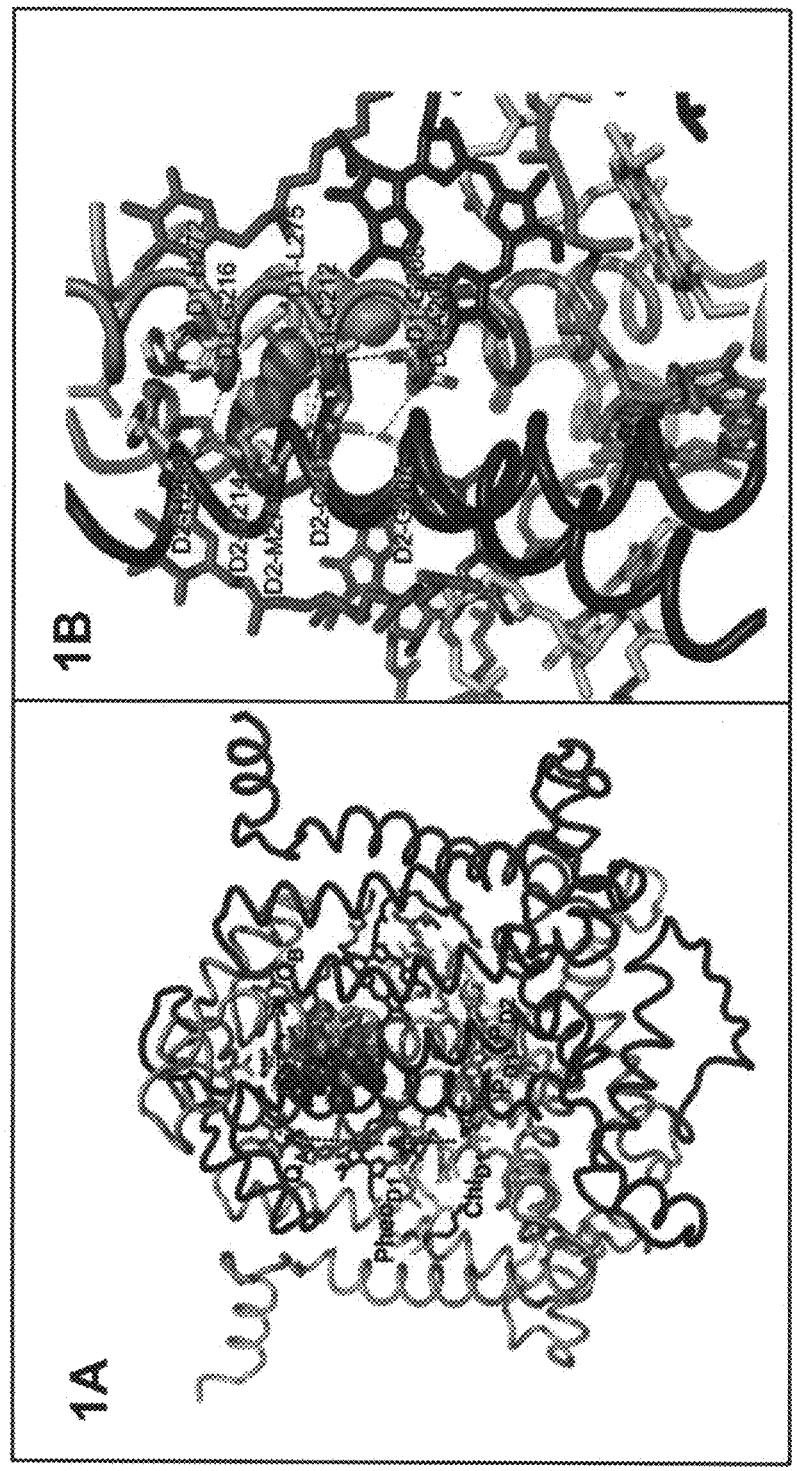
Figures 1A-B

Figure 1C

| | | | |
|---|---|---|---|
| L RCEL_RHOSH | 178 | SFFFTNALALALHGA | SEQ ID NO: 11 |
| L RCEL_RHOVI | 178 | SFLFVNAMALGLHGG | SEQ ID NO: 12 |
| L RCEL_CHLAU | 218 | TGLFASTWLLACHGS | SEQ ID NO: 13 |
| D1 PSBA1_SYNVU | 203 | AGVFGGALFCAMHGS | SEQ ID NO: 14 |
| D1 PSB2_SYNEL | 203 | AGVFGGALFAAMHGS | SEQ ID NO: 15 |
| D1 PSB2_SYNY3 | 203 | AGVFGGSLFSAMHGS | SEQ ID NO: 16 |
| D1 PSBA_CYACA | 203 | AGVFGGALFSAMHGS | SEQ ID NO: 17 |
| D1 PSBA_CHLRE | 203 | AGVFGGSLFSAMHGS | SEQ ID NO: 18 |
| D1 PSBA_SPIOL | 203 | AGVFGGSLFSAMHGS | SEQ ID NO: 19 |
| D1 PSBA_VIGUN | 203 | AGVFGGSLFSAMHGS | SEQ ID NO: 20 |
| D2 1s51_d | 202 | AGVLGGALLCAIHGA | SEQ ID NO: 21 |
| D2 NP_681245 | 202 | AGVLGGALLCAIHGA | SEQ ID NO: 22 |
| D2 PSBD_SYNY3 | 202 | AGILGGALLCAIHGA | SEQ ID NO: 23 |
| D2 PSBD_CYACA | 202 | AGILGGALLCAIHGA | SEQ ID NO: 24 |
| D2 PSBD_CHLRE | 201 | AGILGGALLCAIHGA | SEQ ID NO: 25 |
| D2 PSBD_SPIOL | 203 | AGVLGALLCAIHGA | SEQ ID NO: 26 |
| M RCEM_RHOVI | 205 | GFAYGCLLFAAHGA | SEQ ID NO: 27 |
| M RCEM_RHOSH | 207 | AFLYGSALLFAMHGA | SEQ ID NO: 28 |
| M RCEM_CHLAU | 197 | FFLLGSTWLLAMHAG | SEQ ID NO: 29 |

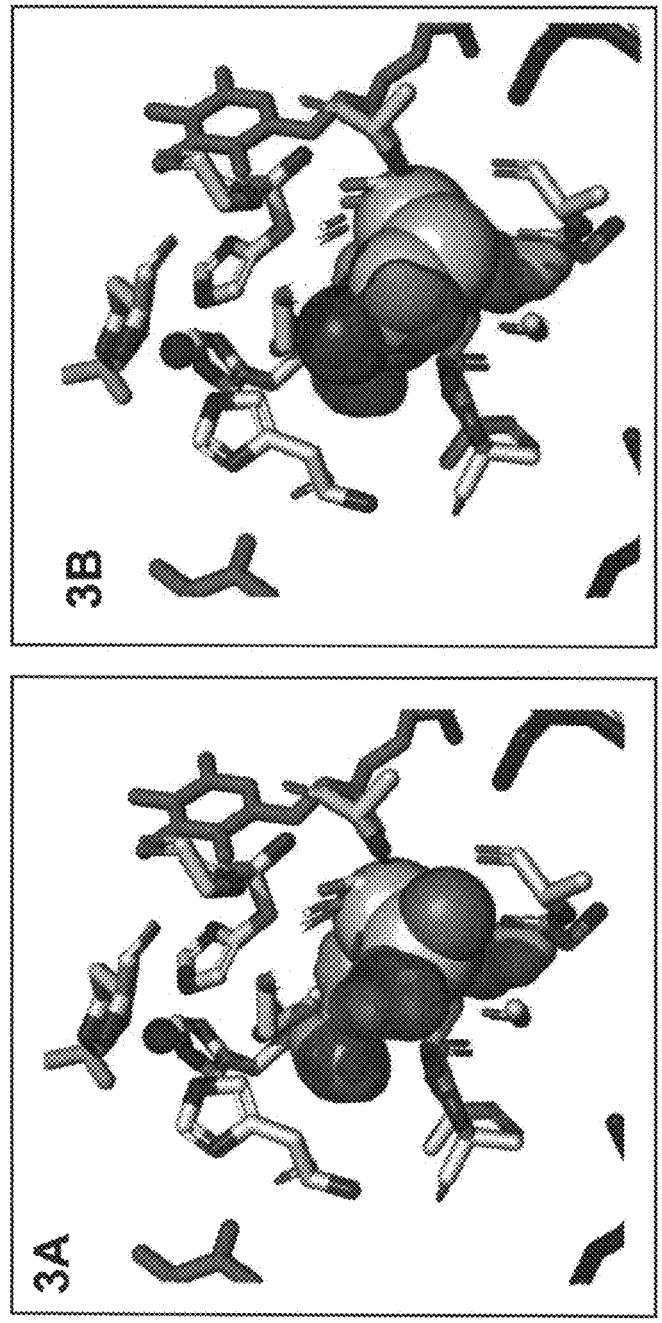
Figures 3A-B

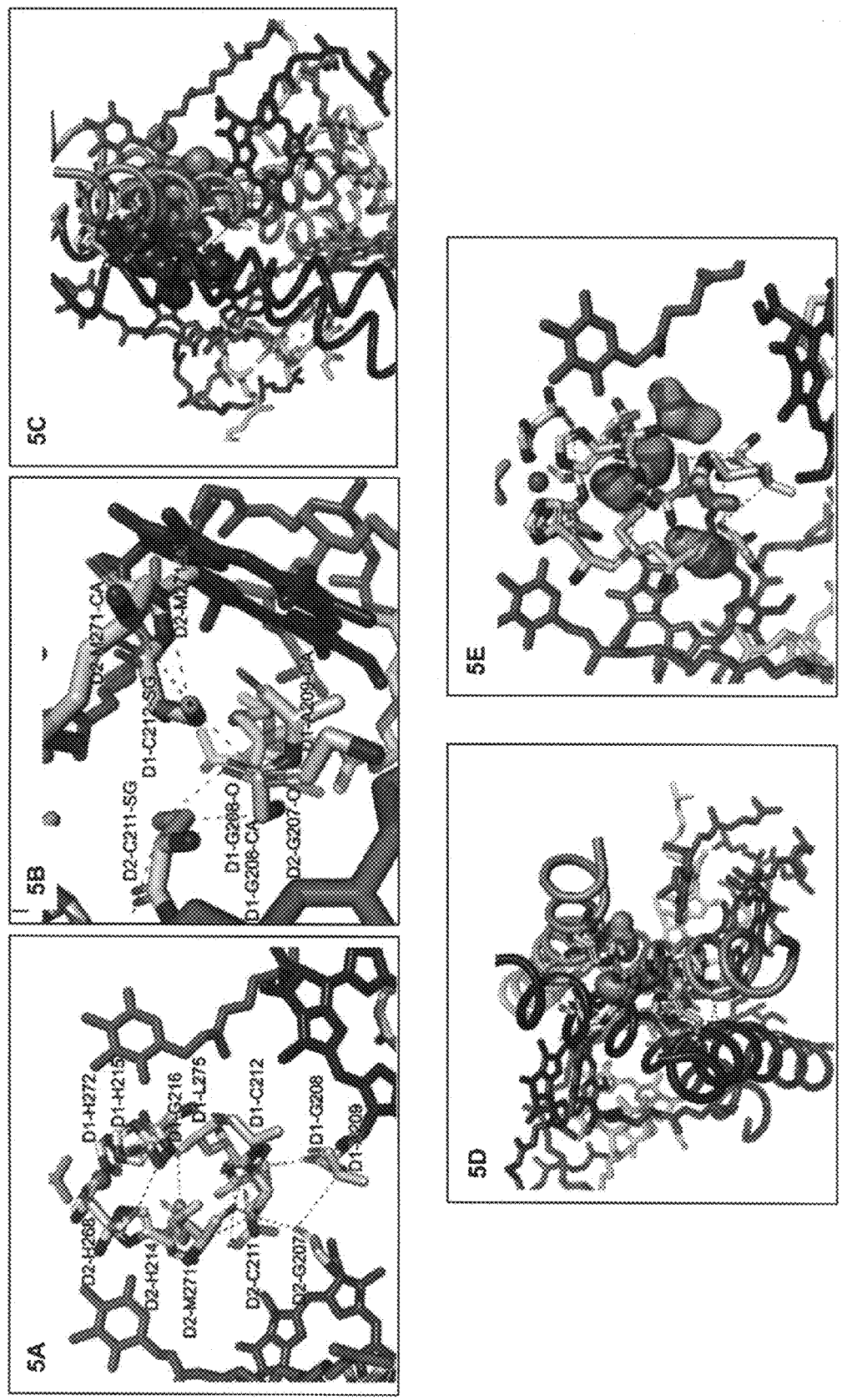
Figures 5A-E

30 °C

ΔKS  AA  P₂₁₂  AC  C₂₁₂

43 °C

ΔKS  AA  P₂₁₂  AC  C₂₁₂

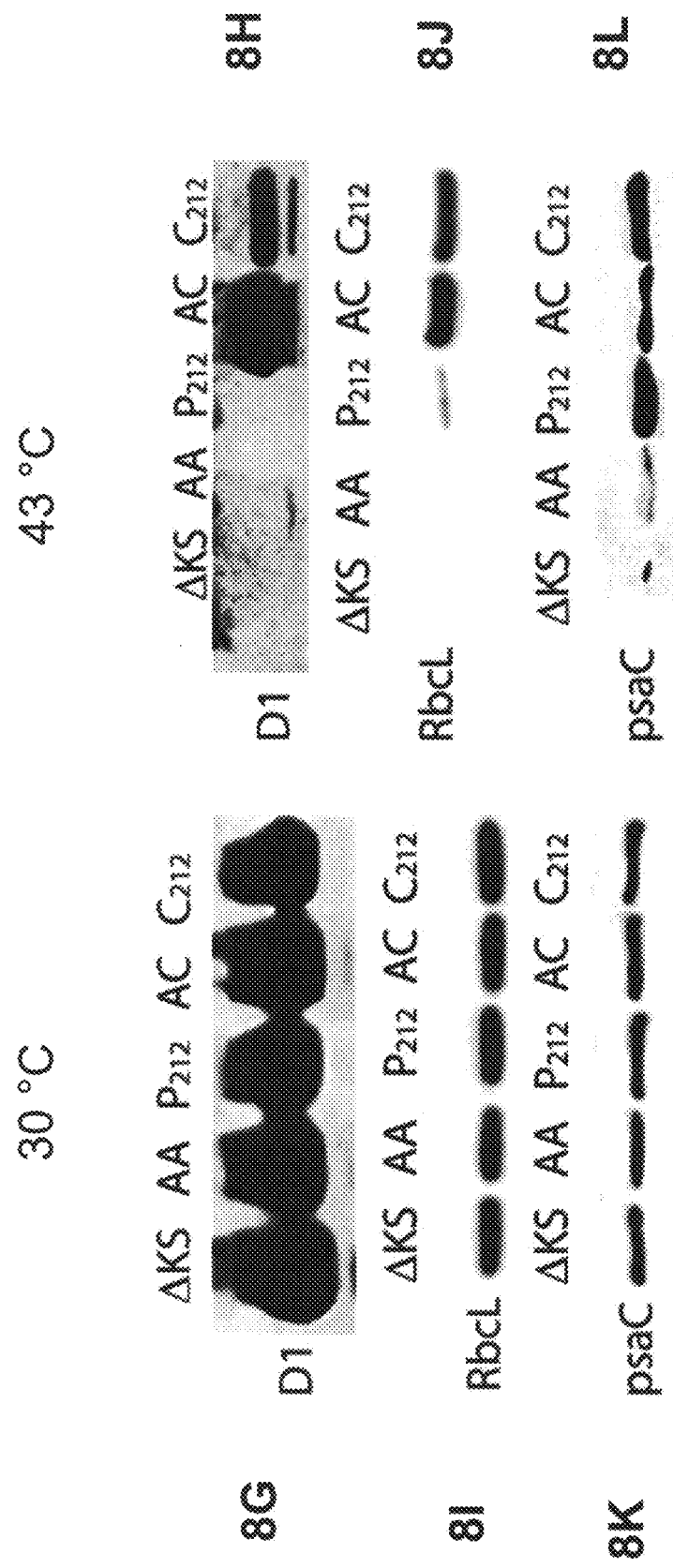
Figures 8G-L

Plasticity test 43 °C – 30 °C – 43 °C

Plasticity test 43 °C – 10 °C – 43 °C

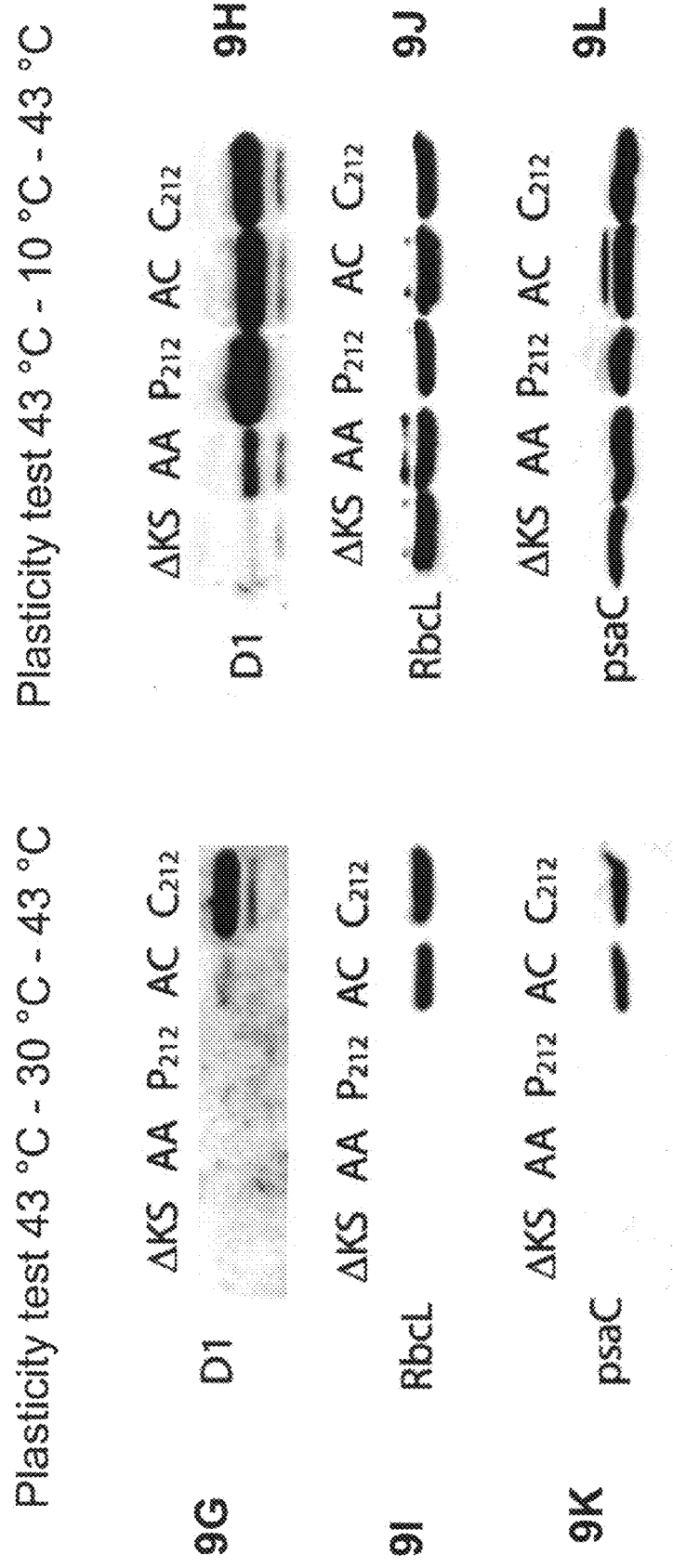
Figures 9G-L

SEQUENCE LISTING

```
<160> NUMBER OF SEQ ID NOS: 61

<210> SEQ ID NO 1
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 1
```

```
cggtggtagc ttgttcydbg ccatgcatgg ttcc                              34

<210> SEQ ID NO 2
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 2
cggtggtagc ttgttcvhwg ccatgcatgg ttcc                              34

<210> SEQ ID NO 3
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 3
gaacaagcta ccaccgaata caccagc                                     27

<210> SEQ ID NO 4
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 4
ggattaattc tctagactct ctaatgg                                     27

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 5
ccaaaacgcc ctctgtttac c                                           21

<210> SEQ ID NO 6
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 6
gccgtgggcg gcaacgatgt tgtagg                                      26

<210> SEQ ID NO 7
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 7
cttccacatg ttaggtgt                                               18

<210> SEQ ID NO 8
<211> LENGTH: 27
<212> TYPE: DNA
<213> ORGANISM: Artificial sequence
<220> FEATURE:
```

-continued

```
<223> OTHER INFORMATION: Single strand DNA oligonucleotide

<400> SEQUENCE: 8
accaccgaat acaccagcca cacctaa                                          27

<210> SEQ ID NO 9
<211> LENGTH: 34
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (17)..(19)
<223> OTHER INFORMATION: The nnn represents specific codons for Trp
      (TGG), Tyr (TAC), Phe (TTT), Arg (CGG), Gln (CAA), Glu (GAA), His
      (CAC), Asp (GAT), Lys (AAA), Gly (GGT) or Met (ATG)

<400> SEQUENCE: 9
cggtggtagc ttgttcnnng ccatgcatgg ttcc                                  34

<210> SEQ ID NO 10
<211> LENGTH: 42
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 10
ggtgtattcg gtggtnnstt gttcnnsgcc atgcatggtt cc                         42

<210> SEQ ID NO 11
<211> LENGTH: 15
<212> TYPE: PRT
<213> ORGANISM: Rhodopseudomonas sp.

<400> SEQUENCE: 11

Ser Phe Phe Phe Thr Asn Ala Leu Ala Leu Ala Leu His Gly Ala
1               5                   10                  15

<210> SEQ ID NO 12
<211> LENGTH: 15
<212> TYPE: PRT
<213> ORGANISM: Rhodopseudomonas sp.

<400> SEQUENCE: 12

Ser Phe Leu Phe Val Asn Ala Met Ala Leu Gly Leu His Gly Gly
1               5                   10                  15

<210> SEQ ID NO 13
<211> LENGTH: 15
<212> TYPE: PRT
<213> ORGANISM: Chloroflexus aurantiacus

<400> SEQUENCE: 13

Thr Gly Leu Phe Ala Ser Thr Trp Leu Leu Ala Cys His Gly Ser
1               5                   10                  15

<210> SEQ ID NO 14
<211> LENGTH: 15
```

```
<212> TYPE: PRT
<213> ORGANISM: Synechococcus vulcanus

<400> SEQUENCE: 14

Ala Gly Val Phe Gly Gly Ala Leu Phe Cys Ala Met His Gly Ser
1               5                   10                  15

<210> SEQ ID NO 15
<211> LENGTH: 15
<212> TYPE: PRT
<213> ORGANISM: Synechococcus elongatus

<400> SEQUENCE: 15

Ala Gly Val Phe Gly Gly Ala Leu Phe Ala Ala Met His Gly Ser
1               5                   10                  15

<210> SEQ ID NO 16
<211> LENGTH: 15
<212> TYPE: PRT
<213> ORGANISM: Synechocystis sp.

<400> SEQUENCE: 16

Ala Gly Val Phe Gly Gly Ser Leu Phe Ser Ala Met His Gly Ser
1               5                   10                  15

<210> SEQ ID NO 17
<211> LENGTH: 15
<212> TYPE: PRT
<213> ORGANISM: Cyanidium caldarium

<400> SEQUENCE: 17

Ala Gly Val Phe Gly Gly Ala Leu Phe Ser Ala Met His Gly Ser
1               5                   10                  15

<210> SEQ ID NO 18
<211> LENGTH: 15
<212> TYPE: PRT
<213> ORGANISM: Chlamydomonas reinhardtii

<400> SEQUENCE: 18

Ala Gly Val Phe Gly Gly Ser Leu Phe Ser Ala Met His Gly Ser
1               5                   10                  15

<210> SEQ ID NO 19
<211> LENGTH: 15
<212> TYPE: PRT
<213> ORGANISM: Spinacia oleracea

<400> SEQUENCE: 19

Ala Gly Val Phe Gly Gly Ser Leu Phe Ser Ala Met His Gly Ser
1               5                   10                  15

<210> SEQ ID NO 20
<211> LENGTH: 15
<212> TYPE: PRT
<213> ORGANISM: Vigna unguiculata

<400> SEQUENCE: 20

Ala Gly Val Phe Gly Ser Ser Leu Phe Ser Ala Met His Gly Ser
1               5                   10                  15

<210> SEQ ID NO 21
<211> LENGTH: 15
<212> TYPE: PRT
<213> ORGANISM: Thermosynechococcus Elongatus
```

-continued

```
<400> SEQUENCE: 21

Ala Gly Val Leu Gly Gly Ala Leu Leu Cys Ala Ile His Gly Ala
1               5                   10                  15

<210> SEQ ID NO 22
<211> LENGTH: 15
<212> TYPE: PRT
<213> ORGANISM: Thermosynechococcus elongatus

<400> SEQUENCE: 22

Ala Gly Val Leu Gly Gly Ala Leu Leu Cys Ala Ile His Gly Ala
1               5                   10                  15

<210> SEQ ID NO 23
<211> LENGTH: 15
<212> TYPE: PRT
<213> ORGANISM: Synechocystis sp.

<400> SEQUENCE: 23

Ala Gly Ile Leu Gly Gly Ala Leu Leu Cys Ala Ile His Gly Ala
1               5                   10                  15

<210> SEQ ID NO 24
<211> LENGTH: 15
<212> TYPE: PRT
<213> ORGANISM: Cyanidium caldarium

<400> SEQUENCE: 24

Ala Gly Ile Leu Gly Gly Ala Leu Leu Cys Ala Ile His Gly Ala
1               5                   10                  15

<210> SEQ ID NO 25
<211> LENGTH: 15
<212> TYPE: PRT
<213> ORGANISM: Chlamydomonas reinhardtii

<400> SEQUENCE: 25

Ala Gly Val Leu Gly Ala Ala Leu Leu Cys Ala Ile His Gly Ala
1               5                   10                  15

<210> SEQ ID NO 26
<211> LENGTH: 15
<212> TYPE: PRT
<213> ORGANISM: Spinacia oleracea

<400> SEQUENCE: 26

Ala Gly Val Leu Gly Ala Ala Leu Leu Cys Ala Ile His Gly Ala
1               5                   10                  15

<210> SEQ ID NO 27
<211> LENGTH: 15
<212> TYPE: PRT
<213> ORGANISM: Rhodopseudomonas viridis

<400> SEQUENCE: 27

Gly Phe Ala Tyr Gly Cys Gly Leu Leu Phe Ala Ala His Gly Ala
1               5                   10                  15

<210> SEQ ID NO 28
<211> LENGTH: 15
<212> TYPE: PRT
<213> ORGANISM: Rhodobacter sphaeroides

<400> SEQUENCE: 28

Ala Phe Leu Tyr Gly Ser Ala Leu Leu Phe Ala Met His Gly Ala
```

-continued

<210> SEQ ID NO 29
<211> LENGTH: 15
<212> TYPE: PRT
<213> ORGANISM: Chloroflexus aurantiacus

<400> SEQUENCE: 29

Phe Phe Leu Leu Gly Ser Thr Leu Leu Ala Met His Ala Gly
1               5                   10                  15

<210> SEQ ID NO 30
<211> LENGTH: 352
<212> TYPE: PRT
<213> ORGANISM: Synechocystis sp.

<400> SEQUENCE: 30

Met Thr Ile Ala Val Gly Arg Ala Pro Val Glu Arg Gly Trp Phe Asp
1               5                   10                  15

Val Leu Asp Asp Trp Leu Lys Arg Asp Arg Phe Val Phe Ile Gly Trp
                20                  25                  30

Ser Gly Leu Leu Leu Phe Pro Cys Ala Phe Met Ala Leu Gly Gly Trp
            35                  40                  45

Leu Thr Gly Thr Thr Phe Val Thr Ser Trp Tyr Thr His Gly Leu Ala
        50                  55                  60

Ser Ser Tyr Leu Glu Gly Ala Asn Phe Leu Thr Val Ala Val Ser Ser
65                  70                  75                  80

Pro Ala Asp Ala Phe Gly His Ser Leu Leu Phe Leu Trp Gly Pro Glu
                85                  90                  95

Ala Gln Gly Asn Leu Thr Arg Trp Phe Gln Ile Gly Gly Leu Trp Pro
            100                 105                 110

Phe Val Ala Leu His Gly Ala Phe Gly Leu Ile Gly Phe Met Leu Arg
        115                 120                 125

Gln Phe Glu Ile Ser Arg Leu Val Gly Ile Arg Pro Tyr Asn Ala Ile
130                 135                 140

Ala Phe Ser Gly Pro Ile Ala Val Phe Val Ser Val Phe Leu Met Tyr
145                 150                 155                 160

Pro Leu Gly Gln Ser Ser Trp Phe Phe Ala Pro Ser Phe Gly Val Ala
                165                 170                 175

Gly Ile Phe Arg Phe Ile Leu Phe Leu Gln Gly Phe His Asn Trp Thr
            180                 185                 190

Leu Asn Pro Phe His Met Met Gly Val Ala Gly Ile Leu Gly Gly Ala
        195                 200                 205

Leu Leu Cys Ala Ile His Gly Ala Thr Val Glu Asn Thr Leu Phe Glu
    210                 215                 220

Asp Gly Glu Asp Ser Asn Thr Phe Arg Ala Phe Glu Pro Thr Gln Ala
225                 230                 235                 240

Glu Glu Thr Tyr Ser Met Val Thr Ala Asn Arg Phe Trp Ser Gln Ile
                245                 250                 255

Phe Gly Ile Ala Phe Ser Asn Lys Arg Trp Leu His Phe Phe Met Leu
            260                 265                 270

Phe Val Pro Val Thr Gly Leu Trp Met Ser Ser Val Gly Ile Val Gly
        275                 280                 285

Leu Ala Leu Asn Leu Arg Ala Tyr Asp Phe Val Ser Gln Glu Leu Arg
    290                 295                 300

Ala Ala Glu Asp Pro Glu Phe Glu Thr Phe Tyr Thr Lys Asn Ile Leu
305                 310                 315                 320

Leu Asn Glu Gly Met Arg Ala Trp Met Ala Pro Gln Asp Gln Pro His
            325                 330                 335

Glu Asn Phe Ile Phe Pro Glu Val Leu Pro Arg Gly Asn Ala Leu
            340                 345                 350

<210> SEQ ID NO 31
<211> LENGTH: 324
<212> TYPE: PRT
<213> ORGANISM: Rhodopseudomonas viridis

<400> SEQUENCE: 31

Met Ala Asp Tyr Gln Thr Ile Tyr Thr Gln Ile Gln Ala Arg Gly Pro
1               5                   10                  15

His Ile Thr Val Ser Gly Glu Trp Gly Asp Asn Asp Arg Val Gly Lys
            20                  25                  30

Pro Phe Tyr Ser Tyr Trp Leu Gly Lys Ile Gly Asp Ala Gln Ile Gly
        35                  40                  45

Pro Ile Tyr Leu Gly Ala Ser Gly Ile Ala Ala Phe Ala Phe Gly Ser
    50                  55                  60

Thr Ala Ile Leu Ile Ile Leu Phe Asn Met Ala Ala Glu Val His Phe
65                  70                  75                  80

Asp Pro Leu Gln Phe Phe Arg Gln Phe Phe Trp Leu Gly Leu Tyr Pro
                85                  90                  95

Pro Lys Ala Gln Tyr Gly Met Gly Ile Pro Pro Leu His Asp Gly Gly
            100                 105                 110

Trp Trp Leu Met Ala Gly Leu Phe Met Thr Leu Ser Leu Gly Ser Trp
        115                 120                 125

Trp Ile Arg Val Tyr Ser Arg Ala Arg Ala Leu Gly Leu Gly Thr His
    130                 135                 140

Ile Ala Trp Asn Phe Ala Ala Ala Ile Phe Phe Val Leu Cys Ile Gly
145                 150                 155                 160

Cys Ile His Pro Thr Leu Val Gly Ser Trp Ser Glu Gly Val Pro Phe
                165                 170                 175

Gly Ile Trp Pro His Ile Asp Trp Leu Thr Ala Phe Ser Ile Arg Tyr
            180                 185                 190

Gly Asn Phe Tyr Tyr Cys Pro Trp His Gly Phe Ser Ile Gly Phe Ala
        195                 200                 205

Tyr Gly Cys Gly Leu Leu Phe Ala Ala His Gly Ala Thr Ile Leu Ala
    210                 215                 220

Val Ala Arg Phe Gly Gly Asp Arg Glu Ile Glu Gln Ile Thr Asp Arg
225                 230                 235                 240

Gly Thr Ala Val Glu Arg Ala Ala Leu Phe Trp Arg Trp Thr Ile Gly
                245                 250                 255

Phe Asn Ala Thr Ile Glu Ser Val His Arg Trp Gly Trp Phe Phe Ser
            260                 265                 270

Leu Met Val Met Val Ser Ala Ser Val Gly Ile Leu Leu Thr Gly Thr
        275                 280                 285

Phe Val Asp Asn Trp Tyr Leu Trp Cys Val Lys His Gly Ala Ala Pro
    290                 295                 300

Asp Tyr Pro Ala Tyr Leu Pro Ala Thr Pro Asp Pro Ala Ser Leu Pro
305                 310                 315                 320

Gly Ala Pro Lys

<210> SEQ ID NO 32
<211> LENGTH: 308

```
<212> TYPE: PRT
<213> ORGANISM: Rhodopseudomonas spaeroides

<400> SEQUENCE: 32

Met Ala Glu Tyr Gln Asn Ile Phe Ser Gln Val Gln Val Arg Gly Pro
1               5                   10                  15

Ala Asp Leu Gly Met Thr Glu Asp Val Asn Leu Ala Asn Arg Ser Gly
            20                  25                  30

Val Gly Pro Phe Ser Thr Leu Leu Gly Trp Phe Gly Asn Ala Gln Leu
        35                  40                  45

Gly Pro Ile Tyr Leu Gly Ser Leu Gly Val Leu Ser Leu Phe Ser Gly
    50                  55                  60

Leu Met Trp Phe Phe Thr Ile Gly Ile Trp Phe Trp Tyr Gln Ala Gly
65                  70                  75                  80

Trp Asn Pro Ala Val Phe Leu Arg Asp Leu Phe Phe Ser Leu Glu
                85                  90                  95

Pro Pro Ala Pro Glu Tyr Gly Leu Ser Phe Ala Ala Pro Leu Lys Glu
            100                 105                 110

Gly Gly Leu Trp Leu Ile Ala Ser Phe Phe Met Phe Val Ala Val Trp
        115                 120                 125

Ser Trp Trp Gly Arg Thr Tyr Leu Arg Ala Gln Ala Leu Gly Met Gly
    130                 135                 140

Lys His Thr Ala Trp Ala Phe Leu Ser Ala Ile Trp Leu Trp Met Val
145                 150                 155                 160

Leu Gly Phe Ile Arg Pro Ile Leu Met Gly Ser Trp Ser Glu Ala Val
                165                 170                 175

Pro Tyr Gly Ile Phe Ser His Leu Asp Trp Thr Asn Asn Phe Ser Leu
            180                 185                 190

Val His Gly Asn Leu Phe Tyr Asn Pro Phe His Gly Leu Ser Ile Ala
        195                 200                 205

Phe Leu Tyr Gly Ser Ala Leu Leu Phe Ala Met His Gly Ala Thr Ile
    210                 215                 220

Leu Ala Val Ser Arg Phe Gly Gly Glu Arg Glu Leu Glu Gln Ile Ala
225                 230                 235                 240

Asp Arg Gly Thr Ala Ala Glu Arg Ala Ala Leu Phe Trp Arg Trp Thr
                245                 250                 255

Met Gly Phe Asn Ala Thr Met Glu Gly Ile His Arg Trp Ala Ile Trp
            260                 265                 270

Met Ala Val Leu Val Thr Leu Thr Gly Gly Ile Gly Ile Leu Leu Ser
        275                 280                 285

Gly Thr Val Val Asp Asn Trp Tyr Val Trp Gly Gln Asn His Gly Met
    290                 295                 300

Ala Pro Leu Asn
305

<210> SEQ ID NO 33
<211> LENGTH: 282
<212> TYPE: PRT
<213> ORGANISM: Rhodopseudomonas spaeroides

<400> SEQUENCE: 33

Met Ala Leu Leu Ser Phe Glu Arg Lys Tyr Arg Val Pro Gly Gly Thr
1               5                   10                  15

Leu Val Gly Gly Asn Leu Phe Asp Phe Trp Val Gly Pro Phe Tyr Val
            20                  25                  30

Gly Phe Phe Gly Val Ala Thr Phe Phe Phe Ala Ala Leu Gly Ile Ile
```

```
                35                  40                  45
Leu Ile Ala Trp Ser Ala Val Leu Gln Gly Thr Trp Asn Pro Gln Leu
 50                  55                  60

Ile Ser Val Tyr Pro Pro Ala Leu Glu Tyr Gly Leu Gly Gly Ala Pro
 65                  70                  75                  80

Leu Ala Lys Gly Gly Leu Trp Gln Ile Ile Thr Ile Cys Ala Thr Gly
                 85                  90                  95

Ala Phe Val Ser Trp Ala Leu Arg Glu Val Glu Ile Cys Arg Lys Leu
                100                 105                 110

Gly Ile Gly Tyr His Ile Pro Phe Ala Phe Ala Phe Ala Ile Leu Ala
                115                 120                 125

Tyr Leu Thr Leu Val Leu Phe Arg Pro Val Met Met Gly Ala Trp Gly
130                 135                 140

Tyr Ala Phe Pro Tyr Gly Ile Trp Thr His Leu Asp Trp Val Ser Asn
145                 150                 155                 160

Thr Gly Tyr Thr Tyr Gly Asn Phe His Tyr Asn Pro Ala His Met Ile
                165                 170                 175

Ala Ile Ser Phe Phe Phe Thr Asn Ala Leu Ala Leu Ala Leu His Gly
                180                 185                 190

Ala Leu Val Leu Ser Ala Ala Asn Pro Glu Lys Gly Lys Glu Met Arg
                195                 200                 205

Thr Pro Asp His Glu Asp Thr Phe Phe Arg Asp Leu Val Gly Tyr Ser
210                 215                 220

Ile Gly Thr Leu Gly Ile His Arg Leu Gly Leu Leu Leu Ser Leu Ser
225                 230                 235                 240

Ala Val Phe Phe Ser Ala Leu Cys Met Ile Ile Thr Gly Thr Ile Trp
                245                 250                 255

Phe Asp Gln Trp Val Asp Trp Trp Gln Trp Trp Val Lys Leu Pro Trp
                260                 265                 270

Trp Ala Asn Ile Pro Gly Gly Ile Asn Gly
                275                 280

<210> SEQ ID NO 34
<211> LENGTH: 274
<212> TYPE: PRT
<213> ORGANISM: Rhodopseudomonas viridis

<400> SEQUENCE: 34

Met Ala Leu Leu Ser Phe Glu Arg Lys Tyr Arg Val Arg Gly Gly Thr
 1               5                  10                  15

Leu Ile Gly Gly Asp Leu Phe Asp Phe Trp Val Gly Pro Tyr Phe Val
                20                  25                  30

Gly Phe Phe Gly Val Ser Ala Ile Phe Phe Ile Phe Leu Gly Val Ser
                35                  40                  45

Leu Ile Gly Tyr Ala Ala Ser Gln Gly Pro Thr Trp Asp Pro Phe Ala
 50                  55                  60

Ile Ser Ile Asn Pro Pro Asp Leu Lys Tyr Gly Leu Gly Ala Ala Pro
 65                  70                  75                  80

Leu Leu Glu Gly Gly Phe Trp Gln Ala Ile Thr Val Cys Ala Leu Gly
                 85                  90                  95

Ala Phe Ile Ser Trp Met Leu Arg Glu Val Glu Ile Ser Arg Lys Leu
                100                 105                 110

Gly Ile Gly Trp His Val Pro Leu Ala Phe Cys Val Pro Ile Phe Met
                115                 120                 125

Phe Cys Val Leu Gln Val Phe Arg Pro Leu Leu Leu Gly Ser Trp Gly
```

```
                    130                 135                 140
His Ala Phe Pro Tyr Gly Ile Leu Ser His Leu Asp Trp Val Asn Asn
145                 150                 155                 160

Phe Gly Tyr Gln Tyr Leu Asn Trp His Tyr Asn Pro Gly His Met Ser
                165                 170                 175

Ser Val Ser Phe Leu Phe Val Asn Ala Met Ala Leu Gly Leu His Gly
            180                 185                 190

Gly Leu Ile Leu Ser Val Ala Asn Pro Gly Asp Gly Asp Lys Val Lys
        195                 200                 205

Thr Ala Glu His Glu Asn Gln Tyr Phe Arg Asp Val Val Gly Tyr Ser
    210                 215                 220

Ile Gly Ala Leu Ser Ile His Arg Leu Gly Leu Phe Leu Ala Ser Asn
225                 230                 235                 240

Ile Phe Leu Thr Gly Ala Phe Gly Thr Ile Ala Ser Gly Pro Phe Trp
                245                 250                 255

Thr Arg Gly Trp Pro Glu Trp Trp Gly Trp Trp Leu Asp Ile Pro Phe
            260                 265                 270

Trp Ser
```

<210> SEQ ID NO 35
<211> LENGTH: 1083
<212> TYPE: DNA
<213> ORGANISM: Synechocystis sp.

<400> SEQUENCE: 35

```
atgacaacga ctctccaaca gcgcgaaagc gcttccttgt gggaacagtt ttgtcagtgg      60
gtgacctcta ccaacaaccg gatttatgtc ggttggttcg gtaccttgat gatccccacc     120
ctcttaactg ccaccacttg cttcatcatt gccttcatcg ccgctccccc cgttgacatc     180
gacggtatcc gtgagcccgt tgctggttct ttgctttacg gtaacaacat catctctggt     240
gctgttgtac cttcttccaa cgctatcggt ttgcacttct accccatctg ggaagccgct     300
tccttagatg agtggttgta caacggtggt ccttaccagt tggtagtatt ccacttcctc     360
atcggcattt tctgctacat gggtcgtcag tgggaacttt cctaccgctt aggtatgcgt     420
ccttggattt gtgtggctta ctctgccccc gtatccgctg ccaccgccgt attcttgatc     480
taccccattg gtcaaggctc cttctctgat ggtatgccct gggtatttc tggtaccttc     540
aacttcatga tcgtgttcca agctgagcac aacatcctga tgcaccccct tccacatgtta     600
ggtgtggctg gtgtattcgg tggtagcttg ttctccgcca tgcacggttc cttggtaacc     660
tcctccttgg tgcgtgaaac caccgaagtt gaatcccaga actacggtta caaattcggt     720
caagaagaag aaacctacaa catcgttgcc gcccacggct actttggtcg gttgatcttc     780
caatatgctt ctttcaacaa cagccgttcc ttgcacttct tcttgggtgc ttggcctgta     840
atcggcatct ggtcactgc tatgggtgta agcaccatgg cgttcaacct gaacggtttc     900
aacttcaacc agtccatctt ggatagccaa ggccgggtaa tcggcacctg gctgatgta      960
ttgaaccgag ccaacatcgg ttttgaagta atgcacgaac gcaatgccca caacttcccc    1020
ctcgacttag cgtctgggga gcaagctcct gtggctttga ccgctcctgc tgtcaacggt    1080
taa                                                                  1083
```

<210> SEQ ID NO 36
<211> LENGTH: 360
<212> TYPE: PRT
<213> ORGANISM: Synechocystis sp.

<400> SEQUENCE: 36

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Ser Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 37
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Cys 212 mutant

<400> SEQUENCE: 37

```
Met Thr Thr Thr Leu Gln Gln Arg Glu Ser Ala Ser Leu Trp Glu Gln
 1               5                  10                  15
Phe Cys Gln Trp Val Thr Ser Thr Asn Asn Arg Ile Tyr Val Gly Trp
             20                  25                  30
Phe Gly Thr Leu Met Ile Pro Thr Leu Leu Thr Ala Thr Thr Cys Phe
         35                  40                  45
Ile Ile Ala Phe Ile Ala Ala Pro Pro Val Asp Ile Asp Gly Ile Arg
 50                  55                  60
Glu Pro Val Ala Gly Ser Leu Leu Tyr Gly Asn Asn Ile Ile Ser Gly
 65                  70                  75                  80
Ala Val Val Pro Ser Ser Asn Ala Ile Gly Leu His Phe Tyr Pro Ile
                 85                  90                  95
Trp Glu Ala Ala Ser Leu Asp Glu Trp Leu Tyr Asn Gly Gly Pro Tyr
            100                 105                 110
Gln Leu Val Val Phe His Phe Leu Ile Gly Ile Phe Cys Tyr Met Gly
        115                 120                 125
Arg Gln Trp Glu Leu Ser Tyr Arg Leu Gly Met Arg Pro Trp Ile Cys
130                 135                 140
Val Ala Tyr Ser Ala Pro Val Ser Ala Ala Thr Ala Val Phe Leu Ile
145                 150                 155                 160
Tyr Pro Ile Gly Gln Gly Ser Phe Ser Asp Gly Met Pro Leu Gly Ile
                165                 170                 175
Ser Gly Thr Phe Asn Phe Met Ile Val Phe Gln Ala Glu His Asn Ile
            180                 185                 190
Leu Met His Pro Phe His Met Leu Gly Val Ala Gly Val Phe Gly Gly
        195                 200                 205
Ser Leu Phe Cys Ala Met His Gly Ser Leu Val Thr Ser Ser Leu Val
210                 215                 220
Arg Glu Thr Thr Glu Val Glu Ser Gln Asn Tyr Gly Tyr Lys Phe Gly
225                 230                 235                 240
Gln Glu Glu Glu Thr Tyr Asn Ile Val Ala Ala His Gly Tyr Phe Gly
                245                 250                 255
Arg Leu Ile Phe Gln Tyr Ala Ser Phe Asn Asn Ser Arg Ser Leu His
            260                 265                 270
Phe Phe Leu Gly Ala Trp Pro Val Ile Gly Ile Trp Phe Thr Ala Met
        275                 280                 285
Gly Val Ser Thr Met Ala Phe Asn Leu Asn Gly Phe Asn Phe Asn Gln
290                 295                 300
Ser Ile Leu Asp Ser Gln Gly Arg Val Ile Gly Thr Trp Ala Asp Val
305                 310                 315                 320
Leu Asn Arg Ala Asn Ile Gly Phe Glu Val Met His Glu Arg Asn Ala
                325                 330                 335
His Asn Phe Pro Leu Asp Leu Ala Ser Gly Glu Gln Ala Pro Val Ala
            340                 345                 350
Leu Thr Ala Pro Ala Val Asn Gly
        355                 360
```

<210> SEQ ID NO 38
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Pro 212 mutant

<400> SEQUENCE: 38

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Pro Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 39
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Ala 212 mutant

<400> SEQUENCE: 39

```
Met Thr Thr Thr Leu Gln Gln Arg Glu Ser Ala Ser Leu Trp Glu Gln
  1               5                  10                  15

Phe Cys Gln Trp Val Thr Ser Thr Asn Asn Arg Ile Tyr Val Gly Trp
                 20                  25                  30

Phe Gly Thr Leu Met Ile Pro Thr Leu Leu Thr Ala Thr Thr Cys Phe
             35                  40                  45

Ile Ile Ala Phe Ile Ala Ala Pro Pro Val Asp Ile Asp Gly Ile Arg
 50                      55                  60

Glu Pro Val Ala Gly Ser Leu Leu Tyr Gly Asn Asn Ile Ile Ser Gly
 65                  70                  75                  80

Ala Val Val Pro Ser Ser Asn Ala Ile Gly Leu His Phe Tyr Pro Ile
                 85                  90                  95

Trp Glu Ala Ala Ser Leu Asp Glu Trp Leu Tyr Asn Gly Gly Pro Tyr
                100                 105                 110

Gln Leu Val Val Phe His Phe Leu Ile Gly Ile Phe Cys Tyr Met Gly
            115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
                195                 200                 205

Ser Leu Phe Ala Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
            275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
                340                 345                 350

Leu Thr Ala Pro Ala Val Asn Gly
            355                 360
```

<210> SEQ ID NO 40
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Gly 212 mutant

<400> SEQUENCE: 40

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
                20                  25                  30

Phe Gly Thr Leu Met Ile Pro Thr Leu Leu Thr Ala Thr Thr Cys Phe
            35                  40                  45

Ile Ile Ala Phe Ile Ala Ala Pro Pro Val Asp Ile Asp Gly Ile Arg
50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Gly Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 41
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Thr 212 mutant

<400> SEQUENCE: 41

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Thr Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 42
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Val 212 mutant

```
<400> SEQUENCE: 42

Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
                20                  25                  30

Phe Gly Thr Leu Met Ile Pro Thr Leu Leu Thr Ala Thr Thr Cys Phe
            35                  40                  45

Ile Ile Ala Phe Ile Ala Ala Pro Pro Val Asp Ile Asp Gly Ile Arg
50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Val Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360

<210> SEQ ID NO 43
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Leu 212 mutant
```

<400> SEQUENCE: 43

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
    50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Leu Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 44
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Ile 212 mutant

<400> SEQUENCE: 44

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
    50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Ile Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360

<210> SEQ ID NO 45
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Asp 212 mutant
```

<400> SEQUENCE: 45

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
    50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
    130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Asn Ala Met His Gly Ser Leu Val Thr Ser Ser Leu Val
    210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
    290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360

<210> SEQ ID NO 46
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Gln 212 mutant
```

<400> SEQUENCE: 46

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
    50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Gln Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 47
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Asp 212 mutant

<400> SEQUENCE: 47

```
Met Thr Thr Thr Leu Gln Gln Arg Glu Ser Ala Ser Leu Trp Glu Gln
 1               5                  10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Asp Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 48
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Glu 212 mutant

<400> SEQUENCE: 48

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Ser Leu Phe Glu Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 49
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Gly 209 mutant

<400> SEQUENCE: 49

```
Met Thr Thr Thr Leu Gln Gln Arg Glu Ser Ala Ser Leu Trp Glu Gln
  1               5                  10                  15

Phe Cys Gln Trp Val Thr Ser Thr Asn Asn Arg Ile Tyr Val Gly Trp
             20                  25                  30

Phe Gly Thr Leu Met Ile Pro Thr Leu Leu Thr Ala Thr Thr Cys Phe
         35                  40                  45

Ile Ile Ala Phe Ile Ala Ala Pro Pro Val Asp Ile Asp Gly Ile Arg
 50                  55                  60

Glu Pro Val Ala Gly Ser Leu Leu Tyr Gly Asn Asn Ile Ile Ser Gly
 65                  70                  75                  80

Ala Val Val Pro Ser Ser Asn Ala Ile Gly Leu His Phe Tyr Pro Ile
                 85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
            115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
            195                 200                 205

Gly Leu Phe Ser Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
            275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
            355                 360
```

<210> SEQ ID NO 50
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Ala 209 mutant

<400> SEQUENCE: 50

```
Met Thr Thr Thr Leu Gln Gln Arg Glu Ser Ala Ser Leu Trp Glu Gln
  1               5                  10                  15

Phe Cys Gln Trp Val Thr Ser Thr Asn Asn Arg Ile Tyr Val Gly Trp
                 20                  25                  30

Phe Gly Thr Leu Met Ile Pro Thr Leu Leu Thr Ala Thr Thr Cys Phe
             35                  40                  45

Ile Ile Ala Phe Ile Ala Ala Pro Pro Val Asp Ile Asp Gly Ile Arg
 50                  55                  60

Glu Pro Val Ala Gly Ser Leu Leu Tyr Gly Asn Asn Ile Ile Ser Gly
 65                  70                  75                  80

Ala Val Val Pro Ser Ser Asn Ala Ile Gly Leu His Phe Tyr Pro Ile
                 85                  90                  95

Trp Glu Ala Ala Ser Leu Asp Glu Trp Leu Tyr Asn Gly Gly Pro Tyr
                100                 105                 110

Gln Leu Val Val Phe His Phe Leu Ile Gly Ile Phe Cys Tyr Met Gly
            115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
            195                 200                 205

Ala Leu Phe Ser Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
            275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
            355                 360
```

<210> SEQ ID NO 51
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Thr 209 mutant

<400> SEQUENCE: 51

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
    50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Thr Leu Phe Ser Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 52
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Pro 209 mutant

<400> SEQUENCE: 52

```
Met Thr Thr Thr Leu Gln Gln Arg Glu Ser Ala Ser Leu Trp Glu Gln
1               5                   10                  15

Phe Cys Gln Trp Val Thr Ser Thr Asn Asn Arg Ile Tyr Val Gly Trp
            20                  25                  30

Phe Gly Thr Leu Met Ile Pro Thr Leu Leu Thr Ala Thr Thr Cys Phe
        35                  40                  45

Ile Ile Ala Phe Ile Ala Ala Pro Pro Val Asp Ile Asp Gly Ile Arg
50                  55                  60

Glu Pro Val Ala Gly Ser Leu Leu Tyr Gly Asn Asn Ile Ile Ser Gly
65                  70                  75                  80

Ala Val Val Pro Ser Ser Asn Ala Ile Gly Leu His Phe Tyr Pro Ile
                85                  90                  95

Trp Glu Ala Ala Ser Leu Asp Glu Trp Leu Tyr Asn Gly Gly Pro Tyr
            100                 105                 110

Gln Leu Val Val Phe His Phe Leu Ile Gly Ile Phe Cys Tyr Met Gly
        115                 120                 125

Arg Gln Trp Glu Leu Ser Tyr Arg Leu Gly Met Arg Pro Trp Ile Cys
130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
            180                 185                 190

Leu Met His Pro Phe His Met Leu Gly Val Ala Gly Val Phe Gly Gly
        195                 200                 205

Pro Leu Phe Ser Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
            260                 265                 270

Phe Phe Leu Gly Ala Trp Pro Val Ile Gly Ile Trp Phe Thr Ala Met
        275                 280                 285

Gly Val Ser Thr Met Ala Phe Asn Leu Asn Gly Phe Asn Phe Asn Gln
290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
            340                 345                 350

Leu Thr Ala Pro Ala Val Asn Gly
        355                 360
```

<210> SEQ ID NO 53
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Val 209 mutant

<400> SEQUENCE: 53

| | | | | | | | | | | | | | | |
|---|---|---|---|---|---|---|---|---|---|---|---|---|---|---|
| Met | Thr | Thr | Thr | Leu | Gln | Gln | Arg | Glu | Ser | Ala | Ser | Leu | Trp | Glu | Gln |
| 1 | | | | 5 | | | | | 10 | | | | | 15 | |
| Phe | Cys | Gln | Trp | Val | Thr | Ser | Thr | Asn | Asn | Arg | Ile | Tyr | Val | Gly | Trp |
| | | | 20 | | | | | 25 | | | | | 30 | | |
| Phe | Gly | Thr | Leu | Met | Ile | Pro | Thr | Leu | Leu | Thr | Ala | Thr | Thr | Cys | Phe |
| | | | | 35 | | | | | 40 | | | | | 45 | |
| Ile | Ile | Ala | Phe | Ile | Ala | Ala | Pro | Pro | Val | Asp | Ile | Asp | Gly | Ile | Arg |
| | 50 | | | | | 55 | | | | | 60 | | | | |
| Glu | Pro | Val | Ala | Gly | Ser | Leu | Leu | Tyr | Gly | Asn | Asn | Ile | Ile | Ser | Gly |
| 65 | | | | | 70 | | | | | 75 | | | | | 80 |
| Ala | Val | Val | Pro | Ser | Ser | Asn | Ala | Ile | Gly | Leu | His | Phe | Tyr | Pro | Ile |
| | | | | 85 | | | | | 90 | | | | | 95 | |
| Trp | Glu | Ala | Ala | Ser | Leu | Asp | Glu | Trp | Leu | Tyr | Asn | Gly | Gly | Pro | Tyr |
| | | | | 100 | | | | | 105 | | | | | 110 | |
| Gln | Leu | Val | Val | Phe | His | Phe | Leu | Ile | Gly | Ile | Phe | Cys | Tyr | Met | Gly |
| | | | | 115 | | | | | 120 | | | | | 125 | |
| Arg | Gln | Trp | Glu | Leu | Ser | Tyr | Arg | Leu | Gly | Met | Arg | Pro | Trp | Ile | Cys |
| | 130 | | | | | 135 | | | | | 140 | | | | |
| Val | Ala | Tyr | Ser | Ala | Pro | Val | Ser | Ala | Ala | Thr | Ala | Val | Phe | Leu | Ile |
| 145 | | | | | 150 | | | | | 155 | | | | | 160 |
| Tyr | Pro | Ile | Gly | Gln | Gly | Ser | Phe | Ser | Asp | Gly | Met | Pro | Leu | Gly | Ile |
| | | | | 165 | | | | | 170 | | | | | 175 | |
| Ser | Gly | Thr | Phe | Asn | Phe | Met | Ile | Val | Phe | Gln | Ala | Glu | His | Asn | Ile |
| | | | 180 | | | | | 185 | | | | | 190 | | |
| Leu | Met | His | Pro | Phe | His | Met | Leu | Gly | Val | Ala | Gly | Val | Phe | Gly | Gly |
| | | | 195 | | | | | 200 | | | | | 205 | | |
| Val | Leu | Phe | Ser | Ala | Met | His | Gly | Ser | Leu | Val | Thr | Ser | Ser | Leu | Val |
| | 210 | | | | | 215 | | | | | 220 | | | | |
| Arg | Glu | Thr | Thr | Glu | Val | Glu | Ser | Gln | Asn | Tyr | Gly | Tyr | Lys | Phe | Gly |
| 225 | | | | | 230 | | | | | 235 | | | | | 240 |
| Gln | Glu | Glu | Glu | Thr | Tyr | Asn | Ile | Val | Ala | Ala | His | Gly | Tyr | Phe | Gly |
| | | | | 245 | | | | | 250 | | | | | 255 | |
| Arg | Leu | Ile | Phe | Gln | Tyr | Ala | Ser | Phe | Asn | Asn | Ser | Arg | Ser | Leu | His |
| | | | 260 | | | | | 265 | | | | | 270 | | |
| Phe | Phe | Leu | Gly | Ala | Trp | Pro | Val | Ile | Gly | Ile | Trp | Phe | Thr | Ala | Met |
| | | | 275 | | | | | 280 | | | | | 285 | | |
| Gly | Val | Ser | Thr | Met | Ala | Phe | Asn | Leu | Asn | Gly | Phe | Asn | Phe | Asn | Gln |
| | 290 | | | | | 295 | | | | | 300 | | | | |
| Ser | Ile | Leu | Asp | Ser | Gln | Gly | Arg | Val | Ile | Gly | Thr | Trp | Ala | Asp | Val |
| 305 | | | | | 310 | | | | | 315 | | | | | 320 |
| Leu | Asn | Arg | Ala | Asn | Ile | Gly | Phe | Glu | Val | Met | His | Glu | Arg | Asn | Ala |
| | | | | 325 | | | | | 330 | | | | | 335 | |
| His | Asn | Phe | Pro | Leu | Asp | Leu | Ala | Ser | Gly | Glu | Gln | Ala | Pro | Val | Ala |
| | | | | 340 | | | | | 345 | | | | | 350 | |
| Leu | Thr | Ala | Pro | Ala | Val | Asn | Gly |
| | | | | 355 | | | | | 360 |

<210> SEQ ID NO 54
<211> LENGTH: 360
<212> TYPE: PRT
<213> ORGANISM: Synechocystis sp.

<400> SEQUENCE: 54

| | | | | | | | | | | | | | | |
|---|---|---|---|---|---|---|---|---|---|---|---|---|---|---|
| Met | Thr | Thr | Thr | Leu | Gln | Gln | Arg | Glu | Ser | Ala | Ser | Leu | Trp | Glu | Gln |

```
            1               5                  10                 15
Phe Cys Gln Trp Val Thr Ser Thr Asn Asn Arg Ile Tyr Val Gly Trp
                 20                  25                  30

Phe Gly Thr Leu Met Ile Pro Thr Leu Leu Thr Ala Thr Thr Cys Phe
                 35                  40                  45

Ile Ile Ala Phe Ile Ala Ala Pro Val Asp Ile Asp Gly Ile Arg
 50                  55                  60

Glu Pro Val Ala Gly Ser Leu Leu Tyr Gly Asn Asn Ile Ile Ser Gly
 65                  70                  75                  80

Ala Val Val Pro Ser Ser Asn Ala Ile Gly Leu His Phe Tyr Pro Ile
                 85                  90                  95

Trp Glu Ala Ala Ser Leu Asp Glu Trp Leu Tyr Asn Gly Gly Pro Tyr
                100                 105                 110

Gln Leu Val Val Phe His Phe Leu Ile Gly Ile Phe Cys Tyr Met Gly
                115                 120                 125

Arg Gln Trp Glu Leu Ser Tyr Arg Leu Gly Met Arg Pro Trp Ile Cys
                130                 135                 140

Val Ala Tyr Ser Ala Pro Val Ser Ala Ala Thr Ala Val Phe Leu Ile
145                 150                 155                 160

Tyr Pro Ile Gly Gln Gly Ser Phe Ser Asp Gly Met Pro Leu Gly Ile
                165                 170                 175

Ser Gly Thr Phe Asn Phe Met Ile Val Phe Gln Ala Glu His Asn Ile
                180                 185                 190

Leu Met His Pro Phe His Met Leu Gly Val Ala Gly Val Phe Gly Gly
                195                 200                 205

Asn Leu Phe Ser Ala Met His Gly Ser Leu Val Thr Ser Ser Leu Val
210                 215                 220

Arg Glu Thr Thr Glu Val Glu Ser Gln Asn Tyr Gly Tyr Lys Phe Gly
225                 230                 235                 240

Gln Glu Glu Glu Thr Tyr Asn Ile Val Ala Ala His Gly Tyr Phe Gly
                245                 250                 255

Arg Leu Ile Phe Gln Tyr Ala Ser Phe Asn Asn Ser Arg Ser Leu His
                260                 265                 270

Phe Phe Leu Gly Ala Trp Pro Val Ile Gly Ile Trp Phe Thr Ala Met
                275                 280                 285

Gly Val Ser Thr Met Ala Phe Asn Leu Asn Gly Phe Asn Phe Asn Gln
                290                 295                 300

Ser Ile Leu Asp Ser Gln Gly Arg Val Ile Gly Thr Trp Ala Asp Val
305                 310                 315                 320

Leu Asn Arg Ala Asn Ile Gly Phe Glu Val Met His Glu Arg Asn Ala
                325                 330                 335

His Asn Phe Pro Leu Asp Leu Ala Ser Gly Glu Gln Ala Pro Val Ala
                340                 345                 350

Leu Thr Ala Pro Ala Val Asn Gly
                355                 360

<210> SEQ ID NO 55
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Asp 209 mutant

<400> SEQUENCE: 55

Met Thr Thr Leu Gln Gln Arg Glu Ser Ala Ser Leu Trp Glu Gln
```

```
                1               5                   10                  15
            Phe Cys Gln Trp Val Thr Ser Thr Asn Asn Arg Ile Tyr Val Gly Trp
                            20                  25                  30

Phe Gly Thr Leu Met Ile Pro Thr Leu Leu Thr Ala Thr Thr Cys Phe
                            35                  40                  45

Ile Ile Ala Phe Ile Ala Ala Pro Val Asp Ile Asp Gly Ile Arg
             50                  55                  60

Glu Pro Val Ala Gly Ser Leu Leu Tyr Gly Asn Asn Ile Ile Ser Gly
             65                  70                  75                  80

Ala Val Val Pro Ser Ser Asn Ala Ile Gly Leu His Phe Tyr Pro Ile
                            85                  90                  95

Trp Glu Ala Ala Ser Leu Asp Glu Trp Leu Tyr Asn Gly Gly Pro Tyr
                           100                 105                 110

Gln Leu Val Val Phe His Phe Leu Ile Gly Ile Phe Cys Tyr Met Gly
                           115                 120                 125

Arg Gln Trp Glu Leu Ser Tyr Arg Leu Gly Met Arg Pro Trp Ile Cys
                           130                 135                 140

Val Ala Tyr Ser Ala Pro Val Ser Ala Ala Thr Ala Val Phe Leu Ile
            145                 150                 155                 160

Tyr Pro Ile Gly Gln Gly Ser Phe Ser Asp Gly Met Pro Leu Gly Ile
                           165                 170                 175

Ser Gly Thr Phe Asn Phe Met Ile Val Phe Gln Ala Glu His Asn Ile
                           180                 185                 190

Leu Met His Pro Phe His Met Leu Gly Val Ala Gly Val Phe Gly Gly
                           195                 200                 205

Asp Leu Phe Ser Ala Met His Gly Ser Leu Val Thr Ser Ser Leu Val
                           210                 215                 220

Arg Glu Thr Thr Glu Val Glu Ser Gln Asn Tyr Gly Tyr Lys Phe Gly
            225                 230                 235                 240

Gln Glu Glu Glu Thr Tyr Asn Ile Val Ala Ala His Gly Tyr Phe Gly
                           245                 250                 255

Arg Leu Ile Phe Gln Tyr Ala Ser Phe Asn Asn Ser Arg Ser Leu His
                           260                 265                 270

Phe Phe Leu Gly Ala Trp Pro Val Ile Gly Ile Trp Phe Thr Ala Met
                           275                 280                 285

Gly Val Ser Thr Met Ala Phe Asn Leu Asn Gly Phe Asn Phe Asn Gln
                           290                 295                 300

Ser Ile Leu Asp Ser Gln Gly Arg Val Ile Gly Thr Trp Ala Asp Val
            305                 310                 315                 320

Leu Asn Arg Ala Asn Ile Gly Phe Glu Val Met His Glu Arg Asn Ala
                           325                 330                 335

His Asn Phe Pro Leu Asp Leu Ala Ser Gly Glu Gln Ala Pro Val Ala
                           340                 345                 350

Leu Thr Ala Pro Ala Val Asn Gly
                           355                 360

<210> SEQ ID NO 56
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Ala 209/Cys 212 mutant

<400> SEQUENCE: 56

Met Thr Thr Thr Leu Gln Gln Arg Glu Ser Ala Ser Leu Trp Glu Gln
```

```
            1               5                   10                  15
        Phe Cys Gln Trp Val Thr Ser Thr Asn Asn Arg Ile Tyr Val Gly Trp
                        20                  25                  30

Phe Gly Thr Leu Met Ile Pro Thr Leu Leu Thr Ala Thr Thr Cys Phe
                        35                  40                  45

Ile Ile Ala Phe Ile Ala Ala Pro Val Asp Ile Asp Gly Ile Arg
         50                  55                  60

Glu Pro Val Ala Gly Ser Leu Leu Tyr Gly Asn Asn Ile Ile Ser Gly
         65                  70                  75                  80

Ala Val Val Pro Ser Ser Asn Ala Ile Gly Leu His Phe Tyr Pro Ile
                        85                  90                  95

Trp Glu Ala Ala Ser Leu Asp Glu Trp Leu Tyr Asn Gly Gly Pro Tyr
                        100                 105                 110

Gln Leu Val Val Phe His Phe Leu Ile Gly Ile Phe Cys Tyr Met Gly
                        115                 120                 125

Arg Gln Trp Glu Leu Ser Tyr Arg Leu Gly Met Arg Pro Trp Ile Cys
                        130                 135                 140

Val Ala Tyr Ser Ala Pro Val Ser Ala Ala Thr Ala Val Phe Leu Ile
        145                 150                 155                 160

Tyr Pro Ile Gly Gln Gly Ser Phe Ser Asp Gly Met Pro Leu Gly Ile
                        165                 170                 175

Ser Gly Thr Phe Asn Phe Met Ile Val Phe Gln Ala Glu His Asn Ile
                        180                 185                 190

Leu Met His Pro Phe His Met Leu Gly Val Ala Gly Val Phe Gly Gly
                        195                 200                 205

Ala Leu Phe Cys Ala Met His Gly Ser Leu Val Thr Ser Ser Leu Val
                        210                 215                 220

Arg Glu Thr Thr Glu Val Glu Ser Gln Asn Tyr Gly Tyr Lys Phe Gly
        225                 230                 235                 240

Gln Glu Glu Glu Thr Tyr Asn Ile Val Ala Ala His Gly Tyr Phe Gly
                        245                 250                 255

Arg Leu Ile Phe Gln Tyr Ala Ser Phe Asn Asn Ser Arg Ser Leu His
                        260                 265                 270

Phe Phe Leu Gly Ala Trp Pro Val Ile Gly Ile Trp Phe Thr Ala Met
                        275                 280                 285

Gly Val Ser Thr Met Ala Phe Asn Leu Asn Gly Phe Asn Phe Asn Gln
                        290                 295                 300

Ser Ile Leu Asp Ser Gln Gly Arg Val Ile Gly Thr Trp Ala Asp Val
        305                 310                 315                 320

Leu Asn Arg Ala Asn Ile Gly Phe Glu Val Met His Glu Arg Asn Ala
                        325                 330                 335

His Asn Phe Pro Leu Asp Leu Ala Ser Gly Glu Gln Ala Pro Val Ala
                        340                 345                 350

Leu Thr Ala Pro Ala Val Asn Gly
                        355                 360

<210> SEQ ID NO 57
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Ala 209/Ala 212 mutant

<400> SEQUENCE: 57

Met Thr Thr Thr Leu Gln Gln Arg Glu Ser Ala Ser Leu Trp Glu Gln
```

```
              1               5                  10                 15

Phe Cys Gln Trp Val Thr Ser Thr Asn Asn Arg Ile Tyr Val Gly Trp
                            20                 25                 30

Phe Gly Thr Leu Met Ile Pro Thr Leu Leu Thr Ala Thr Thr Cys Phe
                            35                 40                 45

Ile Ile Ala Phe Ile Ala Ala Pro Val Asp Ile Asp Gly Ile Arg
                            50                 55                 60

Glu Pro Val Ala Gly Ser Leu Leu Tyr Gly Asn Asn Ile Ile Ser Gly
             65                 70                 75                 80

Ala Val Val Pro Ser Ser Asn Ala Ile Gly Leu His Phe Tyr Pro Ile
                            85                 90                 95

Trp Glu Ala Ala Ser Leu Asp Glu Trp Leu Tyr Asn Gly Gly Pro Tyr
                            100                105                110

Gln Leu Val Val Phe His Phe Leu Ile Gly Ile Phe Cys Tyr Met Gly
                            115                120                125

Arg Gln Trp Glu Leu Ser Tyr Arg Leu Gly Met Arg Pro Trp Ile Cys
                            130                135                140

Val Ala Tyr Ser Ala Pro Val Ser Ala Ala Thr Ala Val Phe Leu Ile
            145                150                155                160

Tyr Pro Ile Gly Gln Gly Ser Phe Ser Asp Gly Met Pro Leu Gly Ile
                            165                170                175

Ser Gly Thr Phe Asn Phe Met Ile Val Phe Gln Ala Glu His Asn Ile
                            180                185                190

Leu Met His Pro Phe His Met Leu Gly Val Ala Gly Val Phe Gly Gly
                            195                200                205

Ala Leu Phe Ala Ala Met His Gly Ser Leu Val Thr Ser Ser Leu Val
                            210                215                220

Arg Glu Thr Thr Glu Val Glu Ser Gln Asn Tyr Gly Tyr Lys Phe Gly
            225                230                235                240

Gln Glu Glu Glu Thr Tyr Asn Ile Val Ala Ala His Gly Tyr Phe Gly
                            245                250                255

Arg Leu Ile Phe Gln Tyr Ala Ser Phe Asn Asn Ser Arg Ser Leu His
                            260                265                270

Phe Phe Leu Gly Ala Trp Pro Val Ile Gly Ile Trp Phe Thr Ala Met
                            275                280                285

Gly Val Ser Thr Met Ala Phe Asn Leu Asn Gly Phe Asn Phe Asn Gln
                            290                295                300

Ser Ile Leu Asp Ser Gln Gly Arg Val Ile Gly Thr Trp Ala Asp Val
            305                310                315                320

Leu Asn Arg Ala Asn Ile Gly Phe Glu Val Met His Glu Arg Asn Ala
                            325                330                335

His Asn Phe Pro Leu Asp Leu Ala Ser Gly Glu Gln Ala Pro Val Ala
                            340                345                350

Leu Thr Ala Pro Ala Val Asn Gly
                            355                360

<210> SEQ ID NO 58
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Gly 209/Gly 212 mutant

<400> SEQUENCE: 58

Met Thr Thr Thr Leu Gln Gln Arg Glu Ser Ala Ser Leu Trp Glu Gln
```

|   |   |   |   |   |   |   |   |   |   |   |   |   |   |   |
|---|---|---|---|---|---|---|---|---|---|---|---|---|---|---|
| 1 |   |   |   | 5 |   |   |   |   | 10 |   |   |   |   | 15 |
| Phe | Cys | Gln | Trp | Val | Thr | Ser | Thr | Asn | Asn | Arg | Ile | Tyr | Val | Gly | Trp |
|   |   |   | 20 |   |   |   |   | 25 |   |   |   |   | 30 |   |
| Phe | Gly | Thr | Leu | Met | Ile | Pro | Thr | Leu | Leu | Thr | Ala | Thr | Thr | Cys | Phe |
|   |   | 35 |   |   |   |   | 40 |   |   |   |   | 45 |   |   |
| Ile | Ile | Ala | Phe | Ile | Ala | Ala | Pro | Val | Asp | Ile | Asp | Gly | Ile | Arg |
| 50 |   |   |   |   | 55 |   |   |   |   | 60 |   |   |   |   |
| Glu | Pro | Val | Ala | Gly | Ser | Leu | Leu | Tyr | Gly | Asn | Asn | Ile | Ile | Ser | Gly |
| 65 |   |   |   |   | 70 |   |   |   |   | 75 |   |   |   |   | 80 |
| Ala | Val | Val | Pro | Ser | Ser | Asn | Ala | Ile | Gly | Leu | His | Phe | Tyr | Pro | Ile |
|   |   |   |   | 85 |   |   |   |   | 90 |   |   |   |   | 95 |   |
| Trp | Glu | Ala | Ala | Ser | Leu | Asp | Glu | Trp | Leu | Tyr | Asn | Gly | Gly | Pro | Tyr |
|   |   |   | 100 |   |   |   |   | 105 |   |   |   |   | 110 |   |
| Gln | Leu | Val | Val | Phe | His | Phe | Leu | Ile | Gly | Ile | Phe | Cys | Tyr | Met | Gly |
|   |   |   | 115 |   |   |   |   | 120 |   |   |   |   | 125 |   |
| Arg | Gln | Trp | Glu | Leu | Ser | Tyr | Arg | Leu | Gly | Met | Arg | Pro | Trp | Ile | Cys |
|   |   |   | 130 |   |   |   |   | 135 |   |   |   |   | 140 |   |
| Val | Ala | Tyr | Ser | Ala | Pro | Val | Ser | Ala | Ala | Thr | Ala | Val | Phe | Leu | Ile |
| 145 |   |   |   |   | 150 |   |   |   |   | 155 |   |   |   |   | 160 |
| Tyr | Pro | Ile | Gly | Gln | Gly | Ser | Phe | Ser | Asp | Gly | Met | Pro | Leu | Gly | Ile |
|   |   |   |   | 165 |   |   |   |   | 170 |   |   |   |   | 175 |   |
| Ser | Gly | Thr | Phe | Asn | Phe | Met | Ile | Val | Phe | Gln | Ala | Glu | His | Asn | Ile |
|   |   |   | 180 |   |   |   |   | 185 |   |   |   |   | 190 |   |
| Leu | Met | His | Pro | Phe | His | Met | Leu | Gly | Val | Ala | Gly | Val | Phe | Gly | Gly |
|   |   |   | 195 |   |   |   |   | 200 |   |   |   |   | 205 |   |
| Gly | Leu | Phe | Gly | Ala | Met | His | Gly | Ser | Leu | Val | Thr | Ser | Ser | Leu | Val |
|   | 210 |   |   |   |   | 215 |   |   |   |   | 220 |   |   |   |   |
| Arg | Glu | Thr | Thr | Glu | Val | Glu | Ser | Gln | Asn | Tyr | Gly | Tyr | Lys | Phe | Gly |
| 225 |   |   |   |   | 230 |   |   |   |   | 235 |   |   |   |   | 240 |
| Gln | Glu | Glu | Glu | Thr | Tyr | Asn | Ile | Val | Ala | Ala | His | Gly | Tyr | Phe | Gly |
|   |   |   |   | 245 |   |   |   |   | 250 |   |   |   |   | 255 |   |
| Arg | Leu | Ile | Phe | Gln | Tyr | Ala | Ser | Phe | Asn | Asn | Ser | Arg | Ser | Leu | His |
|   |   |   | 260 |   |   |   |   | 265 |   |   |   |   | 270 |   |
| Phe | Phe | Leu | Gly | Ala | Trp | Pro | Val | Ile | Gly | Ile | Trp | Phe | Thr | Ala | Met |
|   | 275 |   |   |   |   | 280 |   |   |   |   | 285 |   |   |   |   |
| Gly | Val | Ser | Thr | Met | Ala | Phe | Asn | Leu | Asn | Gly | Phe | Asn | Phe | Asn | Gln |
|   | 290 |   |   |   |   | 295 |   |   |   |   | 300 |   |   |   |   |
| Ser | Ile | Leu | Asp | Ser | Gln | Gly | Arg | Val | Ile | Gly | Thr | Trp | Ala | Asp | Val |
| 305 |   |   |   |   | 310 |   |   |   |   | 315 |   |   |   |   | 320 |
| Leu | Asn | Arg | Ala | Asn | Ile | Gly | Phe | Glu | Val | Met | His | Glu | Arg | Asn | Ala |
|   |   |   |   | 325 |   |   |   |   | 330 |   |   |   |   | 335 |   |
| His | Asn | Phe | Pro | Leu | Asp | Leu | Ala | Ser | Gly | Glu | Gln | Ala | Pro | Val | Ala |
|   |   |   | 340 |   |   |   |   | 345 |   |   |   |   | 350 |   |
| Leu | Thr | Ala | Pro | Ala | Val | Asn | Gly |
|   |   | 355 |   |   |   |   | 360 |

<210> SEQ ID NO 59
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Ala 208 mutant

<400> SEQUENCE: 59

Met Thr Thr Thr Leu Gln Gln Arg Glu Ser Ala Ser Leu Trp Glu Gln

```
  1               5                  10                 15
Phe Cys Gln Trp Val Thr Ser Thr Asn Asn Arg Ile Tyr Val Gly Trp
                 20                  25                 30

Phe Gly Thr Leu Met Ile Pro Thr Leu Leu Thr Ala Thr Thr Cys Phe
                 35                  40                 45

Ile Ile Ala Phe Ile Ala Ala Pro Val Asp Ile Asp Gly Ile Arg
 50                  55                  60

Glu Pro Val Ala Gly Ser Leu Leu Tyr Gly Asn Asn Ile Ile Ser Gly
 65                  70                  75                 80

Ala Val Val Pro Ser Ser Asn Ala Ile Gly Leu His Phe Tyr Pro Ile
                 85                  90                 95

Trp Glu Ala Ala Ser Leu Asp Glu Trp Leu Tyr Asn Gly Gly Pro Tyr
                 100                 105                110

Gln Leu Val Val Phe His Phe Leu Ile Gly Ile Phe Cys Tyr Met Gly
                 115                 120                125

Arg Gln Trp Glu Leu Ser Tyr Arg Leu Gly Met Arg Pro Trp Ile Cys
                 130                 135                140

Val Ala Tyr Ser Ala Pro Val Ser Ala Ala Thr Ala Val Phe Leu Ile
145                  150                 155                160

Tyr Pro Ile Gly Gln Gly Ser Phe Ser Asp Gly Met Pro Leu Gly Ile
                 165                 170                175

Ser Gly Thr Phe Asn Phe Met Ile Val Phe Gln Ala Glu His Asn Ile
                 180                 185                190

Leu Met His Pro Phe His Met Leu Gly Val Ala Gly Val Phe Gly Ala
                 195                 200                205

Ser Leu Phe Ser Ala Met His Gly Ser Leu Val Thr Ser Ser Leu Val
                 210                 215                220

Arg Glu Thr Thr Glu Val Glu Ser Gln Asn Tyr Gly Tyr Lys Phe Gly
225                  230                 235                240

Gln Glu Glu Glu Thr Tyr Asn Ile Val Ala Ala His Gly Tyr Phe Gly
                 245                 250                255

Arg Leu Ile Phe Gln Tyr Ala Ser Phe Asn Asn Ser Arg Ser Leu His
                 260                 265                270

Phe Phe Leu Gly Ala Trp Pro Val Ile Gly Ile Trp Phe Thr Ala Met
                 275                 280                285

Gly Val Ser Thr Met Ala Phe Asn Leu Asn Gly Phe Asn Phe Asn Gln
                 290                 295                300

Ser Ile Leu Asp Ser Gln Gly Arg Val Ile Gly Thr Trp Ala Asp Val
305                  310                 315                320

Leu Asn Arg Ala Asn Ile Gly Phe Glu Val Met His Glu Arg Asn Ala
                 325                 330                335

His Asn Phe Pro Leu Asp Leu Ala Ser Gly Glu Gln Ala Pro Val Ala
                 340                 345                350

Leu Thr Ala Pro Ala Val Asn Gly
                 355                 360

<210> SEQ ID NO 60
<211> LENGTH: 300
<212> TYPE: PRT
<213> ORGANISM: Synechocystis sp.
<220> FEATURE:
<221> NAME/KEY: misc_feature
<223> OTHER INFORMATION: D1-Ser 208 mutant

<400> SEQUENCE: 60

Met Thr Thr Thr Leu Gln Gln Arg Glu Ser Ala Ser Leu Trp Glu Gln
```

-continued

```
              1               5              10              15

Phe Cys Gln Trp Val Thr Ser Thr Asn Asn Arg Ile Tyr Val Gly Trp
                         20                  25                  30

Phe Gly Thr Leu Met Ile Pro Thr Leu Leu Thr Ala Thr Thr Cys Phe
                         35                  40                  45

Ile Ile Ala Phe Ile Ala Ala Pro Val Asp Ile Asp Gly Ile Arg
         50                  55                  60

Glu Pro Val Ala Gly Ser Leu Leu Tyr Gly Asn Asn Ile Ile Ser Gly
         65                  70                  75                  80

Ala Val Val Pro Ser Ser Asn Ala Ile Gly Leu His Phe Tyr Pro Ile
                         85                  90                  95

Trp Glu Ala Ala Ser Leu Asp Glu Trp Leu Tyr Asn Gly Gly Pro Tyr
                        100                 105                 110

Gln Leu Val Val Phe His Phe Leu Ile Gly Ile Phe Cys Tyr Met Gly
                        115                 120                 125

Arg Gln Trp Glu Leu Ser Tyr Arg Leu Gly Met Arg Pro Trp Ile Cys
                        130                 135                 140

Val Ala Tyr Ser Ala Pro Val Ser Ala Ala Thr Ala Val Phe Leu Ile
        145                 150                 155                 160

Tyr Pro Ile Gly Gln Gly Ser Phe Ser Asp Gly Met Pro Leu Gly Ile
                        165                 170                 175

Ser Gly Thr Phe Asn Phe Met Ile Val Phe Gln Ala Glu His Asn Ile
                        180                 185                 190

Leu Met His Pro Phe His Met Leu Gly Val Ala Gly Val Phe Gly Ser
                        195                 200                 205

Ser Leu Phe Ser Ala Met His Gly Ser Leu Val Thr Ser Ser Leu Val
                        210                 215                 220

Arg Glu Thr Thr Glu Val Glu Ser Gln Asn Tyr Gly Tyr Lys Phe Gly
        225                 230                 235                 240

Gln Glu Glu Glu Thr Tyr Asn Ile Val Ala Ala His Gly Tyr Phe Gly
                        245                 250                 255

Arg Leu Ile Phe Gln Tyr Ala Ser Phe Asn Asn Ser Arg Ser Leu His
                        260                 265                 270

Phe Phe Leu Gly Ala Trp Pro Val Ile Gly Ile Trp Phe Thr Ala Met
                        275                 280                 285

Gly Val Ser Thr Met Ala Phe Asn Leu Asn Gly Phe
                        290                 295                 300

<210> SEQ ID NO 61
<211> LENGTH: 360
<212> TYPE: PRT
<213> ORGANISM: Synechocystis sp.
<220> FEATURE:
<221> NAME/KEY: misc_feature
<223> OTHER INFORMATION: D1-Thr 208 mutant

<400> SEQUENCE: 61

Met Thr Thr Thr Leu Gln Gln Arg Glu Ser Ala Ser Leu Trp Glu Gln
1               5                  10                  15

Phe Cys Gln Trp Val Thr Ser Thr Asn Asn Arg Ile Tyr Val Gly Trp
                 20                  25                  30

Phe Gly Thr Leu Met Ile Pro Thr Leu Leu Thr Ala Thr Thr Cys Phe
             35                  40                  45

Ile Ile Ala Phe Ile Ala Ala Pro Val Asp Ile Asp Gly Ile Arg
 50                  55                  60

Glu Pro Val Ala Gly Ser Leu Leu Tyr Gly Asn Asn Ile Ile Ser Gly
```

-continued

```
             65                  70                  75                  80
            Ala Val Val Pro Ser Ser Asn Ala Ile Gly Leu His Phe Tyr Pro Ile
                            85                  90                  95

Trp Glu Ala Ala Ser Leu Asp Glu Trp Leu Tyr Asn Gly Gly Pro Tyr
                            100                 105                 110

Gln Leu Val Val Phe His Phe Leu Ile Gly Ile Phe Cys Tyr Met Gly
                            115                 120                 125

Arg Gln Trp Glu Leu Ser Tyr Arg Leu Gly Met Arg Pro Trp Ile Cys
                            130                 135                 140

Val Ala Tyr Ser Ala Pro Val Ser Ala Ala Thr Ala Val Phe Leu Ile
            145                 150                 155                 160

Tyr Pro Ile Gly Gln Gly Ser Phe Ser Asp Gly Met Pro Leu Gly Ile
                            165                 170                 175

Ser Gly Thr Phe Asn Phe Met Ile Val Phe Gln Ala Glu His Asn Ile
                            180                 185                 190

Leu Met His Pro Phe His Met Leu Gly Val Ala Gly Val Phe Gly Thr
                            195                 200                 205

Ser Leu Phe Ser Ala Met His Gly Ser Leu Val Thr Ser Ser Leu Val
                            210                 215                 220

Arg Glu Thr Thr Glu Val Glu Ser Gln Asn Tyr Gly Tyr Lys Phe Gly
            225                 230                 235                 240

Gln Glu Glu Glu Thr Tyr Asn Ile Val Ala Ala His Gly Tyr Phe Gly
                            245                 250                 255

Arg Leu Ile Phe Gln Tyr Ala Ser Phe Asn Asn Ser Arg Ser Leu His
                            260                 265                 270

Phe Phe Leu Gly Ala Trp Pro Val Ile Gly Ile Trp Phe Thr Ala Met
                            275                 280                 285

Gly Val Ser Thr Met Ala Phe Asn Leu Asn Gly Phe Asn Phe Asn Gln
                            290                 295                 300

Ser Ile Leu Asp Ser Gln Gly Arg Val Ile Gly Thr Trp Ala Asp Val
            305                 310                 315                 320

Leu Asn Arg Ala Asn Ile Gly Phe Glu Val Met His Glu Arg Asn Ala
                            325                 330                 335

His Asn Phe Pro Leu Asp Leu Ala Ser Gly Glu Gln Ala Pro Val Ala
                            340                 345                 350

Leu Thr Ala Pro Ala Val Asn Gly
                            355                 360
```

PHOTOSYNTHETIC ORGANISMS AND COMPOSITIONS AND METHODS OF GENERATING SAME

RELATED APPLICATIONS

This Application is a National Phase of PCT Patent Application No. PCT/IL2007/000920 having International filing date of Jul. 22, 2007, which claims the benefit of U.S. Provisional Patent Application No. 60/831,937 filed on Jul. 20, 2006. The contents of the above Applications are all incorporated herein by reference.

FIELD AND BACKGROUND OF THE INVENTION

The present invention relates to photosynthetic organisms and, compositions and methods of generating same.

The energy crises of the 1970's combined with world-wide climate changes linked to the accumulation of excess carbon dioxide in the atmosphere, has initiated a significant return to the development and use of biomass as a resource for fuel and chemical products. Presently, society's dependence is shifting away from petroleum to renewable biomass and energy resources, in order to aid in the development of a sustainable industrial society and to manage the green house effect. The US department of energy has set goals to replace 30% of the liquid petroleum transportation fuel with biofuels and to replace 25% of the industrial organic chemicals with biomass-derived chemicals by 2025 [Ragauskas et al, *Science*, 311, 484-489 (2006)]. The EU has set targets at 5.75% for all petrol and diesel transport fuels to be biomass derived by the end of 2010 [Ragauskas et al, supra].

Biomass production methods presently enable different chemical and biofuel (e.g. biodiesel and ethanol) production from plant resources. Current production of biomass in general and biofuel in particular mainly relies on higher plants and trees, as for example corn and sugar cane plants. However, biofuel production from these plants is limited in yield and enhanced consumption of such plants as a biofuel source would lead to a severe shortage in food supply worldwide. Furthermore, maximum productivities of higher plants and trees are restricted to areas with prime soil, water, and climate (primarily the tropics). Plant leaves exist in an aerial environment and are subject to large evaporative moisture losses, which directly inhibit the process of photosynthesis.

Biomass production by cyanobacteria and microalgae, which are the most productive carbon dioxide users of all photosynthetic organisms and can fix greater amounts of carbon dioxide per land area than higher plants, is restricted to a relatively narrow range of temperatures defined by their native habitat. Mesophilic organisms show maximal rate constant at 20-30° C. while thermophilic strains achieve similar rates at 60-70° C. This temperature range mainly reflects constrains of the photosynthetic energy conversion machinery (photosystems) and of the carbon fixation one (the Rubisco complex).

Biomass is mainly generated in the course of photosynthesis which photocatalyses carbon dioxide fixation via the Rubisco complex. Plants, microalgea and cyanobacteria use photosystems I and II (PSI and PSII), to convert light energy into chemical energy. The central unit of a PSII protein complex is the reaction center (RC). The functional core of PSII RC consists of a heterodimer made of the two homologous protein subunits D1 and D2 along with one unit of cytochrome b559. The D1 and D2 protein subunits each have five (A, B, C, D, and E) transmembranal (TM) α helices. The cofactors that carry out electron transfer (chlorophillus type molecules and quinones) in response to illumination and thereby perform the primary energy conversion, are mainly bound (non-covalently) to helices D and E of the D1/D2 subunits.

Numerous studies showed that the photosynthetic energy conversion by PSII RC is highly sensitive to irradiation and temperature variations [Takahashi et al., *Plant Cell Physiol* 45, 251-5 (2004); Murata et al *Biochim Biophys Acta* 1767, 414-21 (2007)]. Also, recent studies have suggested that the PSII RC is a key player in regulating the rate of photosynthetic energy conversion in response to the prevailing temperature [Yamasaki et al., *Plant Physiol* 128, 1087-97 (2002)].

Taking into consideration the global warming effect, annual and even daily changes in temperature in aquatic areas (e.g., oceans, small lakes and ponds), dramatically narrow the efficiency of biomass production of thermophilic and mesophilic microalgal strains as well as of different strains of cyanobacteria and thus limits their growth to the tropical arena. Even there, current global heating is expected to exceed the thermotolerance and production efficacy of these organisms [Wraight, *Front Biosci* 9, 309-37 (2004); Behrenfeld et al. *Nature* 444, 752-5 (2006)]. Although the expected changes in global temperatures are only in the order of several degrees, it is predicted that biomass production may be dramatically effected.

The increased need for biofuel and the concomitant shortage of food across the world underscores the urgent need for methods of increasing resistance of plants, algea and microalgae to ambient temperature changes.

SUMMARY OF THE INVENTION

The present invention successfully addresses the shortcomings of the presently known configurations by providing photosynthetic organisms and, compositions and methods of generating same.

Thus, according to one aspect of the present invention there is provided an isolated polynucleotide comprising a nucleic acid sequence encoding a polypeptide of a Type II reaction center of a photosynthetic organism, the nucleic acid sequence being capable of imparting the photosystem II reaction center with an activity under a temperature range different than that of the type II reaction center endogenous to the photosynthetic organism.

According to further features in preferred embodiments of the invention described below, the polypeptide of the photosystem II reaction center is selected from the group consisting of D1, D2, L and M.

According to still further features in the described preferred embodiments, the polypeptide is D1.

According to still further features in the described preferred embodiments, the activity comprises solar energy conversion activity.

According to still further features in the described preferred embodiments, the D1 polypeptide comprises an amino acid sequence alteration at a position corresponding to 209 of SEQ ID NO: 36 and/or at a position corresponding to 212 of the SEQ ID NO: 36.

According to still further features in the described preferred embodiments, the amino acid sequence alteration at a position corresponding to 209 of SEQ ID NO: 36 comprises a Serine to Alanine mutation.

According to still further features in the described preferred embodiments, the amino acid sequence alteration at a position corresponding to 212 of SEQ ID NO: 36 comprises a Serine to Cysteine mutation.

According to still further features in the described preferred embodiments, the D1 polypeptide comprises an amino acid sequence alteration at any amino acid position corresponding to 208-212 of SEQ ID NO: 36.

According to still further features in the described preferred embodiments, the photosystem II reaction center is rendered more thermotolerant as compared to the photosystem II reaction center endogenous to the photosynthetic organism.

According to still further features in the described preferred embodiments, the photosystem II reaction center is rendered more thermoplastic as compared to the photosystem II reaction center endogenous to the photosynthetic organism.

According to still further features in the described preferred embodiments, the photosynthetic organism is selected from the group consisting of a higher plant, a photosynthetic bacteria and an algae.

According to still further features in the described preferred embodiments, the photosynthetic organism is selected from the group consisting of a mesophile, a thermophile and a psychrophile.

According to still further features in the described preferred embodiments, the temperature range comprises 10° C.-43° C.

According to still further features in the described preferred embodiments, the temperature range comprises an upwards shift.

According to still further features in the described preferred embodiments, the upwards shift is by at least 6° C.

According to still further features in the described preferred embodiments, the temperature range comprises a downwards shift.

According to still further features in the described preferred embodiments, the downwards shift is by at least 2.5° C.

According to still further features in the described preferred embodiments, the temperature range comprise a wider temperature range.

According to still further features in the described preferred embodiments, an amino acid at position 209 or 212 is selected from the group consisting of glycine, cysteine, alanine, threonin, asparagine, aspartanine, proline, valine, isoleucine, leucine, glutamine and glutamic acid.

According to another aspect of the present invention there is provided a nucleic acid construct comprising the polynucleotide.

According to still further features in the described preferred embodiments, the nucleic acid construct further comprises a cis-regulatory element.

According to still further features in the described preferred embodiments, the cis-regulatory element is a promoter.

According to yet another aspect of the present invention there is provided a cell of a photosynthetic organism comprising the nucleic acid sequence.

According to still another aspect of the present invention there is provided an isolated polypeptide comprising an amino acid sequence encoding a polypeptide of a photosystem II reaction center of a photosynthetic organism, the nucleic acid sequence being capable of imparting the photosystem II reaction center with an activity under a temperature range different than that of the type II reaction center endogenous to the photosynthetic organism.

According to still further features in the described preferred embodiments, the polypeptide is selected from the group consisting of D1, D2, L and M.

According to still further features in the described preferred embodiments, the polypeptide is D1.

According to still further features in the described preferred embodiments, the activity comprise solar energy conversion activity.

According to still further features in the described preferred embodiments, the D1 comprises an amino acid sequence alteration at a position corresponding to 209 of SEQ ID NO: 36 and/or at a position corresponding to 212 of the SEQ ID NO: 36.

According to still further features in the described preferred embodiments, the amino acid sequence alteration at a position corresponding to 209 of SEQ ID NO: 36 comprises a Serine to Alanine mutation.

According to still further features in the described preferred embodiments, the amino acid sequence alteration at a position corresponding to 212 of SEQ ID NO: 36 comprises a Serine to Cysteine mutation.

According to still further features in the described preferred embodiments, the D1 comprises an amino acid sequence alteration at any amino acid position corresponding to 208-212 of SEQ ID NO: 36.

According to still further features in the described preferred embodiments, the photosystem II reaction center is rendered more thermotolerant as compared to the photosystem II reaction center endogenous to the photosynthetic organism.

According to still further features in the described preferred embodiments, the photosystem II reaction center is rendered more thermoplastic as compared to the photosystem II reaction center endogenous to the photosynthetic organism.

According to still further features in the described preferred embodiments, the photosynthetic organism is selected from the group consisting of a higher plant, a cyanobacteria and an algae.

According to still further features in the described preferred embodiments, the photosynthetic organism is selected from the group consisting of a mesophile, a thermophile and a psychrophile.

According to still further features in the described preferred embodiments, the temperature range comprises 10° C.-43° C.

According to still further features in the described preferred embodiments, the temperature range comprises an upwards shift.

According to still further features in the described preferred embodiments, the upwards shift is by at least 6° C.

According to still further features in the described preferred embodiments, the temperature range comprises a downwards shift.

According to still further features in the described preferred embodiments, the downwards shift is by at least 2.5° C.

According to still further features in the described preferred embodiments, the temperature range comprise a wider temperature range.

According to still further features in the described preferred embodiments, an amino acid at position 209 or 212 is selected from the group consisting of glycine, cysteine, alanine, threonin, asparagine, aspartanine, proline, valine, isoleucine, leucine, glutamine and glutamic acid.

According to still further features in the described preferred embodiments, the amino acid sequence is selected from the group consisting of SEQ ID NO: 37, 38, 50, 52 and 56.

According to an additional aspect of the present invention there is provided a photosynthetic organism comprising an exogenous nucleic acid sequence encoding a polypeptide of a photosystem II reaction center of the photosynthetic organism, the nucleic acid sequence imparting the photosystem II reaction center with an activity under a temperature range different than that of the photosystem II reaction center endogenous to the photosynthetic organism.

According to still further features in the described preferred embodiments, the photosynthetic organism is selected from the group consisting of a higher plant, a cyanobacteria and an algae.

According to still further features in the described preferred embodiments, the photosynthetic organism is selected from the group consisting of a mesophile, a thermophile and a psychrophile.

According to still further features in the described preferred embodiments, the exogenous nucleic acid sequence further renders the organism more thermoplastic than an identical photosynthetic organism not comprising the exogenous nucleic acid sequence.

According to still further features in the described preferred embodiments, the exogenous nucleic acid sequence further renders the organism capable of expressing more Rubisco than an identical photosynthetic organism not comprising the exogenous nucleic acid sequence.

According to still further features in the described preferred embodiments, the exogenous nucleic acid sequence further renders the organism capable of expressing more psaC than an identical photosynthetic organism not comprising the exogenous nucleic acid sequence.

According to still further features in the described preferred embodiments, the exogenous nucleic acid sequence further renders the organism capable of growing faster than a photosynthetic organism not comprising the exogenous nucleic acid sequence.

According to still further features in the described preferred embodiments, the exogenous nucleic acid sequence further renders the organism capable of accumulating more chlorophyll than an identical photosynthetic organism not comprising the exogenous nucleic acid sequence.

According to yet an additional aspect of the present invention there is provided a method of improving biomass/vigor/yield of a photosynthetic organism comprising introducing into the photosynthetic organism the isolated polynucleotide, thereby increasing biomass, vigor and/or yield of the photosynthetic organism.

According to still further features in the described preferred embodiments, the method further comprising growing the photosynthetic organism under abiotic stress conditions.

According to still further features in the described preferred embodiments, the abiotic stress conditions comprise heat, cold and alternating temperatures.

According to still an additional aspect of the present invention there is provided a method of increasing activity of a photosystem II reaction center of a photosynthetic organism under non-physiological temperature, the method comprising introducing into the photosynthetic organism the isolated polynucleotide, thereby increasing the activity of a photosystem II reaction center under a non-physiological temperature.

According to a further aspect of the present invention there is provided a method of identifying mutations which impart a photosynthetic organism with a photosynthetic activity under a non-physiological temperature, the method comprising: subjecting the photosynthetic organisms to a mutagen, so as to obtain mutated photosynthetic organisms; identifying an organism of the mutated photosynthetic organisms exhibiting at least one parameter associated with enhanced photosynthetic activity under non-physiological temperature as compared to corresponding wild type photosynthetic organisms; and identifying mutations in a polypeptide of a photosystem II reaction center of the organism, the mutations being correlated with photosynthetic activity under a non-physiological temperature.

According to still further features in the described preferred embodiments, the at least one parameter associated with enhanced photosynthetic activity is selected from the group consisting of biomass, growth rate, rubisco level, chlorophyll content, psaC level and thermoplasticity.

According to still further features in the described preferred embodiments, the polypeptide of a photosystem II reaction center is selected from the group consisting of D1, D2, L and M.

According to yet a further aspect of the present invention there is provided a method of increasing hydrogen production in a photosynthetic organism, the method comprising introducing into the photosynthetic organism capable of generating hydrogen the isolated polynucleotide, thereby increasing hydrogen production in the photosynthetic organism.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-B are graphs depicting conserved structural and functional elements in photosystem II reaction centers (PTII RCs). FIG. 1A depicts (by the broken arrows) light induces electron transfer (ET) from a special pair of chlorophylls ($P_{D1}$ $P_{D2}$, green) through an accessory chlorophyll ($Chl_{D1}$, yellow) and pheophytin ($Pheo_{D1}$, purple) to quinones ($Q_A$ and $Q_B$, red) cofactors held by the D1 (magenta) and D2 (blue) subunits. The non-heme iron (pink) and the atoms lining the three main cavities (orange) are depicted; FIG. 1B depicts potential intersubunit hydrogen bonding (ISHB, dashed lines) between helices D and E of the two subunits. Residues involved in these bonds, e.g. D1-C212 (sulfur marked with a star) are depicted. For clarity, only the two largest cavities are drawn. The arrangement of the protein subunits L and M in purple bacteria well overlap with that of the D1 and D2 subunits, respectively, and the same holds for the chlorophyll and quinone cofactors [Kerner-Shlik et, *Nature*, 2006].

FIG. 1C is a table depicting sequence alignment of the D helices in reaction centers from photosystem II (D1 and D2) and from purple non sulfur bacteria and thermophilic green non sulfur bacteria (M and L). The conserved GxxxG-like sequence motif (were the G stands for the small amino acid residues Gly, Ala, Cys, Ser, Thr, gray shading) is found in the center of the D helix. Sequences were taken from the Swissprot database (or PDB and NCBI when available). Inter subunit hydrogen bond (ISHB) donor and acceptor residues are highlighted in bold. The alignment of the protein subunits is based on their structure and sequence homologies as previously described in the literature [Deisenhofer et al., *JMB* 246, 429-457 (1995)]. Of note, the GxxxG-like motifs in the protein subunits of the purple bacteria is shifted by one site compared with their position in photosystem II.

Figure 2B:
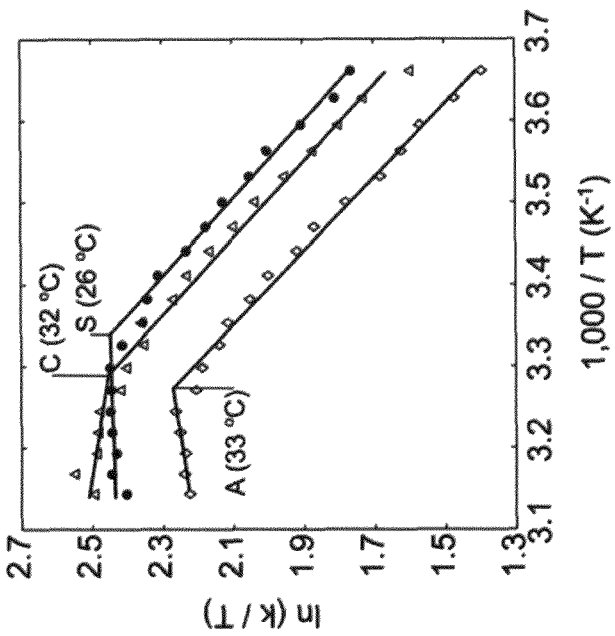
Figure 2A:
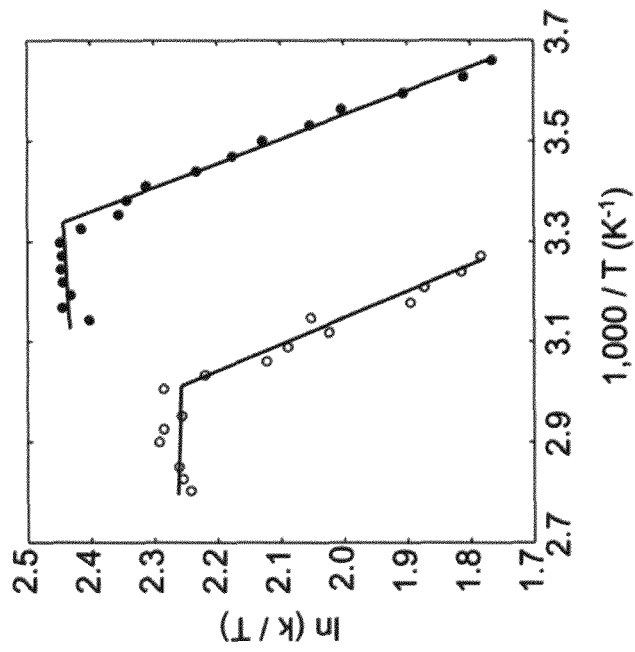

FIGS. 2A-B are graphs depicting the $Q_A^- \rightarrow Q_B$ ET rate in mesophilic and thermophilic cyanobacteria. FIG. 2A are Eyring plots for ET in a mesophile (*Synechocystis* 6803, closed circles) and a thermophile (*Thermosynechococcus elongatus*, open circles); FIG. 2B are Eyring plots for ET in D1-212 class I mutants Cys (triangles), and Ala (diamonds) compared to the *Synechocystis* 6803 Ser wild-type (closed circles).

FIGS. 3A-B are graphs depicting the effect of D1-212 residues on the photosystem II RC cavity in *Thermosynechococcus elongatus* structure. FIG. 3A depicts class I residue (Ser, space-fill representation of side-chain) maintains the cavity open; FIG. 3B depicts class II residue (Gln) abolishes one of the cavities and lines the largest cavity that is otherwise lined by flexible side-chains.

Figure 4B:
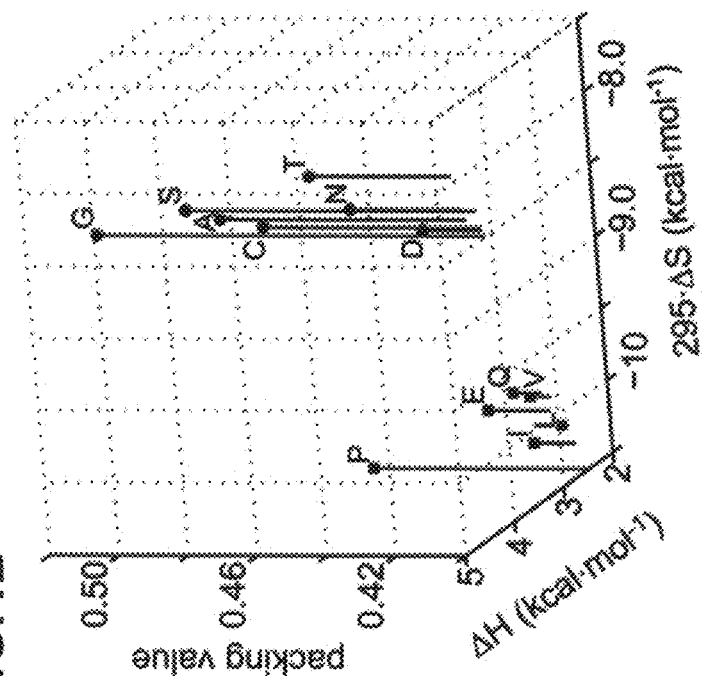
Figure 4A:
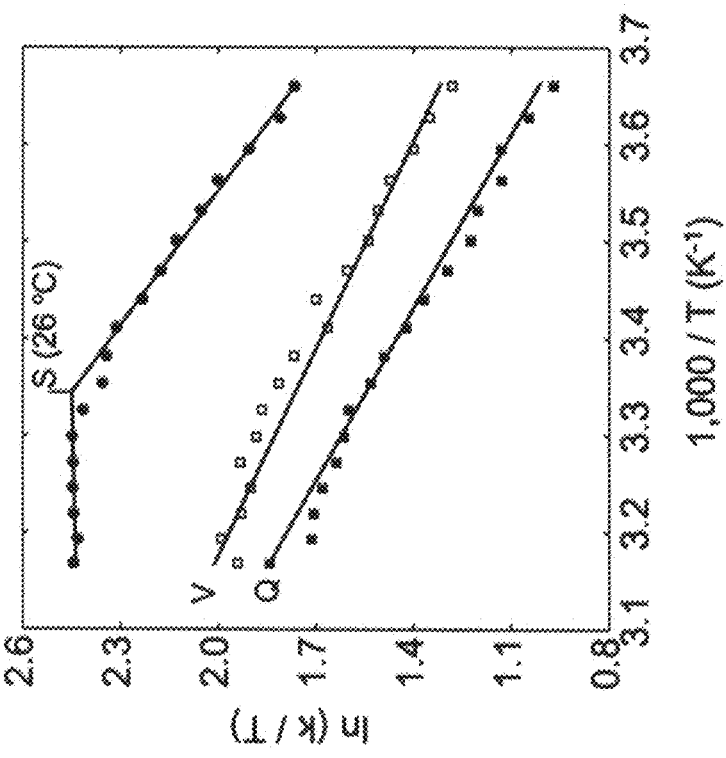

FIGS. 4A-B are graphs depicting temperature dependence and activation parameters of the $Q_A^- \rightarrow Q_B$ ET in D1-212 mutants of *Synechocystis* 6803. FIG. 4A are Eyring plots for D1-S212 (closed circles), D1-V212 (open squares) and D1-Q212 (closed squares); FIG. 4B depicts correlation between the activation entropy and enthalpy for the $Q_A^- \rightarrow Q_B$ ET and the packing values of residues at the D1-212 site. Class I residues (closed circles) are distinct from the class II residues (closed squares).

FIGS. 5A-E are graphs depicting structural Motifs within the photosystem II RCs. FIG. 5A depicts ISHBs between the D and E helices of the D1 and D2 subunits of the photosystem II RC. This figure zooms into FIG. 1B (detailed hereinabove) excluding for clarity the cartoon diagram of the D1 and D2 protein subunits as well as the cavities. Residues participating in transmembrane domain ISHBs (see FIG. 1C) are marked; FIG. 5B depicts ISHBs involving D1-212 and immediate vicinity. Viewing from the D2 subunit viewpoint it is shown that the D1-C212 SG atom (marked with an '*') can act as both an ISHB acceptor and a donor. As a donor, the hydrogen must "choose" between two alternative H-bond options. Atoms participating in ISHBs are marked; FIGS. C-E depict intra-protein cavities found in the transmembrane region between the D1 and D2 subunits of photosystem II RC. The largest three cavities (see Table 2) form a continuous area of high flexibility from just below the histidines ligating the non-heme iron and virtually till the center of mass of this protein complex. The atoms lining these cavities (FIG. 5C) are equally distributed between the D1 and D2 subunits (space-fill, color by chain color) and consist solely of helices D and E. The largest cavity is located at the center of the four-helix-bundle (FIG. 5D) as shown from a top view. A focus on the cavities and the residues participating in ISHBs (FIG. 5E) demonstrates that these two structural features are intimately entwined.

Figure 6:
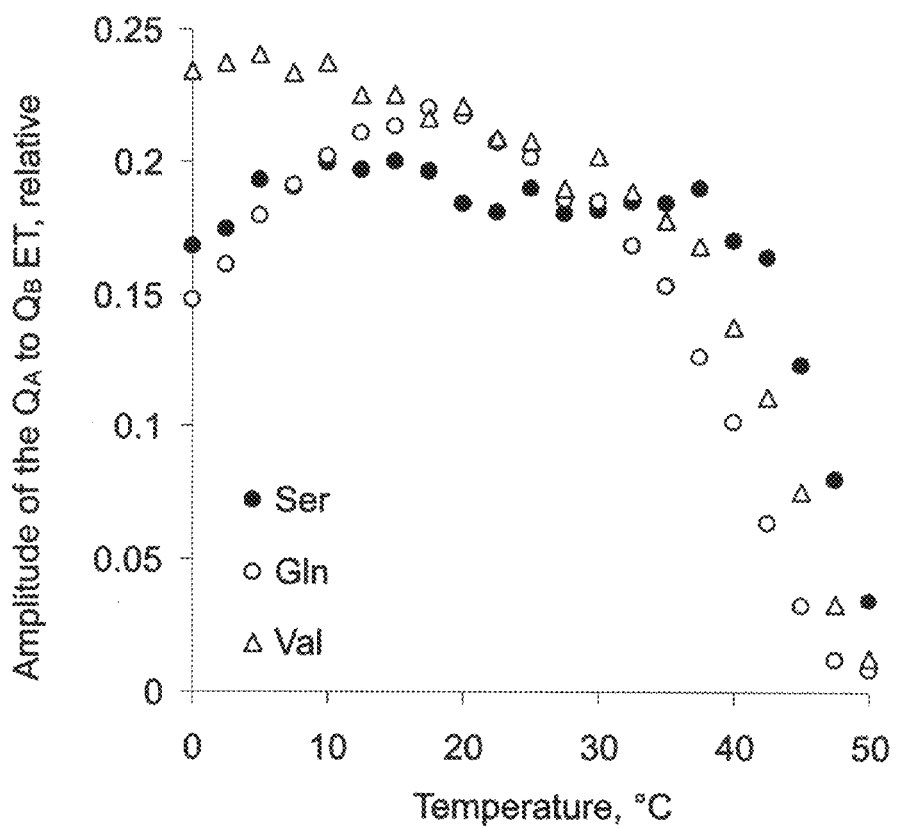

FIG. 6 is a graph depicting the amplitude of the shortest life-time component of the photosystem II RC fluorescence obtained at different temperatures as explained in the Methods section hereinbelow. Wild type fluorescence (D1-S212, full circles), class I mutants Val (open triangles) and Gln (open circles).

Figure 7:
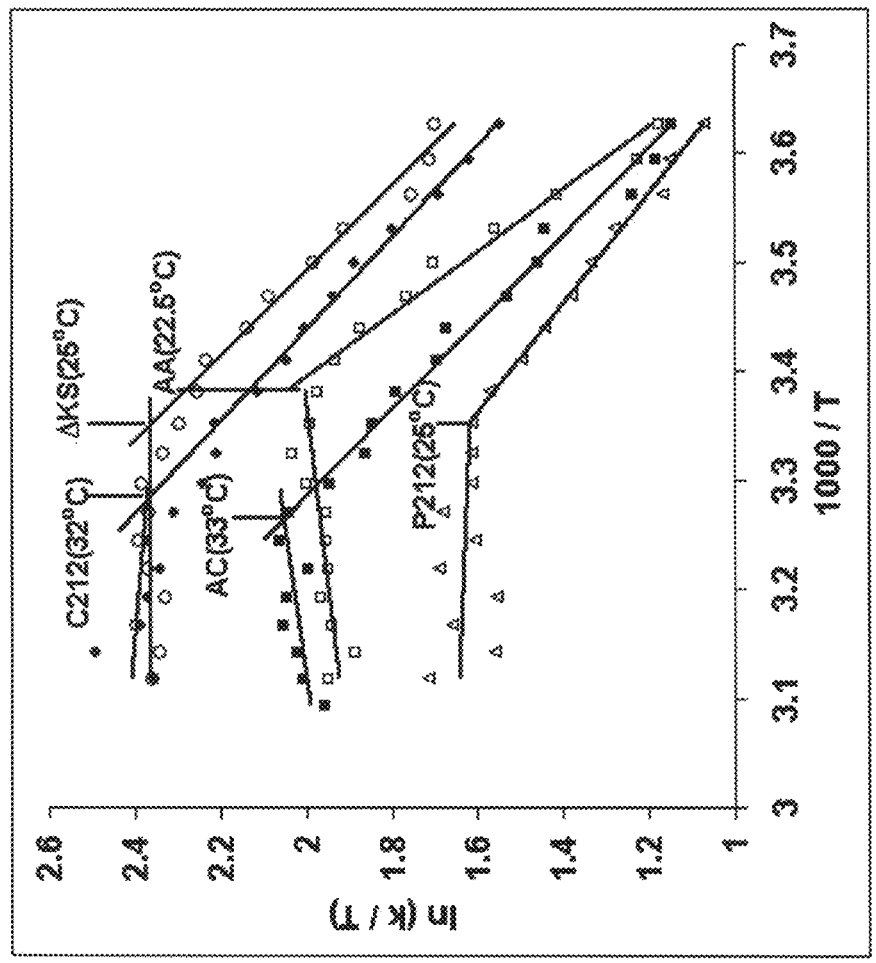

FIG. 7 is a graph depicting the Eyring plots for $Q_A^- \rightarrow Q_B$ ET in wild type (ΔKS, open circles), single mutants D1-212 Cys 212 (filled diamonds) and Pro 212 (triangles) and double mutants D1-209/212 SS209/212AA (open squares) and SS209/212AC (closed squares). The $T_o$ values are depicted for individual strains.

Figure 8A:
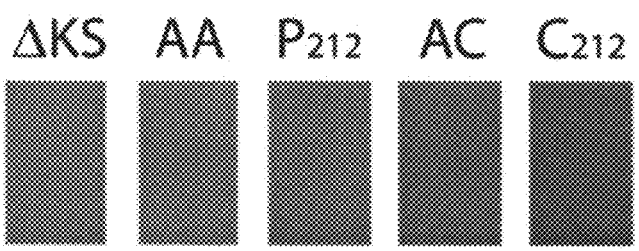
Figure 8B:
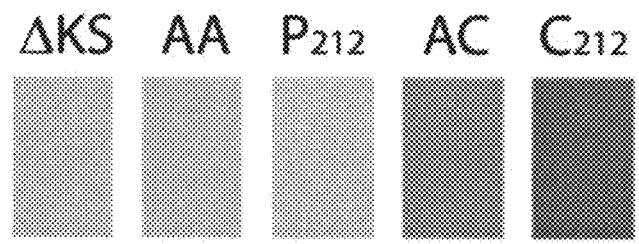
Figure 8C:
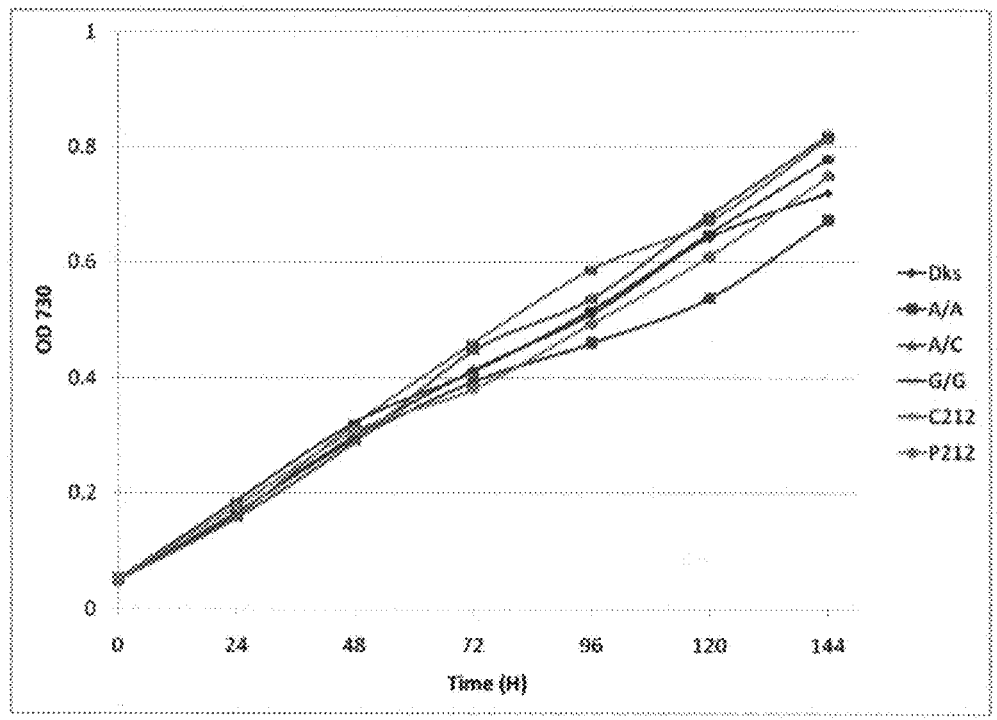
Figure 8D:
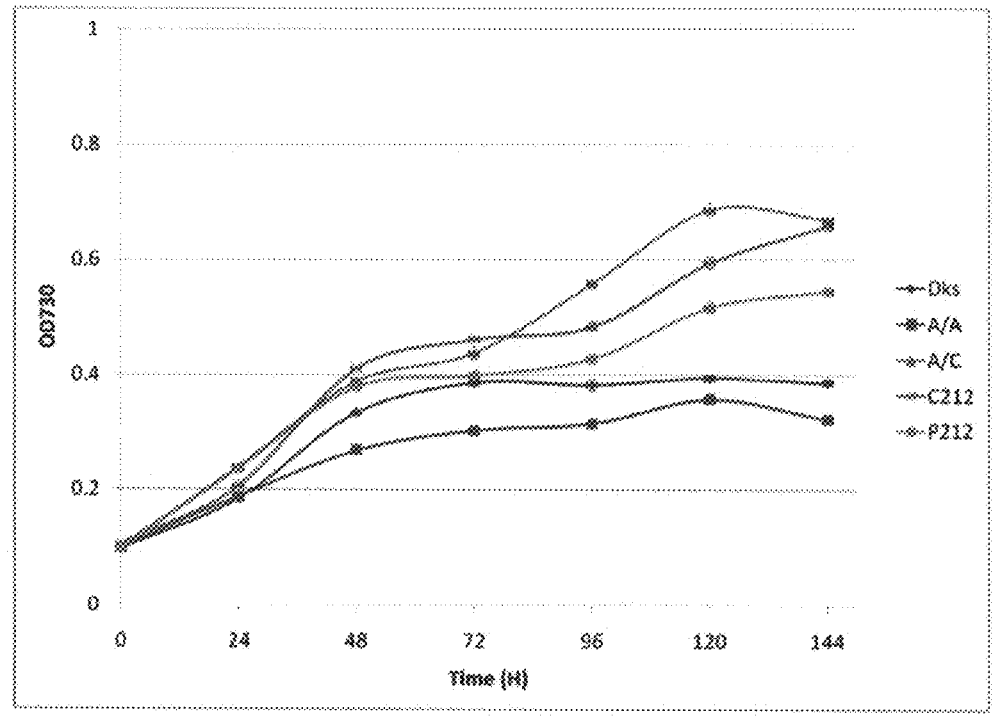
Figure 8E:
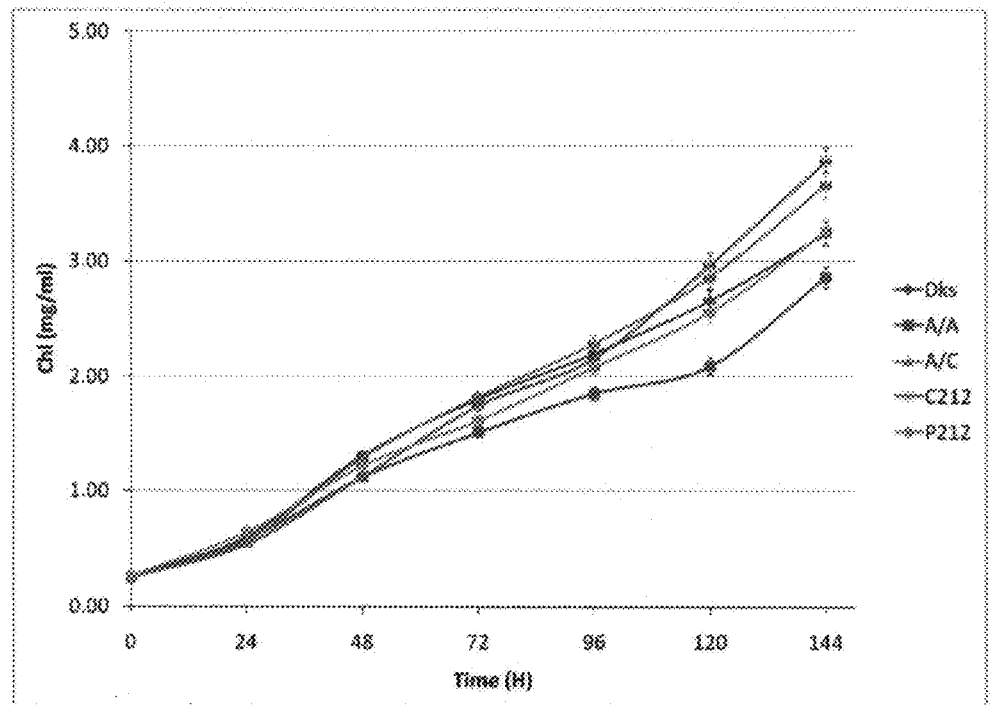
Figure 8F:
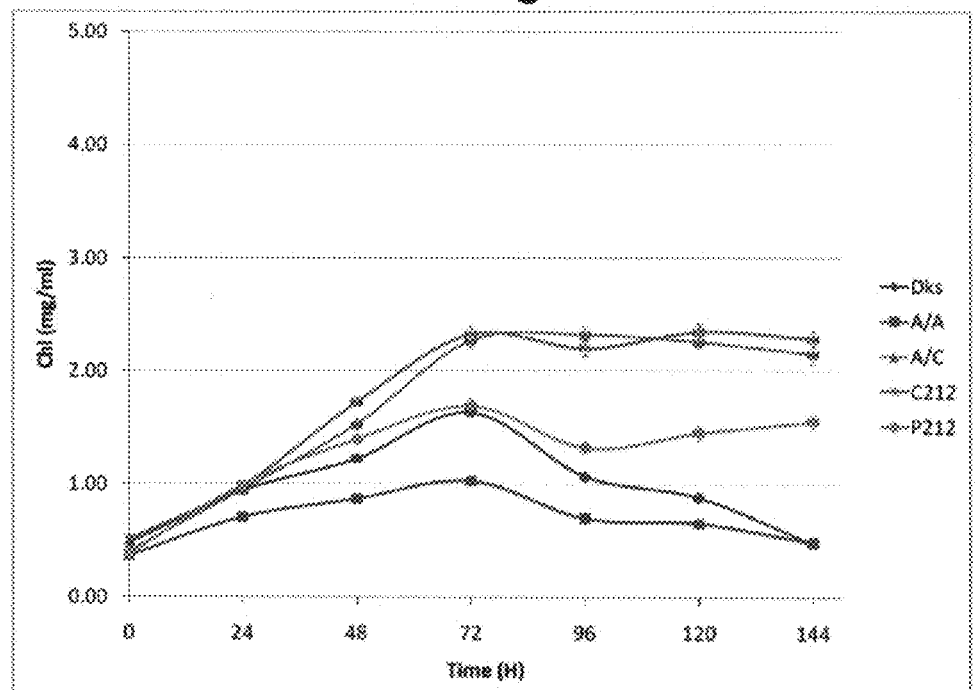

FIGS. 8A-L are graphs depicting the temperature effect on wild type (ΔKS) and the different mutants. FIG. 8A shows the colors of the different liquid cultures after incubation at 30° C. for six days; FIG. 8B shows the colors of the different liquid cultures after incubation at 43° C. for six days; FIG. 8C is a graph showing growth at 30° C. measured as turbidity at 730 nm; FIG. 8D is a graph showing growth at 43° C. measured as turbidity at 730 nm; FIG. 8E is a graph showing chlorophyll a accumulation rates in cell cultures grown at 30° C.; FIG. 8F is a graph showing chlorophyll a accumulation rates in cell cultures grown at 43° C.; FIG. 8G is an immunoblot showing the levels of D1 protein in cell cultures grown at 30° C.; FIG. 8H is an immunoblot showing the levels of D1 protein in cell cultures grown at 43° C.; FIG. 8I is an immunoblot showing the levels of the Rubisco large protein subunit in cell cultures grown at 30° C. FIG. 8J is an immunoblot showing the levels of the Rubisco large protein subunit in cell cultures grown at 43° C.; FIG. 8K is an immunoblot showing the levels of psaC protein in cell cultures grown at 30° C.; and FIG. 8L is an immunoblot showing the levels of psaC protein in cell cultures grown at 43° C.

Figure 9A:
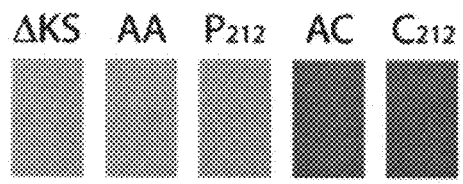
Figure 9B:
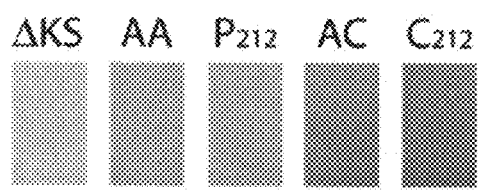
Figure 9C:
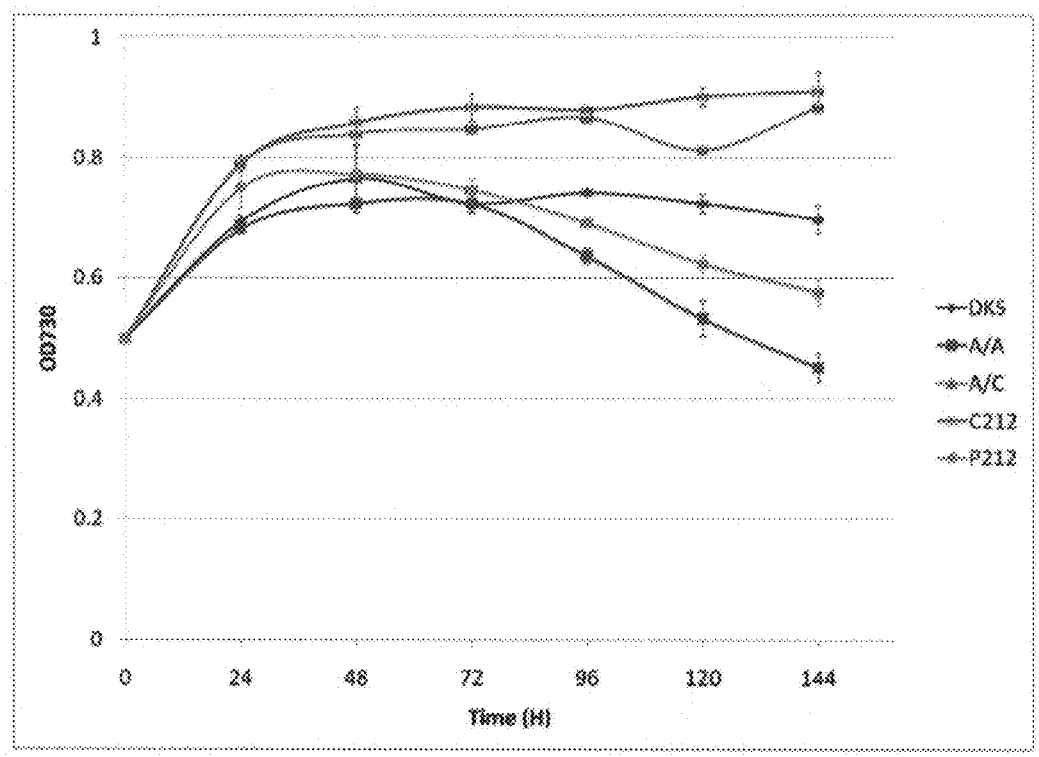
Figure 9D:
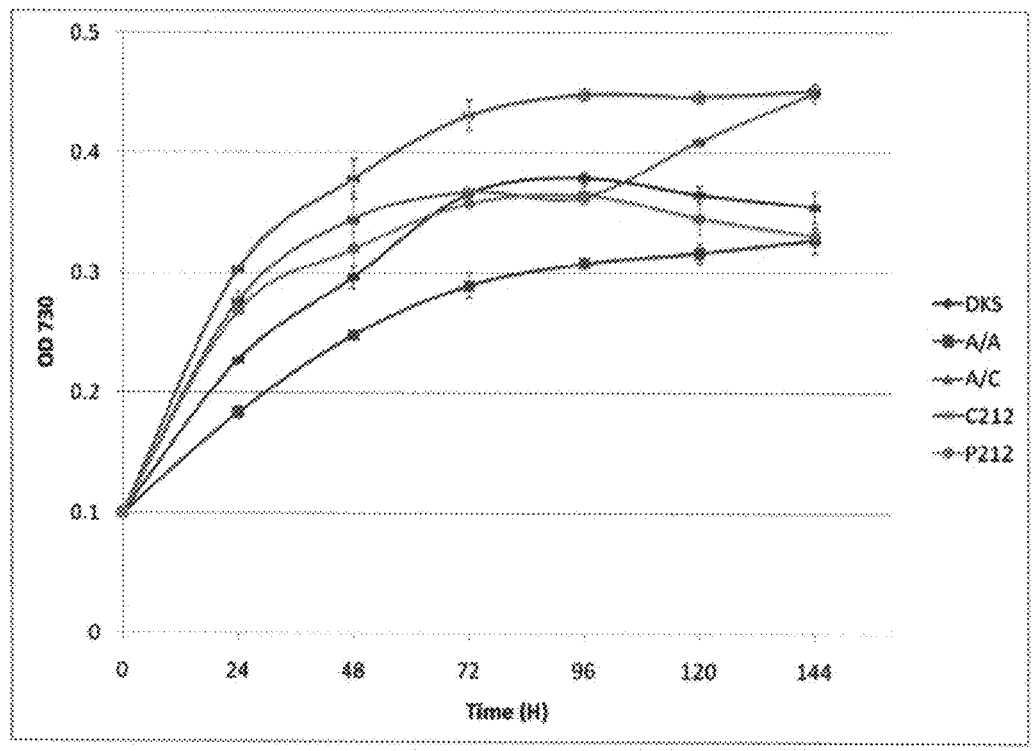
Figure 9E:
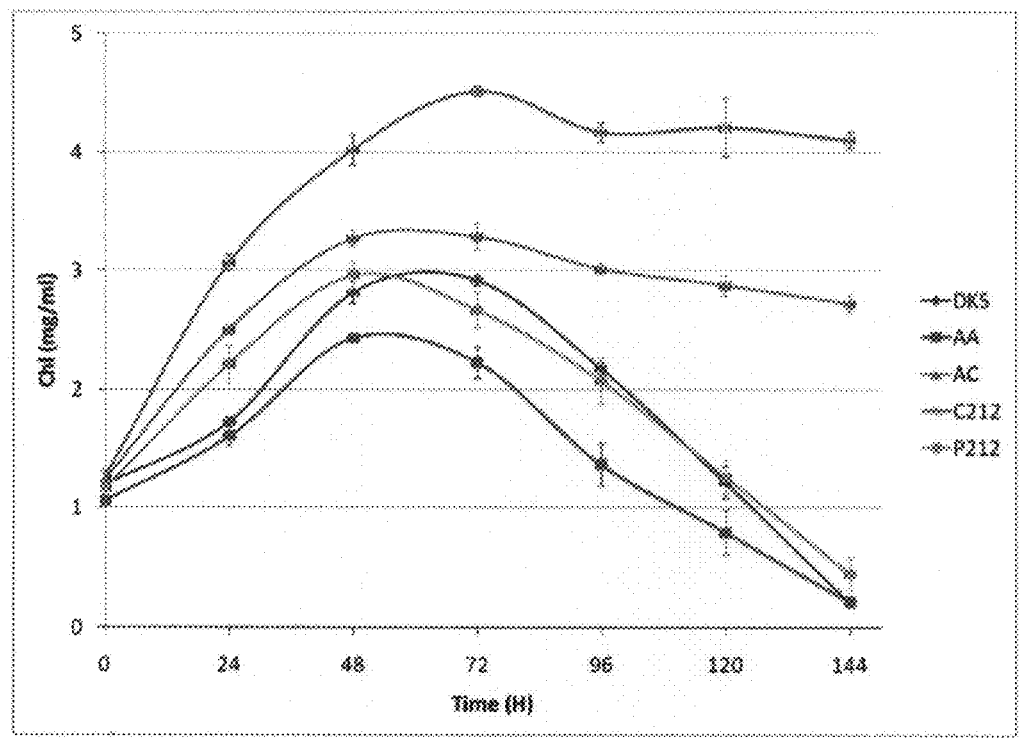
Figure 9F:
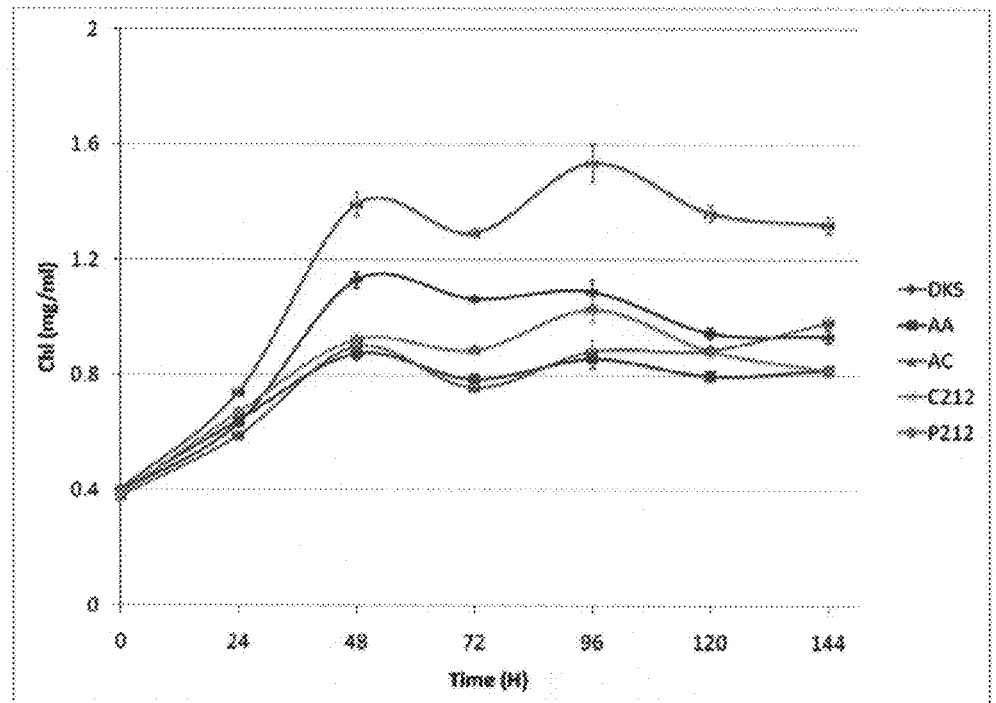

FIGS. 9A-L are graphs depicting the thermoplasticity of the wild type (ΔKS) and the different mutants under different temperature cycles (43° C.-30° C.-43° C. or 43° C.-10° C.-43° C.). FIG. 9A shows the colors of the different liquid cultures after incubation at 43° C.-30° C.-43° C.; FIG. 9B shows the colors of the different liquid cultures after incubation at 43° C.-10° C.-43° C.; FIG. 9C is a graph showing growth at 43° C.-30° C.-43° C. measured as turbidity at 730 nm; FIG. 9D is a graph showing growth at 43° C.-10° C.-43° C. measured as turbidity at 730 nm; FIG. 9E is a graph showing chlorophyll a accumulation rates in cell cultures grown at 43° C.-30° C.-43° C.; FIG. 9F is a graph showing chlorophyll a accumulation rates in cell cultures grown at 43° C.-10° C.-43° C.; FIG. 9G is an immunoblot showing the levels of D1 protein in cell cultures grown at 43° C.-30°

C.-43° C.; FIG. 9H is an immunoblot showing the levels of D1 protein in cell cultures grown at 43° C.-10° C.-43° C.; FIG. 9I is an immunoblot showing the levels of the Rubisco large protein subunit in cell cultures grown at 43° C.-30° C.; FIG. 9J is an immunoblot showing the levels of the Rubisco large protein subunit in cell cultures grown at 43° C.-10° C.-43° C.; FIG. 9K is an immunoblot showing the levels of psaC protein in cell cultures grown at 43° C.-30° C.-43° C.; and FIG. 9L is an immunoblot showing the levels of psaC protein in cell cultures grown at 43° C.-10° C.-43° C.

Figure 10A:
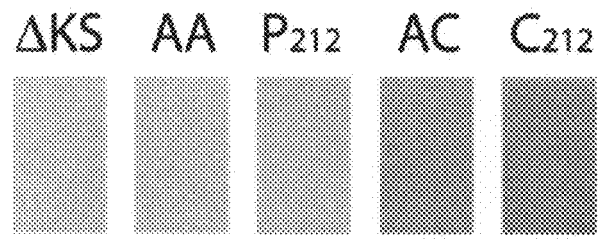
Figure 10B:
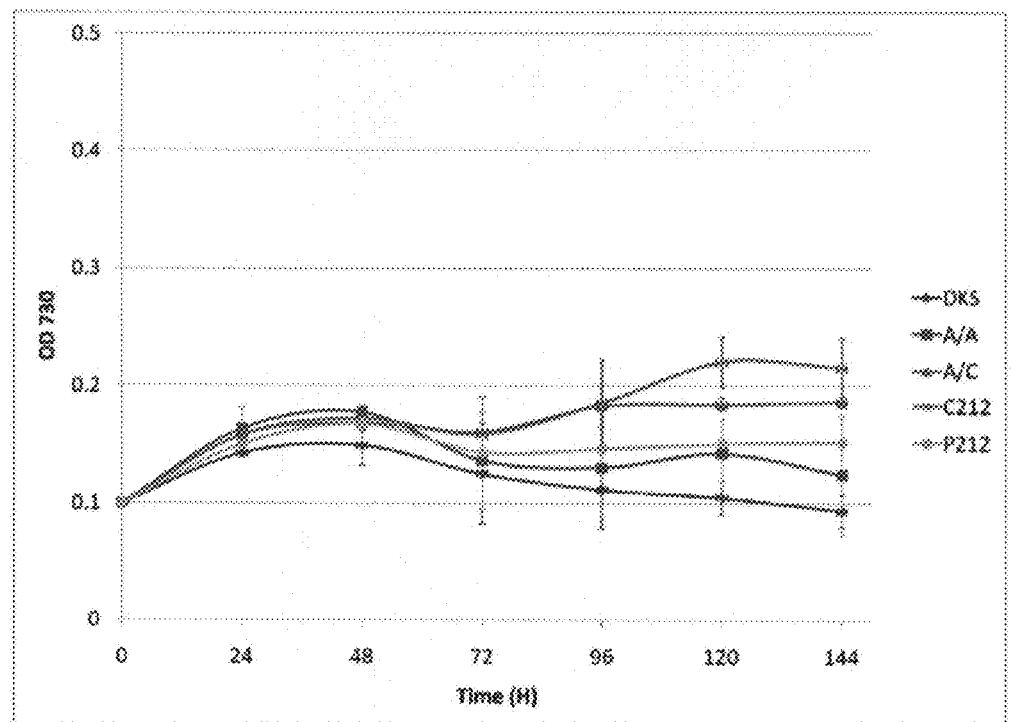
Figure 10C:
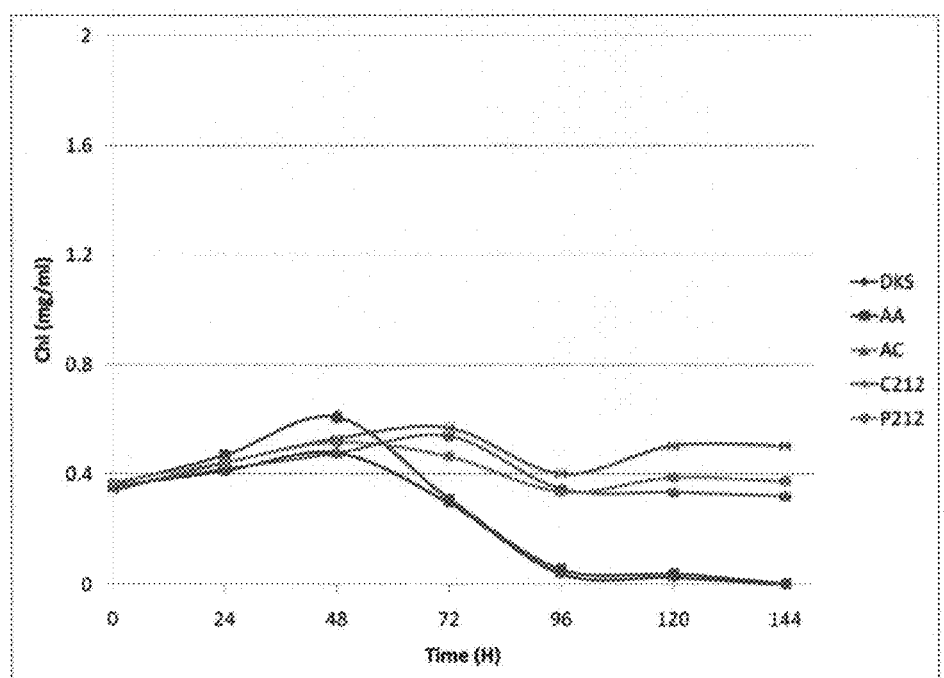
Figure 10D:
Figure 10E:
Figure 10F:
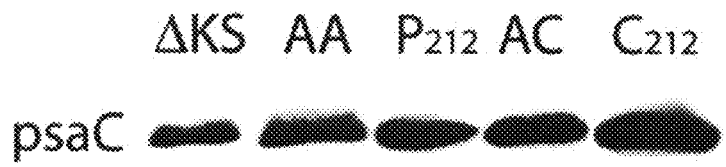

FIGS. 10A-F are graphs depicting the thermoplasticity of the wild type (ΔKS) and the different *Synechocystis* 6803 mutants and wild type cultures under 10° C.-43° C.-10° C. cycle. FIG. 10A shows the colors of the different liquid cultures after incubation; FIG. 10B is a graph showing growth measured as turbidity at 730 nm; FIG. 10C is a graph showing chlorophyll a accumulation rates in cell cultures; FIG. 10D is an immunoblot showing the levels of D1 protein in cell cultures; FIG. 10E is an immunoblot showing the levels of the Rubisco large protein subunit in cell cultures; and FIG. 10F is an immunoblot showing the levels of psaC protein in cell cultures.

DESCRIPTION OF THE PREFERRED EMBODIMENTS

The present invention is of photosynthetic organisms and, compositions and methods of generating same. Specifically, the present invention can be used to render a mesophile photosynthetic organism more thermotolerant enabling high yield of photosynthetic energy conversion at higher temperatures than the physiological temperature environment of the mesophilic organism.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Whilst conceiving the present invention, the present inventors uncovered a role of a specific amino acid sequence motif located at the D1/D2 interface of photosystem II reaction center, which contributes to functional flexibility and temperature adaptation of photosystem II reaction center (RC) in all photosynthetic organisms. This finding allowed the generation of photosynthetic organisms with "tailor-made" thermotolerance.

Thus, based on these novel findings it is now possible to increase the thermostability and thermoplasticity of photosystem II reaction center, thereby shifting maximal photosynthetic rates of the genetically modified organisms to higher temperatures, consequently enabling higher growth and/or biomass-generating rates compared with the wild type in non-optimal temperatures, e.g. by achieving a closer-to-optimum growth rates under nonphysiological conditions where such rates are suppressed. In addition, the present teachings enable photosynthetic light conversion in PSII and biomass production at wider range of temperatures, above and below that presented by wild type mesophilic strain. Furthermore, the present teachings allow maintenance of high productivity and activity of the Rubisco complex at such wider range of temperatures.

As is illustrated hereinbelow and in the Examples section which follows, whilst searching for motifs that account for the temperature adaptation of PSII RC, the present inventors examined the sequences of the two major protein subunits found in all purple bacteria and photosystem II RCs and found two sites, D1-209 and D1-212, that undergo consistent changes between mesophilic, thermotolerant and thermophilic organisms including cyanobacteria, algae and green plants (Example 1). The sites are positioned in a GxxxG-like sequence motif (where 'G' denotes small residues such as Gly, Ala, Ser, Cys and Thr) found at the closest contact of the two major protein subunits (D1 and D2 and corresponding L and M in purple bacteria for example). This motif and the structurally homologous motif in purple bacteria RC (Example 1) participates in an intersubunit hydrogen bonding (ISHB) network probably providing local flexibility while maintaining a protein overall stability. Thus, the present invention contemplates amino acid alterations within the identified GxxxG-like motif for modifying the RC localized flexibility and consequently, changing the electron transfer rate constant. Two sizable cavities augmented by several small ones complement the ISHB cluster (Example 1). Such cavities in the inner core of a protein may facilitate the conformational rearrangement required for enhancing the protein's local flexibility during discrete functional steps. Relying on the above understanding the present inventors have modified D1 of *Synechocystis* sp. 6803 in the identified domain to thereby shift the maximum PSII RC energy conversion rate of the mesophilic cyanobacteria to higher temperatures as observed when comparing mutated mesophiles with thermotolerant and thermophilic bacteria (Examples 2 and 3). Importantly, this shift is independent of the proteins and whole cell thermostability. The present inventors have further shown that some single or double mutation of the identified GxxxG motif grant thermostability over the requested temperature range (45° C.-10° C.-45° C.) while maintaining high photosynthetic productivity to mesophilic cyanobacteria (Examples 6, and 7). Since the observed GxxxG-like motif is conserved in all photosynthetic organisms (Example 1) the present teachings can be easily applied to algae, microalgae and plants to thereby establish new energy, biomass and food resources. The present inventors have further uncovered that the modified thermotolerant organisms maintain Rubisco content at higher temperature than the physiological temperature of the wild type, thus assuring carbon-dioxide fixation and biomass generation (Example 4, 5 and 7). The increased stability and functionality of PSII at high temperatures should also enable provision of thermoplasticity and enable crop growth and production in hot or warming climates.

Thus, according to one aspect of the present invention there is provided an isolated polynucleotide comprising a nucleic acid sequence encoding a polypeptide of a photosystem II reaction center of a photosynthetic organism, said nucleic acid sequence being capable of imparting said photosystem II reaction center with an activity under a temperature range (e.g., 10-50° C., 10-43° C. or 30-43° C.) different than that of said type II reaction center endogenous to said photosynthetic organism.

As used herein the phrase "photosynthetic organism" refers to an organism (prokaryote or eukaryote) capable of converting light energy and a carbon source (e.g., carbon dioxide) to triose phosphates.

The photosynthetic organism of this aspect of the present invention can be a mesophile, a thermophile and a psychrophile.

As used herein the phrase "mesophile organism" refers to an organism with a physiological growth temperature at a range of about 15-35° C.

As used herein the phrase "thermotolerant organism" refers to an organism with a physiological growth temperature at a range of about 35-45° C.

As used herein the phrase "thermophile organism" refers to an organism with a physiological growth temperature at a range of about 45-70° C.

As used herein the phrase "psychrophile organism" refers to an organism with a physiological growth temperature at a range of about 0-15° C.

Thus, the photosynthetic organism of this aspect of the present invention refers to a bacteria (aerobic and anaerobic), an algae (prokaryotic and eukaryotic) and a higher plant.

Examples of photosynthetic bacteria include without limitation cyanobacteria e.g Synechocystis sp. PCC 6803, Prochlorothrix hollandica, Thermosynechococcus elongatus, purple non sulfur e.g., Rhodospirillum rubrum Rhodobacter sphaeroides, Rhodopseudomonas viridis and green non sulfur photosynthetic bacteria e.g., Chloroflexus aurantiacus.

Examples of algae include without limitation green algae e.g., Chlamydomonas reinhardtii, Chlorella vulgaris and red algae e.g. Cyanidium caldarium, Porphyridium purpureum.

Examples of plants [The term "plant" as used herein encompasses whole plants, ancestors and progeny of the plants and plant parts, including seeds, shoots, stems, roots (including tubers), and plant cells, tissues and organs. The term "plant" also therefore encompasses suspension cultures, embryos, meristematic regions, callus tissue, leaves, etc.]. include in particular monocotyledonous and dicotyledonous plants which are of commercial value, including a fodder or forage legume, ornamental plant, food crop, tree, or shrub selected from the following non-limiting list comprising maize, sweet potato, tubers such as cassarva, sugar beet, wheat, barely, rye, oat, rice, soybean, peanut, pea, cowpea, lentil and alfalfa, cotton, rapeseed, canola, pepper, sunflower, potato, tobacco, tomato, eggplant, trees such as eucalyptus and poplars, an ornamental plant, a perennial grass and a forage crop.

As used herein the phrase "photosystem II reaction center" or a "type II reaction center" refers to eukaryotic and prokaryotic type II reaction centers. The photochemical reaction center (RC) of photosystem II (PSII, the D1-D2 cyt.b559complex) is the smallest unit in PSII that shows photochemical activity. The RC contains 8 chlorophyll (Chl) a and two pheophytin (Pheo) a molecules that all have their lowest electronic transition around 675 nm, as well as two β-carotenes. The D1 and D2 polypeptides are homologous to the L and M subunits of bacterial RCs, suggesting an arrangement of the core pigments in the RC of PSII similar to that in the bacterial RC. The two additional Chl molecules are probably located near the periphery of the D1-D2 complex.

As used herein the phrase "activity of a photosystem II reaction center" refers to a solar energy conversion activity which is essential for the photosynthetic organism. A number of proxies can be used to determine the activity of the photosystem II reaction center. Examples include, but are not limited to, growth rate, viability, chlorophyll concentration, $Q_A$-$Q_B$ electron transfer rate and Rubisco levels. Assays for qualification/quantification are described at length in the Examples section which follows.

As used herein the phrase "a polypeptide of a photosystem II reaction center" refers to D1, D2, L and M (see SEQ ID NOs. 30-34 and 36). Exemplary GenBank Accession Numbers are provided in FIG. 1C.

As mentioned herein above, the present inventors have identified a nucleic acid sequence motif GXXXG (corresponding to positions 208-212 of SEQ ID NO: 36), on D1 (located at the D1/D2 interface) which contributes to the functional flexibility and temperature adaptation of photosystem II reaction center.

Thus, according to an exemplary embodiment of this aspect of the present invention the nucleic acid sequence encodes a polypeptide having an amino acid sequence alteration at a position corresponding to 209 of SEQ ID NO: 36 and at a position corresponding to 212 of SEQ. ID NO: 36 (e.g., see SEQ ID NOs. 37-61).

According to other exemplary embodiments the isolated polypeptide sequences of D2, L and M polypeptides SEQ ID NO: 30-SEQ ID NO: 34 with suggested sites for mutations for D2 polypeptide at a positions corresponding to 207 and 211 in Synechocystis sp 6803 (SEQ ID NO: 30); for M polypeptide at positions corresponding to 211 and 215 in Rhodopseudomonas viridis (SEQ ID NO: 31) and 213 and 217 in Rhodobacter sphaeroides (SEQ ID NO: 32); for L polypeptide at positions corresponding to 184 and 188 in both Rh.viridis and Rh.sphaeroides (SEQ ID NOs. 33 and 34).

Thus, the present inventors have shown that Synechocystis sp. 6803 modified with a polynucleotide of the present invention encoding a D1 polypeptide with a serine to alanine substitution at a position corresponding to 209 of SEQ ID NO: 36 and/or a serine to cysteine substitution at a position corresponding to 212 of SEQ ID NO: 36 imparts the modified photosystem II RC with an activity under non-physiological temperature [e.g., upwards shift in temperature conditions of (e.g., 30>43° C.)].

As used herein the phrase "physiological conditions" refers to a temperature range which mediates optimal growth (e.g., +/−50%) of the naïve (non-genetically modified) organism.

Thus, according to one embodiment of this aspect of the present invention the isolated polynucleotide (or an expression product of same i.e., the isolated polypeptide) of this aspect of the present invention is capable of rendering the photosystem II reaction center which comprises same more thermotolerant as compared to a non-modified reaction center.

According to another embodiment of this aspect of the present invention the isolated polynucleotide (or an expression product of same i.e., the isolated polypeptide) of this aspect of the present invention is capable of rendering the photosystem II reaction center which comprises same more thermoplastic as compared to a corresponding non-modified reaction center.

According to yet another embodiment of this aspect of the present invention, the polynucleotide is capable of imparting the photosystem II reaction center with an activity at an upwards shifted range (e.g., at least 4° C., 6° C., 7° C. or 10° C. higher than that of a corresponding non-modified type II reaction center).

According to a still embodiment of this aspect of the present invention, the polynucleotide is capable of imparting the photosystem II reaction center with an activity at an downwards shifted range (e.g., at least 2.5° C. or 4° C. lower than that of a corresponding non-modified type II reaction center).

According to a further still embodiment of this aspect of the present invention, the polynucleotide is capable of imparting the photosystem II reaction center with an activity at an downwards shifted range (e.g., at least 2.5° C. or 4° C. lower than that of a corresponding non-modified type II reaction center).

According to a further still embodiment of this aspect of the present invention, the polynucleotide is capable of imparting the photosystem II reaction center with biomass productivity at a wider temperature range (e.g., at least 10° C. wider than that of a corresponding non-modified type II reaction center).

The nucleic acid sequence (also termed herein as "isolated polynucleotide") of the present invention refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Nucleic acid sequences of the polypeptides of the present invention may be optimized for plant expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn]2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (http://www.kazusa.or.jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Since the present invention provides previously unknown polypeptides, the present invention also encompasses polypeptide sequences, fragments of the above described polypeptides and polypeptides having mutations, such as deletions, insertions or substitutions of one or more amino acids, either naturally occurring or man induced, either randomly or in a targeted fashion.

Methods of identifying mutations which impart a photosynthetic organism with a photosynthetic activity under a non-physiological temperature are outlined infra. Basically, subjecting the photosynthetic organisms to a mutagen, so as to obtain mutated photosynthetic organisms. Identifying an organism of said mutated photosynthetic organisms exhibiting at least one parameter associated with enhanced photosynthetic activity under non-physiological temperature as compared to corresponding wild type photosynthetic organisms. Identifying mutations in a polypeptide of a photosystem II reaction center of said organism, said mutations being correlated with photosynthetic activity under a non-physiological temperature.

Exemplary parameters which are associated with photosynthetic activity include, but are not limited to, biomass, growth rate, rubisco level, chlorophyll content, psaC level and thermoplasticity.

Polynucleotides and polypeptides of the present invention are used for expression in a cell of a photosynthetic organism.

The expression system will naturally depend on the organism.

Methods of expressing the nucleic acid sequences of this aspect of the present invention in photosynthetic bacteria are well known in the art and described at length in the Examples section which follows. Generally these include site-directed mutagenesis and methods of transgenesis.

Methods of expression of exogenous polynucleotides in microalgae are well known in the art. See for example WO2006/013572 incorporated herein by reference in its entirety.

Expressing the exogenous polynucleotide of the present invention within higher plants can be effected by transforming one or more cells of the plant with the exogenous polynucleotide, followed by generating a mature plant from the transformed cells and cultivating the mature plant under conditions suitable for expressing the exogenous polynucleotide within the mature plant.

Preferably, the transformation is effected by introducing to the plant cell a nucleic acid construct which includes the exogenous polynucleotide of the present invention and at least one promoter capable of directing transcription of the exogenous polynucleotide in the plant cell. Further details of suitable transformation approaches are provided hereinbelow.

As used herein, the term "promoter" refers to a region of DNA which lies upstream of the transcriptional initiation site of a gene to which RNA polymerase binds to initiate transcription of RNA. The promoter controls where (e.g., which portion of a plant, which organ within an animal, etc.) and/or when (e.g., which stage or condition in the lifetime of an organism) the gene is expressed.

Any suitable promoter sequence can be used by the nucleic acid construct of the present invention. Preferably the promoter is a constitutive promoter.

Suitable constitutive promoters include, for example, CaMV 35S promoter.

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

The nucleic acid construct of the present invention preferably further includes an appropriate selectable marker and/or an origin of replication. Preferably, the nucleic acid construct utilized is a shuttle vector, which can propagate both in E. coli (wherein the construct comprises an appropriate selectable marker and origin of replication) and be compatible for propagation in cells. The construct according to the present invention can be, for example, a plasmid, a bacmid, a phagemid, a cosmid, a phage, a virus or an artificial chromosome.

The nucleic acid construct of the present invention can be utilized to stably or transiently transform plant cells. In stable transformation, the exogenous polynucleotide of the present invention is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) Agrobacterium-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The Agrobacterium system includes the use of plasmid vectors that contain defined DNA segments that integrate into the plant genomic DNA. Methods of inoculation of the plant tissue vary depending upon the plant species and the Agrobacterium delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the Agrobacterium delivery system in combination with vacuum infiltration. The Agrobacterium system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Preferably, mature transformed plants generated as described above are further selected for increase biomass, alcohol production, vigor and/or yield.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Preferably, the virus of the present invention is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous polynucleotide sequences such as those included in the construct of the present invention is demonstrated by the above references as well as in U.S. Pat. No. 5,316,931.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Photosynthetic organisms generated according to the teachings described hereinabove may be rendered more thermoplastic than an identical photosynthetic organism not comprising the exogenous nucleic acid sequence of the present invention.

Alternatively or additionally, the photosynthetic organism of the present invention may be capable of expressing more Rubisco than an identical photosynthetic organism not comprising the exogenous nucleic acid sequence of the present invention.

Yet alternatively or additionally, the photosynthetic organism of the present invention may be capable of expressing more psaC than an identical photosynthetic organism not comprising the exogenous nucleic acid sequence of the present invention.

Still alternatively or additionally, the photosynthetic organism of the present invention may grow faster than a photosynthetic organism not comprising the exogenous nucleic acid sequence of the present invention.

Still alternatively or additionally, the photosynthetic organism of the present invention may be accumulating more chlorophyll than an identical photosynthetic organism not comprising the exogenous nucleic acid sequence.

Thus, the present teachings may be used to increase activity of a photosystem II reaction center of a photosynthetic organism under non-physiological temperature.

As used herein the phrase "non-physiological temperature" refers to a temperature which does not mediate ultimate growth of the non-genetically modified photosynthetic organism (e.g., at least about 70% reduction in photosynthetic activity). This may be achieved by introducing into the photosynthetic organism the polynucleotide of the present invention and growing it in the non-physiological temperature, thereby increasing the activity of the photosystem II reaction center under a non-physiological temperature.

The present teachings allow for improving biomass/vigor/yield of a photosynthetic organism comprising the nucleic acid sequence of the present invention, preferably when grown under non-physiological temperature (abiotic stress condition xxx e.g., heat and/or alternating temperatures).

As used herein the phrase "biomass" refers to the amount or quantity of tissue (in particular cellulose comprising tissue) produced from the photosynthetic organism in a growing season, which could also determine or affect the photosynthetic organism yield or the yield per growing area.

As used herein the phrase "vigor" refers to the amount or quantity of tissue produced from the photosynthetic organism in a given time. Hence increase vigor could determine or affect the photosynthetic organism yield or the yield per growing time or growing area.

As used herein the phrase "yield" refers to the amount or quantity of tissue produced and harvested as the photosynthetic organism produced product. Hence increase yield could affect the economic benefit one can obtain from the photosynthetic organism in a certain growing time.

Methods of determining biomass, yield and vigor are well known in the art and further described in Coleman et al, 2006, Plant Biotechnology Journal 4 (1), 87-101.

As used herein the term "improving" or "increasing" refers to improving or increasing the biomass/yield/vigor of the photosynthetic organism of the present invention by at least about 2% more, 5% more, 10% more, 20% more, 30% more, 40% more, 50% more, 60% more, 70% more, 80% more, 90% or more than that of the non-transgenic photosynthetic organism (e.g., mock transfected, or naïve).

As it has recently been suggested that temperature is the most important parameter for hydrogen production (Tsygankov 1999 Biotechnol. Bioeng. 64:709-15), the present invention also contemplates use of the photosynthetic organisms provided herein for hydrogen production.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

PCR-Based Mutagenesis of the Synechocystis 6803

The psbAII gene mutation at positions 634-636, corresponding to D1-Ser212, was inserted using combinatorial DopA/DopB primers (Table 1 hereinbelow) coding for 16 residues at this site. The oligonucleotides P5, P3, P209 and P212 were designed to match known sequences in the psbAII gene (Table 1). The NsiI restriction site modification was introduced in the third codon downstream to the 212 loci; facilitating screening of the transformant colonies. The final PCR product was used to transform the recipient strain ΔSRS268-270 in the psbAII gene as previously described [Kless and Vermaas, Biochemistry 35, 16458-16464 (1996)]. Specific X212 oligonucleotides were designed to introduce codons in the D1-212 site corresponding to (Gly, Lys, His, Phe, Trp, Tyr, Arg, Met, Asp, Gln, and Glu) amino acids that were not obtained or introduced by the combinatorial mutagenesis approach. Additionally S209/212 nucleotide was prepared to insert degenerate sequence at 625-627, corresponding to D1-Ser209 and at 634-636 corresponding to D1-Ser212 sites to obtain double D1-209/212 mutants.

TABLE 1

Oligonucleotides used in mutagenesis

| Oligonucleotides[a] | Nucleotide Sequences[b] | Gene Position[c] |
|---|---|---|
| DopA[d] SEQ ID NO: 1 | CGGTGGTAGCTTGTTCYDBGCC<u>ATGCAT</u>GGTTCC | 618-651 |
| DopB[d] SEQ ID NO: 2 | CGGTGGTAGCTTGTTCVHWGCC<u>ATGCAT</u>GGTTCC | 618-651 |
| P212 SEQ ID NO: 3 | GAACAAGCTACCACCGAATACACCAGC | 633-607 |
| P3 SEQ ID NO: 4 | GGATTAATTCTCTAGACTCTCTAATGG1 | 233-1179 |
| P5 SEQ ID NO: 5 | CCAAAACGCCCTCTGTTTACC | (-187)-(-166) |
| P260 SEQ ID NO: 6 | GCCGTGGGCGGCAACGATGTTGTAGG | 759-734 |
| P4 SEQ ID NO: 7 | CTTCCACATGTTAGGTGT | 588-605 |

TABLE 1-continued

Oligonucleotides used in mutagenesis

| Oligonucleotides[a] | Nucleotide Sequences[b] | Gene Position[c] |
|---|---|---|
| P209 SEQ ID NO: 8 | ACCACCGAATACACCAGCCACACCTAA | 624-598 |
| X212[e] SEQ ID NO: 9 | CGGTGGTAGCTTGTTCxxxGCC<u>ATGCA*T*</u>GGTTCC | 618-651 |
| S209/212 SEQ ID NO: 10 | GGTGTATTCGGTGGTNNSTTGTTCNNSGCC<u>ATGCA*T*</u>GGTTCC | 610-651 |

[a]The P260 and P4 oligonucleotides were used for sequencing the PCR product.
[b]Oligonucleotides are listed in a 5' to 3' direction. Restriction sites of NsiI introduced as silent mutations are underlined, and the modifications are in italics.
[c]psbAII numbering as described.
[d]The universal code for degenerate oligonucleotides is Y(C, T); D(g, A, T); B(g, T, C); V(g, A, C); H(A, T, C); W(A, T); N(A, T, C, g); S(C, g).
[e]The xxx represents specific codons for Trp (TGG), Tyr (TAC), Phe (TTT), Arg (CGG), Gln (CAA), Glu (GAA), His (CAC), Asp (GAT), Lys (AAA), Gly (GGT) and Met (ATG).

*Synechocystis* sp. PCC6803 Growth Conditions

*Synechocystis* sp. PCC 6803 cells were grown in BG-11 mineral medium as previously described [Williams, *Methods in Enzymology* 167, 766-778 (1988)]. All wild type and mutant strains were maintained on 1.5% agar (Difco) plates in the presence of 5 µg/ml kanamycin (Monosulfate, Sigma). Five mM glucose was routinely added to plates to maintain PSII-independent growth. To get liquid cultures suitable for measurements, cells were scratched from the plates and transferred into a stirred 50 ml BG-11 liquid medium in the absence of glucose for one day growth in order to get fresh starter culture. Liquid cultures were grown on gyratory shaker (200 rpm) at 30° C. and 40 µmol (photons) $m^{-2}s^{-1}$ of white light. The growth chamber was aerated with fresh air. Cells for the photosynthetic measurements were transferred into stirred 250 ml BG-11 medium at the same conditions and harvested at the end of the logarithmic growth phase corresponding to a chlorophyll concentration of 4-7 µg/ml.

Temperature Treatments

Cells grown for 3 days were diluted or concentrated to an $OD_{730}=0.5$ with fresh medium prior to treatments. Cultures of the similar cell density were transferred to 30° C. or 43° C. (same light conditions) for 7 days. For the plasticity test, cultures having $OD_{730}=0.5$ were incubated at a 43° C.-30° C.-43° C., 10° C.-43° C.-10° C. or 43° C.-10° C.-43° C. cycle for 48 hours at each temperature.

Pigment Analysis

Pellets of the cells grown in liquid cultures were extracted in 90% methanol. The chlorophyll concentration was determined spectroscopically with Jasco V530 spectrophotometer (Jasco, USA) using the molar extinction coefficient determined by Lichtentaller [Wellburn and Lichtenthaler, *Advances In Photosynthesis Research* Vol. II (1984)]. The carotenoid content was analyzed with Smartline HPLC system (Knauer, Germany) using Jupiter HPLC column (15 µm particle size, C18, 300 Å pore size, 250×15 mm, Phenomenex, USA) according to the procedure previously described [Pocock et al., *Methods Mol Biol* 274, 137-48 (2004)].

Growth Rate Measurements

The growth rates were measured in terms of optical density at 730 nm (OD 730) in aliquots obtained from the liquid cultures every 24 hours. Cell density was estimated by turbidometry, measuring light attenuation at 730 nm after diluting cultures to OD values less than 0.5, where turbidity is roughly proportional to cell concentration.

Isolation of Thylakoid Proteins and Western Blot Analysis

Thylakoid membranes were isolated according to the method previously described by Callahan [Callahan et al., *J Biol Chem* 265, 15357-60 (1990)]. Thylakoid proteins were solubilized in sample buffer [0.5 M Tris-HCl pH 6.8, 1% SDS, 24% glycerol, 4% β-mercaptoethanol, 0.001% (w/v) Bromophenol blue], incubated at room temperature for 1 hour and then separated by SDS-PAGE 12.5%. The equivalent of 2.5 µg of chlorophyll was loaded into each well. Proteins were electroblotted to PVDF (Hybond-P, Amersham) using a Bio-Rad Mini Transblot Cell (Bio-Rad, Hercules, Calif., USA). The immunodetection was carried out using a chemiluminescence kit (Pierce). Antibodies against D1, psaC and RbcL proteins were purchased from Agrisera (Umeå, Sweden).

Measurement of the Temperature Dependence of the $Q_A^-Q_B$ Electron Transfer Rate The temperature dependence for the $Q_A^-Q_B$ electron transfer rate was assessed by measurements the chlorophyll Chl a fluorescence as recently described [Shlyk-Kerner et al., *Nature*, 442(7104): 827-30 (2006)]. Three days old liquid cultures were diluted by BG-11 medium to 5 µM of chlorophyll and dark adapted for at least 30 minutes on ice prior to fluorescence measurements. Aliquots of 3 ml cell suspension were then placed into polystyrene cuvettes (Sigma) and adapted to a selected temperature for 5 minutes in the dark. The measurements of Chl a fluorescence were performed with FL-3000 double-modulation fluorometer equipped with TR 2000 thermoregulator (P.S. Instruments Inc., Czech Republic). The re-oxidation kinetics of $Q_A^-$ was measured as the decay of Chl a fluorescence following the single-turnover saturating flash (25 µs duration, λ=630 nm) that reduced all $Q_A$ in the sample into $Q_A^-$. The variable fluorescence decay, reflecting the re-oxidation of $Q_A^-$ was measured on the logarithmic time scale to minimize the perturbation of the sample. The normalized decay kinetic curves were fitted by least-squares numerical analysis to a three-exponential function. The highest rate constant was assigned to the electron transfer from $Q_A^-$ to $Q_B$, as described by Nedbal et al. [Nedbal et al., *Journal of Photochemistry and Photobiology B: Biology* 48, 154-157 (1999)]. Data from at least ten individual experiments were averaged. Importantly, the fluorescence analysis as used allowed for discrimination between active and inactive PSII reaction centres [Joshi and Fragata, *Z Naturforsch [C]* 54, 35-43 (1999)]. The inactive centres contribute to the longest lifetime component and become apparent at temperatures well above the physiological range [Joshi and Fragata, supra].

In Silico Analysis

Intra-Molecular Cavity Analysis (Protein Cavities):

Cavity analysis was conducted with VOLBL [Liang et al., *Proteins* 33, 18-29 (1998); Liang et al., *Proteins* 33, 1-17 (1998)] using the standard 1 Å-radius probe used for cavities. Proteins were analyzed without hydrogens. The addition of hydrogens caused a reduction of up to 30% in cavity size (data not shown). Notably, the binding niche of the cofactors was surrounded by a number of cavities. As the study was confined to the area within the four-helix-bundle transmembrane core of the protein, only cavities that were lined solely by atoms from the D and E helices were represented.

Evolutionary Conservation of the GxxxG-Like Motif in RC Subunits of Thermophilic, Thermotolerant and Psychrophilic Organisms:

The conservation level of photosystem II RC was assessed by (a) searching the BLOCKS [Henikoff et al., *Nucleic Acids Res* 28, 228-30 (2000)] database with the D1 sequence of *Synechocystis* 6803; and (b) searching sequence space with PSI-BLAST [Altschul et al., *Nucleic Acids Res* 25, 3389-402 (1997)], using both the original D1 sequence and the representative sequence (Cobbler sequence) from the Blocks database [Henikoff et al., supra]-block IPB000484B. In addition, newly sequenced relevant organisms were searched via the Entrez Genome Project, and a Blast search (using TBLASTN2.1.2) was conducted against cyanobacteria and plant sequences that have not been fully annotated into DNA databases and in designated databases such as CyanoBase [Nakamura et al., *Nucleic Acids Research* 26, 63-67 (1998)].

Hydrogen Assignment and Hydrogen Bond Analysis:

Hydrogens were added to the structure using REDUCE [Word et al., *J Mol Biol* 285, 1711-33 (1999)], and intersubunit H-bonds were screened using an in-house program [Goldberg, M.Sc. thesis, Weizmann Institute of Science (2004)] following geometric criteria [Senes et al., *Proc Natl Acad Sci USA* 98, 9056-61 (2001)] for putative bonds. The geometric criteria included: DH<3.5 Å and DH-A angle>120° (or DH-A angle>100° if DH<3 Å) where D, A, and DH were the donor atom, acceptor atom and hydrogen found on the donor atom. These constraints, particularly the allowed D/A pair distance and DH-A angle, were more relaxed than those given by Desiraju [Desiraju, *Acc Chem Res* 35, 565-73 (2002)]. The constraints were used to ensure that under the non-ideal resolution of the structures analyzed all potential H-bonds were captured. Several interactions were depicted in which the DH-A and/or angle thresholds were not satisfied. Alternatively, in some cases the H-bond flip between two positions but cannot occupy both simultaneously. These interactions were given to demonstrate the close intersubunit packing in this region.

Graphical Representation of Structural Motifs:

Structures were drawn with PyMol (Warren L. DeLano "The PyMOL Molecular Graphics System." DeLano Scientific LLC, San Carlos, Calif., USA. (www dot pymol dot org). In order to replicate the result of the VOLBL [Liang et al., *Proteins* 33, 18-29 (1998); Liang et al., *Proteins* 33, 1-17 (1998)] cavity analysis program, atom radii were changed to the OPLS-derived van der Waals radii as applied in VOLBL, and found in the param dat file. In order to confine the surface representation to the cavities, pseudo atoms were inserted into the cavities. Next, the surface_carve_selection function was used to confine the surface represented to the area adjacent to these pseudo atoms. The surface was represented using a command such as "show surface, protein and (pseudo_atoms expand 3)". This resulted with surface representation of the cavity but also pieces of other cavities found around the cofactors' binding niche. In order to eliminate the latter from the drawing, the van der Waals radii of the cofactor atoms was set to a large enough number.

Non-Conserved Positions at D1-209 and D1-212 Loci of Additional, Hydrogen Generated Cyanobacteria 1. D1(Ser209)Ala—(locus: YP_476691, gi: 86607929) from extremophilic cyanobacterium Yellowstone B-Prime known also as *Synechococcus* sp. strain JA-2-3B'a(2-13). The A-Prime strain has the same sequence in this region (locus: YP_474719, gi: 86605956).

2. D1(Ser209)Ala—(locus: ABA21206, gi: 17132876)-*Nostoc* (or *Anabena*) sp PCC 7120—mesophilic, nitrogen fixing cyanobacterium.

3. D1(Ser209)Ala—(locus: BAB75441, gi: 75701530)—*Anabaena variabilis* ATCC 29413—mesophilic, nitrogen fixing, hydrogen producing cyanobacterium.

4. D1(Ser209)Ala—(locus: EAQ69357, gi: 86168099)—*Synechococcus* sp. RS9917—halotolerant cyanobacterium.

5. D1(Ser209)Ala,(Ser212)Ala—PSBA-2 (Swissprot: PSBA2_SYNEN or PSBA2_SYNEL), one of the two psbA genes from the thermophilic cyanobacterium *Synechococcus elongatus naegeli*.

6. D1(Ser209)Ala,(Ser212)Cys—PSBA-1 (Swissprot; PSB1_SYNVU), thermophilic cyanobacterium *Synechococcus vulcanus*.

7. D1(Ser212) Cys—PSBA-1, (TrEMBL; Q9S3W5)—true branching filamentous thermophilic cyanobacterium *Mastigocladus laminosus*.

8. D1(Ser209)Ala,(Ser212)Ala—PSBA-1 (Swissprot PSB1—SYNY3, *Synechocystis* sp. PCC 6803). Notably, this PSBA-1 is not expressed on a constitutive level but is expressed under high-light-stimulated transcription. Thus, it may represent an adaptation to stress conditions.

9. D1(Ser209)Ala,(Leu210)Phe(Ser212)Cys—(locus: ZP_00108645, gi: 23126757) *Nostoc punctiforme* sp. PCC 73102—mesophilic, nitrogen fixing cyanobacterium.

Non-Conserved Positions at the D1-209 and D1-212 Loci in Microalgea

1. In the thermotolerant red alga *Cyanidium caldarium*, the D1-Ser209 has been modified to D1-Ala209—PSBA-1 (Swissprot: PSBA_CYACA) (thrives at temperature higher than 45° C., pH=1 and/or high salinity).

2. D1(Ser209)Ala—(locus: NP_848970, gi: 30468083) in thermo-acidophilic unicellular red alga *Cyanidioschyzon merolae* strain 10D that is found in acidic hot springs (locus: AAM62037, gi: 21913561).

3. D1(Ser209)Ala—(locus: AAR30280, gi: 39753030) in thermo-acidophilic unicellular red alga *Galdieria maxima* from acidic hot springs.

4. D1(Ser209)Ala—(locus: AAZ59080, gi: 72003278)—*Prochlorococcus marinus* str. NATL2A—dominates phytoplankton in tropical and subtropical oceans.

Example 1

Protein Flexibility Acclimatizes Photosynthetic Energy Conversion to the Ambient Temperature Solar energy conversion in reaction centers (RC) from non-oxygenic purple bacteria and from photosystem II (PSII) of oxygenic organisms is initiated by means of a multi-step, light-induced electron transfer (ET) across the photosynthetic membrane (FIG. 1A). The process ends in the reduction of a quinone molecule ($Q_B$) by another quinone ($Q_A$) accompanied by imperative reorganization and mobilization of protons. Former studies of this reaction showed that protein flexibility and a conformational change are required to set on the $Q_A \rightarrow Q_B$ ET, that the rate constant, k, is independent of the quinones' redox energies, and that the reaction should be accelerated at elevated temperatures [Okamura et al., *Biochim Biophys Acta* 1458, 148-63 (2000); Li et al., *Biochemistry* 37, 2818-29 (1998); Xu et al., *Biochemistry* 41, 2694-701 (2002)]. Following the classical Arrhenius paradigm, k is expected to increase exponentially with 1/T at a pace equal to $\Delta H^{\ddagger}/R$ where $\Delta H^{\ddagger}$ is the enthalpy of ET activation. However, inventors observed that this prediction was violated in intact cells of mesophilic and thermophilic cyanobacteria (FIG. 2A). Here, k levels off at $T_o$ slightly below the growth temperature of the examined organisms ($T_o=26°$ C. and $T_o=59°$ C., for mesophilic and thermophilic strains, respectively), the rate became temperature independent throughout the entire physiological range and then slightly decreased. In all strains, k reached a similar maximum value of ~3000-3500 sec-1. In the thermo-tolerant organism *Cyanidium caldarium* it reached the same value but at $T_o=43°$ C. (data not shown). $T_o$ was significantly lower from the reported denaturation temperature of the RC (higher than 40° C. in mesophiles [Joshi et al., *Zeitschrift Fur Naturforschung C-a Journal of Biosciences* 54, 35-43 (1999)]) ruling it out as the origin for the observed phenomenon (FIG. 6, further explained in detail hereinbelow).

Thus, the photosynthetic organism appeared to utilize novel physico-chemical principles to slow down the rate acceleration at elevated temperature. Remarkably, the activation enthalpies ($\Delta H^{\ddagger}$) below $T_o$ for the examined mesophile and thermophile were almost identical (FIG. 2A). However, the activation entropies ($\Delta S^{\ddagger}$) for the thermophilic *Thermosynechococcus elongatus* was more negative by ~1 kcal·mol$^{-1}$ suggesting that flexibility of the RC excited state was a key player in the temperature adjustment of the energy conversion rate.

In search for motifs that account for the observed differences in the activation entropies, inventors examined the sequences of the two major protein subunits by sequence alignment of the D helices in RC found in all photosystem II RCs and in purple bacteria (FIGS. 1A-C).

Rather than searching in proximity to the cofactor-binding sites, inventors confined the search to the four transmembrane-helices that physically hold the electron transfer cofactors. Two sites, D1-209 and D1-212, were found to undergo consistent changes between mesophilic, thermotolerant and thermophilic organisms including cyanobacteria, algae and green plants. These sites, positioned in a GxxxG-like sequence motif (gray background, FIG. 1C), where 'G' denotes small residues such as Gly, Ala, Ser, Cys and Thr, were found at the closest contact of the two major protein subunits (D1 and D2, FIG. 1C). This motif and the structurally homologous motif in purple bacteria was found at the center of the transmembrane (TM) domain, where the D and E helices of the two major RC subunits of photosystem II (D1 and D2) and bacterial RC (L and M) maintain a conserved intersubunit hydrogen bonding (ISHB) network (FIGS. 1A-B, 5A-E and Table 2). ISHB was suggested to provide local flexibility while maintaining overall stability.

TABLE 2

Potential ISHBs Involving the Transmembrane Regions of the D and E in the RC of Purple Bacteria and Photosystem II

| | Organism | PDB/Ref | Res. (Å) | HB Donor | HB Acceptor | D-A | DH-A | Angle |
|---|---|---|---|---|---|---|---|---|
| Bacterial RC | *R. sphaeroides* | 1m3x[87] | 2.55 | M-Ala213CA | L-Ser237OG | 3.7 | 2.9 | 131 |
| | | | | L-Asn183ND2 | M-Ser212O | 3.3 | 2.3 | 152 |
| | | | | M-Gly220CA | L-His230O | 3.5 | 2.9 | 117 |
| | | 1pcr[88] | 2.65 | L-Asn183ND2 | M-Ser212O | 3.3 | 2.4 | 148 |
| | | | | M-Ala213CA | L-Asn183OD1 | 4.3 | 3.2 | 176 |
| | | | | | L-Ser237OG | 4.0 | 3.1 | 132 |
| | | 1aij[89] | 2.2 | L-Asn183ND2 | M-Ser212O | 3.1 | 2.22 | 148 |
| | | | | M-Ala213CA | L-Asn183OD1 | 4.4 | 3.3 | 165 |
| | | | | M-Ala217CA | L-Ser237OG | 3.4 | 2.9 | 111 |
| | | | | M-Gly220CA | L-His230O | 3.6 | 3.0 | 119 |
| | | 1aig[89] | 2.6 | L-Ser237OG | M-Ala213O | 2.8 | 1.85 | 165 |
| | | | | M-Ala213CA | L-Asn183OD1 | 3.1 | 2.2 | 140 |
| | | | | | L-Ser237OG | 3.4 | 2.6 | 126 |
| | | | | M-Ala217N | | 3.3 | 2.8 | 107 |
| | *B. viridis* | 1prc[66] | 2.3 | M-Ser271OG | L-Ala184O | 2.9 | 2.03 | 144 |
| | | | | L-Asn183ND2 | M-Cys210O | 3.4 | 2.57 | 146 |
| | | | | L-Ala184CA | M-Cys210SG | 4.2 | 3.3 | 140 |
| | | | | L-Gly188CA | M-Asn147OD1 | 3.7 | 3.0 | 120 |
| | | | | | M-Ser271OG | 3.4 | 2.8 | 114 |
| | *T. tepidum* | 1eys[90] | 2.2 | L-Asn191ND2 | M-Ser211O | 2.8 | 1.9 | 145 |
| | | | | M-Ala212CA | L-Asn191OD1 | 4.5 | 3.4 | 177 |
| | | | | M-Ala272CA | L-Cys192SG | 4.1 | 3.3 | 126 |
| Photosystem II RC | *T. elongatus* | 1s5l[7] | 3.5 | D1-Gly208CA | D2-Cys211SG | 4.3 | 3.3 | 149 |
| | | | | D1-Cys212SG | D2-Gly207O | 3.4$^a$ | | |
| | | | | D1-Cys212CA | D2-Cys211SG | 4.2$^a$ | | |
| | | | | D1-Ala213CA | D2-Met271O | 3.8 | 2.8 | 143 |
| | | | | D1-Gly216CA | D2-His268O | 3.3 | 2.5 | 130 |
| | | | | D1-Leu275CA | D2-Cys211SG | 3.8$^a$ | | |
| | | | | D1-Ala276CA | D2-Cys211O | 3.6 | 2.9 | 123 |
| | | | | D2-Cys211SG | D1-Gly208O | 4.0$^a$ | | |
| | | | | | D1-Leu275O | 3.5$^a$ | | |
| | | | | D2-Cys211N | D1-Cys212SG | 3.6$^a$ | | |
| | | | | D2-Ala212CA | D1-Leu275O | 4.2 | 3.5 | 130 |
| | | | | D2-Gly215CA | D1-His272O | 3.2 | 2.7 | 110 |
| | | 2axt[8] | 3.0 | D1-Ala209CA | D2-Gly207O | 4.0 | 3.0 | 152 |
| | | | | D1-Gly208CA | D2-Cys211SG | 3.9 | 3.2 | 127 |
| | | | | D1-Ala276CA | D2-Ala212O | 4.1 | 3.4 | 124 |

TABLE 2-continued

Potential ISHBs Involving the Transmembrane Regions of the D and E in the RC of Purple Bacteria and Photosystem II

| Organism | PDB/ Ref | Res. (Å) | HB Donor | HB Acceptor | D-A | DH-A | Angle |
|---|---|---|---|---|---|---|---|
| | | | D2-Ala212CA | D1-Leu275O | 3.9 | 2.9 | 147 |
| | | | D1-Cys212SG | D2-Met271O | 3.2 | 1.9 | 178 |
| | | | | D2-Gly207O | 3.2$^a$ | | |
| | | | D1-Ala213CA | D2-Met271O | 3.6 | 2.7 | 138 |
| | | | D2-Gly215CA | D1-His272O | 3.3 | 2.9 | 101 |
| | | | D1-Gly216CA | D2-His268O | 3.1 | 2.7 | 99 |
| | | | D2-Cys211SG | D1-Gly208O | 3.1$^a$ | | |
| | | | | D1-Leu275O | 4.0 | 2.8 | 156 |
| | | | D2-Met271CA | D1-Cys212SG | 3.8$^a$ | 3.2 | 113 |

Thus, changes in the amino acids within the identified GxxxG-like motif may result in modification of the RC localized flexibility and consequently, in the entropy of activation. Indeed, Ser occupies the D1-212 and D1-209 in mesophilic organisms including the cyanobacterium *Synechocystis* 6803. The D1-209 is modified to Ala in the thermotolerant red alga *Cyanidium caldarium*, and in thermophilic cyanobacteria, Cys or Ala populates the D1-212 while Ala occupies the D1-209 site (FIG. 1C).

Two sizable cavities augmented by several small ones complement the ISHB cluster (FIGS. 1A-B, 5A-E and Table 3). The largest cavity (47 Å$^3$) lay at the interface of the two subunits and extends from the D1-212 site toward the histidines that ligate the non-heme iron. A second cavity (32 Å$^3$) occupies the other side of the D1-212 residue and is lined by two flexible side-chains that are in common to the largest cavity. Consequently, movements or changes in the size of the D1-212 residue may alter the volume and shape of either cavity or merge the two cavities into one. In the structurally homologous domain in RC from purple bacteria, a large cavity encompassing over 100 Å$^3$ was found in this region. As previously demonstrated for bacteriorhodopsin [Friedman et al., *Biophys J* 85, 886-96 (2003)], such cavities in the inner core of a protein may facilitate the conformational rearrangement required for enhancing the protein's local flexibility during discrete functional steps.

TABLE 3

Cavities found between the D and E helices of bacterial RC and PSII RC

| PDB Code/ 212 residue | Molecular Surface (Å$^3$) | Atoms lining the cavity |
|---|---|---|
| Wild type - photosystem II (D1-212 = Cys) | | |
| 2axt | 46.8 | D1: Phe-211-O, Cys-212-CA, His-215-CB, Leu-275-CB/CD1/CD2<br>D2: Leu-210-O, Cys-211-CA/C/CB/SG, His-214-CB/CD2, Gly-215-N, Met-271-CE |
| | 31.8 | D1: G-208-CA, F-211-CB/CD1, F-274-O/CD2, L-275-CA/O/CD2, W-278-CB/CD1, P-279-CD<br>D2: C-211-SG |
| | 7.9 | D1: C-212-SG<br>D2: G-207-CA, L-210-CD1, M-274-CB/CG1, P-275-CD |
| | 6.2 | D1: C-212-SG<br>D2: L-210-CD1, M-271-CA, V-274-CB, P-275-CD |
| | 6.3 | D1: H-272-CD2, L-275-CD1<br>D2: H-214-CD2, G-215-N/CA |
| Photosystem II RC - Rotamer-library based D1-212 mutation | | |
| all residues | 40.2 | D1: F-211-C/O, RESIDUE-212-CA, H-215-CB, L-275-CB/CD1/CD2<br>D2: C-211-CA/C/CB/SG, H-214-CB/CD2, G-215-N, M-271-CE<br>* In the Gln and Glu mutants the OE1 atom is involved causing a decrease of 0.1, and 0.2 Å$^3$ in cavity volume, respectively.<br>In Arg and Trp the cavity is 39.7 Å$^3$ due to similar reasons. |
| | 28.8 | D1: G-208-CA, F-211-CD1, F-274-O/CD2, L-275-CA/O/<u>CD2</u>, W-278-CB/CD1, P-279-CD<br>D2: C-211-<u>SG</u> |
| Gly | 48.7 | D1: A-209-CA/O, G-212-CA/C<br>D2: G-207-CA/C/O, L-210-CB/CD1, C-211-N, M-271-CA/O/CB/CG/CE, P-275-CB/CG/CD |
| Ala/Cys/Ser | 21.9 | D1: A-212-CB<br>D2: G-207-CA, L-210-CB/CD1, M-271-CA/O/CB/CG/CE, P-275-CD<br>* In Cys/Ser the atoms are the same but cavity is 0.1 Å$^3$ smaller |
| Bacterial Reaction Center (Largest cavity only) | | |
| 1aij[16] | 108 | L subunit: Leu187-O/CD1, His190-CB/CD2, Gly191-N/CA,<br>M subunit: Leu215-O/CG/CD1/CD2, Phe216-CA/CD1/CE1/CZ,<br>His219-CB/CG/CD2/NE2, Ile265-C/O/CG1/CG2/CD1, His266-CA/CD2,<br>Ala269CB, U108-C1M |

TABLE 3-continued

Cavities found between the D and E helices of bacterial RC and PSII RC

| PDB Code/ 212 residue | Molecular Surface (Å$^3$) | Atoms lining the cavity |
|---|---|---|
| 2prc[66] | 135 | L subunit: Leu187-O/CD1/CD2, His190-CB/CD2, Gly191-N/CA, M subunit: Leu213-C/O/CB/CD1/CD2, Phe214-CA/CD1/CE1/CZ, His217-CB/CG/ND1/CD2/CD1/NE2, Val263-C/O/CG1/CG2, His264-CA/O/CG/CD2, Gly26-7N/CA/C, Trp268-N, 7MQ501-C3M |

Having two adjacent structural motifs associated with flexibility, inventors tentatively concluded that replacement of Ser by Cys or Ala within the GxxxG-like motif accounts for the observed changes in the localized protein flexibility and subsequently the temperature adjustment of the RC activity. In-silico rotamer-library based saturated mutagenesis was performed on the D1-212 site in the available structures of thermophilic cyanobacteria conservatively allowing only the D1-212 to re-pack. Under such constrains, the volume of the larger cavities was reduced by about 10-20% and the small ones merged into one. This new cavity was evident only in the mutants that had small residues (Gly, Ala, Cys, Ser; Table 3). In all other mutants the cavity was blocked by the D1-212 side-chain (FIGS. 3A-B and Table 3). Dissociation of ISHB between residues of the GXXXG-like motif should increase the localized flexibility provided that side chains are free to undergo reorganization. However, this freedom of motion was decreased when the packing values of the involved residues are decreased, shifting $T_o$ to higher values. Thus, Ala and Cys (packing value=0.471 and 0.463, respectively) were expected to correspond to higher $T_o$ values compared to Ser (packing value=0.484). Unlike the non-bulky resides (termed 'class I'), the bulky ones (termed 'class II') partly blocked the intersubunit cavity (FIG. 3A-B and Table 3). The latter had the lowest packing values and were expected to elevate $T_o$ to a non-physiological range where PSII RC denaturation takes over.

Inventors directly challenged the in-silico predictions by introducing mutations in photosystem II RC of *Synechocystis* 6803. The D1-S212 residue was replaced by each of the remaining 19 amino acids and the effect on the photosynthetic parameters in intact cells was investigated. Thirteen photoautotrophic mutant strains were isolated (see Materials section). Mutants with aromatic and positively charged residues, all assigned to class II, failed to grow photoautotrophically possibly due to impaired RC folding. Mutants containing class I residues (Gly, Cys, Ala, Thr, Asn, and Asp) presented similar patterns of $Q_A^- \rightarrow Q_B$ ET temperature dependence (FIG. 2B). Yet, $T_o$ was elevated by more than 6° C. and more than 7° C. in the D1-S212C and D1-S212A mutants, respectively. The rate constant reached similar maximum values (approximately 3-4×10$^3$ sec$^{-1}$) in the different class I mutants at their $T_o$ and above (FIG. 2B). Obtained photoautotrophic mutants with class II residues (Pro, Val, Ile, Leu, Glu, and Gln) presented significantly lower values for the ET rate constant and their k values increased in a monotonic, monophasic fashion with increasing temperature through most of the physiological range (FIG. 4A). ΔH$^{\ddagger}$ was similar in all class I residues but ΔS$^{\ddagger}$ at room temperature was more negative by 0.15 and 0.3 kcal·mol$^{-1}$ for the Cys and Ala-substituted strains (FIGS. 2B and 4B) depicting the significance of D1-212 in modulating the RC localized flexibility and $T_o$. For class II mutants, ΔH$^{\ddagger}$ was usually similar to the wild type and class I mutants (below $T_o$) but ΔS$^{\ddagger}$ was more negative by up to ~1.8 kcal·mol$^{-1}$ at room temperature (FIG. 4B) thus indicating decreased local flexibility of the transition state involved in the $Q_A^- \rightarrow Q_B$ ET in class II mutants.

Mutagenesis of the D1-S209 residue resulted in only eight photoautotropic mutants: six of class I (Gly, Ala, Thr, Asn, and Asp), and only two from class II (Val and Pro), possibly because substitution with residues of very low packing values impaired the PSII RC functional assembly. All photoautotrophic mutants exhibited levelling of the $Q_A^- \rightarrow Q_B$ ET rate at elevated temperatures (data not shown). The $T_o$ temperature of the D1-S209A mutant elevated by more than 7° C. while maintaining a similar maximal rate constant as the wild type. This finding supports the suggested significance of the D1-209 loci in modifying the local flexibility of PSII RC and thereby the value of $T_o$.

Collectively, the identified structural motifs (ISHBs in a GxxxG-like sequence motif and adjacent cavities) in purple bacteria and photosystem II RCs, appeared to function as key modulators in controlling the activation entropy of the $Q_A^- \rightarrow Q_B$ ET rate and subsequently the value of $T_o$.

Non Arrhenius behaviour of enzymatic rate constants has been frequently considered to reflect inactivation and denaturation of the examined enzymes. However, $T_o$ seems independent of the PSII RC denaturation which was introduced at significantly higher temperatures (FIG. 6). In search for an alternative explanation for the temperature dependence of k, inventors looked at the non-Arrhenius behaviour in hydrogen transfer enzymes. The thermostability of the PSII in the wild type and the mutants was deduced from the amplitude of the fastest fluorescence decay component that is directly proportional to the concentration of photosystem II RC active in $Q_A^-$ to $Q_B$ ET. As shown in FIG. 6, no significant change in the amplitude of the wild type fluorescence (D1-S212) was observed until approximately 37° C. and $T_{1/2}$ (50% inactivation) was achieved at approximately 45° C. Similar curves with practically the same $T_{1/2}$ were obtained for Ala and Cys. Thus, $T_o$ (25° C., FIGS. 2A, 4A) appear independent of the thermostability for the wild type and class I mutants of *Synechocystis* 6803. Class II mutants may show similar temperature dependence to class I mutants (Val) or much lower thermostability (Gln) with well defined Arrhenius behaviour throughout the entire range of measurements (FIG. 4B). Collectively, these findings exclude the involvement of photosystem II RC inactivation or denaturation in the non-Arrhenius behaviour of mesophiles, thermotolerant, thermophiles and class I mutants described.

In conclusion, inventors have shown that changes in locally flexible domains in membrane proteins provided the means for enzyme adaptation to the ambient temperature. Furthermore, inventors described and validated protein motifs that modulate this adaptation independently of denaturation processes.

Example 2

Temperature Dependence of the Electron Transfer Rate in the Different Single and Double Mutants of the *Synchocystis* Pp. 6803

The observed pattern of temperature dependence for the viable mutants (Table 4, below) of the *Synechocystis* mutants was the same as previously described for mutation with class I amino acid residues. Namely, the increase of electron transfer rate with temperature until an optimal temperature termed $T_o$ was reached (where the rate constant reached a plateau and leveled off, FIG. 7). In the D1-S212C and D1-SS209/212AC mutants, $T_o$ shifted to higher temperature (approximately 32-33° C.) compared to the one observed for the wild type (approximately 25° C.). The D1-S212P presented the same $T_o$ (approximately 25° C.) as a wild type, and in the D1-SS209/212AA, $T_o$ was down shifted by 2.5° C. (FIG. 7). The maximum electron transfer rate for the D1-S212C was the same as the one measured for the wild type wild type ($\sim$3-4×10$^3$ s$^{-1}$). All other mutants presented significantly lower rate constants (FIG. 7).

Example 4

Growth Rate of the Wild Type and the Mutants at Elevated Temperatures

The growth rate of the *Synechocystis* sp. PCC6803 wild type and mutant strains provided a direct estimate of the biomass production under different constrains. FIG. 8C depicts the time dependent turbidity of cell cultures grown at the physiological temperature (30° C.). All strains showed a significant growth rate where the biomass appears to increase by a factor of 14-16 after 6 days of growth. FIG. 8D shows that at 43° C. the wild type and the D1-SS209/212AA, stop growing and consequently die after 2 days. However, the biomass of the D1-S212C and D1-S212P increased at a rate of 6-6.5 fold after 6 days. Importantly, the growth arrest of the wild type and the D1-SS209/212AA are in line with the rapid decline of their chlorophyll content and the depletion of Rubisco and D1 proteins (FIGS. 8F, 8H and 8J).

TABLE 4

Viable and non-viable mutations of D1-212 and 209 sites

Viable and non-viable mutations at D1-212 site

| C | E | T | I | P | N | V | A | L | Q | M | D | G | F | W | Y | R | K | H |
|---|---|---|---|---|---|---|---|---|---|---|---|---|---|---|---|---|---|---|
| 4 | 1 | 2 | 5 | 3 | 1 | 4 | 4 | 10 | 4 | 3 | 10 | 15 | 0 | 0 | 0 | 0 | 0 | 0 |

Viable and non-viable mutations at D1-212 site

| C | G | T | P | N | V | A | D | E | I | L | Q | M | F | W | Y | R | K | H |
|---|---|---|---|---|---|---|---|---|---|---|---|---|---|---|---|---|---|---|
| 2 | 4 | 2 | 10 | 11 | 1 | 3 | 8 | 0 | 0 | 0 | 0 | 0 | 0 | 0 | 0 | 0 | 0 | 0 |

Table 4: describes statistical data for amino acid residues obtained in the degenerated mutagenesis. Optional amino acids that could be obtained by the combinatorial mutagenesis approach/amount of mutants obtained for each AA residue. Each transformation yielded around 300 colonies under selection conditions. Randomly selected colonies (Table 4) were picked up for each mutation and their genomic DNA was amplified by PCR with P3 and P5 oligonucleotides (Table 1). The type of mutation was checked by restriction pattern with NsiI and by directed sequencing of that PCR product. For D1-Ser212, a total of 13 functional mutant strains and 6 non-functional mutants were obtained. For D1-Ser209 a total of 9 functional mutant strains and 10 non-functional mutants were obtained.

Example 3

Thermotolerance of the Mutants

To determine the effect of mutation on high temperature tolerance, cultures of *Synechocystis* 6803 wild type (ΔKS), the single D1-S212C, D1-S212P and double D1-SS209/212AA, D1-SS209/212AC mutants were grown under standard (30° C.) and under high (43° C.) temperatures for six days. The phenotypes of both the mutants and ΔKS did not show a significant difference at 30° C. (FIG. 8A). However, bleaching of the wild type, D1-S212P and D1-SS209/212AA mutants was observed after 6 days of incubation at 43° C. (FIG. 8B) suggesting growth arrest, cell death and chlorophyll (Chl) degradation. This observation was reflected in the chlorophyll accumulations rates (FIGS. 8E-F). At 30° C., ΔKS and all mutants showed similar chlorophyll accumulation rates. At the high temperature limit (43° C.) and after 6 days of growth, D1-S212C and D1-SS209/212AC mutants presented several fold higher chlorophyll content than wild type and other mutants.

Example 5

Stability of D1 and Rubisco is Maintained in D1-S212C and D1-SS209/212AC

D1 and Rubisco are two essential proteins for photosynthesis and biomass formation, respectively [Haldimann and Feller, *Plant Cell and Environment* 28, 302-317 (2005); Kouril et al., *Photosynthesis Research* 81, 49-66 (2004)]. Grown under standard temperatures (30° C.) their expression was the same for both wild type and mutants (FIGS. 8G and 8I). However, expression of these proteins was arrested upon incubation at 43° C. for 6 days for wild type (ΔKS), D1-SS209/212AA and D1-S212P mutants (FIGS. 8H and 8J). Yet, D1-S212C and D1-SS209/212AC mutants present normal synthesis and accumulation of these proteins at both temperatures (FIGS. 8G-J). While the former is essential for light reactions, the latter catalyses the carbon dioxide uptake and fixation to form the carbohydrates. This example proves the viability of maintaining high biomass production in thermally adapted cyanobacteria after some mutations. Notably, Rubisco is known to undergo inactivation at increased temperatures [Berry and Bjorkman, *Ann. Rev. Plant Physiol.* 31, 491-543 (1980)] underscoring the major inhibition of large scale biomass production at elevated temperatures in mesophiles. The psaC protein, which is part of PSI protein complex, while present at 30° C. (FIG. 8K) was depleted in the wild type and D1-SS209/212AA mutant at 43° C. (FIG. 8L).

Example 6

Thermoplasticity Tests

The thermoplasticity of wild type and mutants was examined by subjecting the strains to high/low temperature cycles. First, cell cultures were acclimated to 43° C.-30° C.-43° C. cycle for 48 hours at each temperature (FIGS. 9A, 9C and 9E). Similarly all the cultures were acclimated at high temperature and then abruptly shifted to low temperature (43° C.-10° C.-43° C. cycle) for 48 hours at each temperature (FIGS. 9B, 9D and 9F). As depicted in FIG. 9A, only D1-S212C and D1-SS209/212AC mutants survived at the high temperature after 43° C.-30° C.-43° C. cycle, while ΔKS and the other two mutant strains were completely bleached. The D1-S212C mutant showed the highest survival rate and the highest biomass production as reflected in the growth rates and chlorophyll accumulation curves (FIGS. 9C and 9E, respectively). The D1-SS209/212AC mutant had comparable biomass production after periodic temperature changes (FIGS. 9C and 9E). All the other strains did not endure the treatment (FIGS. 9C and 9E). Acclimation at 43° C.-10° C.-43° C. cycle resulted in an impairment of mainly the wild type strain (FIGS. 9B, 9D and 9F) although the D1-S212P mutant also seems to be impaired. As shown in FIGS. 10A-C (10° C.-43° C.-10° C. cycle) a very slow growth rate was observed at 10° C. As the temperature was elevated to 43° C., the wild type and D1-SS209/212AA mutants showed significant decline while no increase was recorded in the remaining strains. As the temperature dropped back to 10° C., the growth of all the strains was practically arrested but a clear decline of the wild type was obvious.

Example 7

Enhancement of D1 Stability and Rubisco Activation in the Wild Type and Different Mutants Under High and Low Temperatures Following the 43° C.-30° C.-43° C. cycle, D1 protein levels were high in S212C while they were found to be expressed at lower levels in the D1-SS209/212AC mutants (FIG. 9G). In the other strains, D1 protein levels were essentially depleted (FIG. 9G). The Rubisco and psaC protein were found to be stably expressed and at higher concentrations in D1-S212C and in D1-SS209/212AC mutants compared to the other strains which did not present detectable amounts (FIGS. 9I and 9K).

The outcome of the second temperature cycle (43° C.-10° C.-43° C. cycle) was very different as shown in FIGS. 9F, 9H, 9J and 9L. At 43° C. (during the first 48 hours) the chlorophyll content was increased for all the cultures then at subsequent two days at low temperature (10° C.) the chlorophyll quantity was slightly dropped in all strains and after the shift to 43° C. all the cultures maintain their chlorophyll levels (FIG. 9F). D1-S212C mutant had the best chlorophyll accumulation rates and higher biomass compared to all other strains at the mentioned conditions (FIG. 9F). Although the phenotypes of the strains were not very different from each other as it is shown by their color (FIG. 9B), the D1-S212C and D1-SS209/212AC mutants maintained the highest chlorophyll content as well as the highest biomass production (FIG. 9F). After the temperature treatment in this cycle, the steady content of Rubisco and psaC proteins was not changed in the wild type and all the mutants (FIGS. 9J and 9L). The D1 protein was severely depleted in the wild type but not in the mutant strains (FIG. 9H).

D1 protein levels were barely detectable in wild type, D1-SS209/212AA and D1-S212P mutants grown at 10° C.-43° C.-10° C. conditions (FIG. 10D), while, detectable D1 levels were demonstrated for D1-S212C and D1-SS209/212AC mutants (FIG. 10D). Rubisco levels were not detected in wild type and D1-SS209/212AA strains, however, similar Rubisco levels were detected in D1-S212C, D1-S212P and D1-SS209/212AC mutants (FIG. 10E). In contrast, all the strains exhibited similar and stable levels of psaC protein of PSI (FIG. 10F).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. An isolated polynucleotide comprising the nucleic acid sequence encoding a D1 polypeptide as set forth in SEQ ID NO: 36 of a Type II reaction center of a photosynthetic organism, wherein said D1 polypeptide comprises amino acid sequence modifications at a D1/D2 interface position corresponding to Serine 209 of SEQ ID NO: 36 and a position corresponding to Serine 212 of SEQ ID NO: 36, said amino acid modifications impart said type II reaction center with an activity under a higher temperature range than that of a type II reaction center endogenous to said photosynthetic organism.

2. A nucleic acid construct comprising the polynucleotide of claim 1.

3. The nucleic acid construct of claim 2, further comprising a cis-regulatory element.

4. A cell of a photosynthetic organism comprising the nucleic acid sequence of claim 1.

5. A photosynthetic organism comprising the exogenous nucleic acid sequence encoding a D1 polypeptide as set forth in SEQ ID NO: 36 of a type II reaction center of the photosynthetic organism, wherein said D1 polypeptide comprises amino acid sequence modifications at a D1/D2 interface position corresponding to Serine 209 of SEQ ID NO: 36 and a position corresponding to Serine 212 of SEQ ID NO: 36, said amino acid modifications impart said type II reaction center with an activity under a higher temperature range than that of a type II reaction center endogenous to said photosynthetic organism.

6. A method of improving biomass/vigor/yield of a photosynthetic organism comprising introducing into the photosynthetic organism the isolated polynucleotide of claim 1, thereby increasing biomass, vigor and/or yield of the photosynthetic organism.

7. A method of increasing activity of a type II reaction center of a photosynthetic organism under non-physiological temperature, the method comprising introducing into the photosynthetic organism the isolated polynucleotide of claim 1, thereby increasing the activity of a type II reaction center under a non-physiological temperature.

8. A method of increasing hydrogen production in a photosynthetic organism, the method comprising introducing into the photosynthetic organism capable of generating hydrogen the isolated polynucleotide of claim 1, thereby increasing hydrogen production in the photosynthetic organism.

9. The isolated polynucleotide of claim 1, wherein said polypeptide comprises the amino acid sequence as set forth in SEQ ID NO: 56.

10. The isolated polynucleotide of claim 1, wherein said amino acid sequence modification at a position corresponding to Serine 209 of SEQ ID NO: 36 comprises a Serine to Alanine mutation.

11. The isolated polynucleotide of claim 1, wherein said amino acid sequence modification at a position corresponding to Serine 212 of SEQ ID NO: 36 comprises a Serine to Cysteine mutation.

12. The isolated polynucleotide of claim 1, wherein said amino acid sequence modifications at said D1/D2 interface comprises a substitution.

13. The photosynthetic organism of claim 5, wherein said polypeptide comprises the amino acid sequence as set forth in SEQ ID NO: 56.

14. The photosynthetic organism of claim 5, wherein said amino acid sequence modification at a position corresponding to Serine 209 of SEQ ID NO: 36 comprises a Serine to Alanine mutation.

15. The photosynthetic organism of claim 5, wherein said amino acid sequence modification at a position corresponding to Serine 212 of SEQ ID NO: 36 comprises a Serine to Cysteine mutation.

16. The photosynthetic organism of claim 5, wherein said amino acid sequence modifications at said D1/D2 interface comprises a substitution.

* * * * *